(12) United States Patent
Pulici et al.

(10) Patent No.: US 8,809,337 B2
(45) Date of Patent: Aug. 19, 2014

(54) CARBAMOYL DERIVATIVES OF BICYCLIC CARBONYLAMINO-PYRAZOLES AS PRODRUGS

(71) Applicant: Nerviano Medical Sciences S.R.L., Nerviano (IT)

(72) Inventors: Maurizio Pulici, Caponago (IT); Paolo Polucci, Cassina Rizzardi (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/630,009

(22) Filed: Sep. 28, 2012

(65) Prior Publication Data

US 2013/0203770 A1    Aug. 8, 2013

Related U.S. Application Data

(62) Division of application No. 12/991,564, filed as application No. PCT/EP2009/055802 on May 14, 2009, now abandoned.

(30) Foreign Application Priority Data

May 15, 2008    (EP) .................................... 08156262

(51) Int. Cl.
| | | |
|---|---|---|
| *A61K 31/496* | (2006.01) | |
| *A61K 31/4162* | (2006.01) | |
| *A61K 31/454* | (2006.01) | |
| *C07D 401/14* | (2006.01) | |
| *C07D 401/12* | (2006.01) | |
| *C07D 495/04* | (2006.01) | |

(52) U.S. Cl.
USPC .................. 514/253.04; 514/254.06; 514/407; 514/322; 544/362; 544/371; 548/360.5; 546/199

(58) Field of Classification Search
USPC ........ 514/253.04, 254.06, 407, 322; 544/362, 544/371; 546/199; 548/360.5
See application file for complete search history.

(56) References Cited

FOREIGN PATENT DOCUMENTS

| WO | WO 2004/080457 A1 | 9/2004 |
|---|---|---|
| WO | WO 2004/113303 A1 | 12/2004 |
| WO | WO 2005/005427 A1 | 1/2005 |
| WO | WO 2005/074922 A1 | 8/2005 |
| WO | 2007009898 A1 | 1/2007 |
| WO | 2007068619 A1 | 6/2007 |
| WO | 2007068637 A1 | 6/2007 |
| WO | 2007138017 A1 | 12/2007 |
| WO | WO 2008/043745 A1 | 4/2008 |
| WO | 2008154241 A1 | 12/2008 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Pevarello P. et al., "3-Amino-1, 4, 5, 6-Tetrahydropyrrolo[3,4-c]Pyrazoles: A New Class of CDK2 Inhibitors", *Bioorganic & Medicinal Chemistry Letters* 16(4):1084-1090 (Feb. 15, 2006).
Lee S. et al., "Synthesis and Biological Evaluation of 3, 5-Diaminoindazoles as Cyclin-Dependent Kinase Inhibitors", *Bioorganic & Medicinal Chemistry Letters* 18(7):2292-2295 (Mar. 6, 2008).
Fancelli D. et al., "Potent and Selective Aurora Inhibitors Identified by the Expansion of a Novel Scaffold for Protein Kinase Inhibition", *Journal of Medicinal Chemistry* 48(8):3080-3084 (Apr. 21, 2005).
Simplício A.L. et al., "Prodrugs for Amines", *Molecules* 13(3):519-547 (Jan. 1, 2008).
Bundgaard J., "Novel Chemical Approaches in Prodrug Design", *Drugs of the Future* 16(5):443-458 (May 1, 1991).
International Search Report dated Aug. 11, 2009 received from the European Patent Office from related International Application No. PCT/EP2009/055802.
U.S. Office Action dated Jun. 28, 2012 from parent U.S. Appl. No. 12/991,564.
Fancelli, et al., "1,4,5,6-Tetrahydropyrrolo[3,4-c]pyrazoles: Identification of a Potent Aurora Kinase Inhibitor with a Favorable Antitumor Kinase Inhibition Profile", J. Med. Chem., Jul. 28, 2006, pp. 7247-7251, vol. 49, American Chemical Society.
Japanese Office Action dated Nov. 26, 2013 issued in Japanese Application No. 2011-50891 together with English language translation.

* cited by examiner

*Primary Examiner* — Kristin Vajda
(74) *Attorney, Agent, or Firm* — Scully, Scott, Murphy & Presser, P.C.

(57) ABSTRACT

There are provided bicyclic carbonylamino-pyrazoles of formula (I), wherein the variables are as specified in the claims, for use as medicament, in particular for the treatment of diseases due to the malfunctioning of protein kinases (PKs), such as cancer, pharmaceutical compositions comprising such carbamoyl derivatives, and their use as prodrugs of therapeutically active agents. Method of treatment and some new bicyclic carbonylamino-pyrazoles are also object of the present invention.

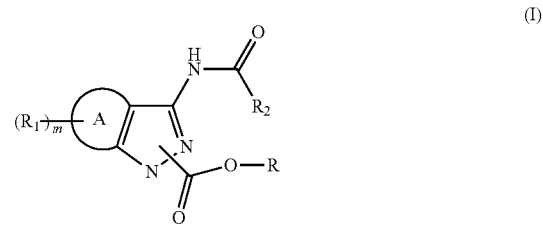

3 Claims, No Drawings

CARBAMOYL DERIVATIVES OF BICYCLIC CARBONYLAMINO-PYRAZOLES AS PRODRUGS

CROSS REFERENCE TO RELATED APPLICATIONS

The present application is a divisional of co-pending application having U.S. Ser. No. 12/991,564, filed on Nov. 8, 2010, which is a 371 of International Application having Serial No. PCT/EP2009/055802, filed on May 14, 2009, which claims priority of European Patent Application No. 08156262.1, filed on May 15, 2008, the contents of all of which are incorporated herein by reference.

The present invention relates to carbamoyl derivatives of bicyclic carbonylamino-pyrazoles for use as medicament, in particular for the treatment of diseases due to the malfunctioning of protein kinases (PKs), such cancer and tumors, to the pharmaceutical compositions comprising such carbamoyl derivatives, and to their use as prodrugs of therapeutically active agents.

The present invention also relates to a method of treating cancer and cell proliferation disorders using such prodrugs, and to some new carbamoyl derivatives.

The malfunctioning of protein kinases (PKs) is the hallmark of numerous diseases.

A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Among the several protein kinases known in the art as being implicated in the growth of cancer cells are Aurora kinases, in particular Aurora-2.

Aurora-2 was found to be over-expressed in a number of different tumor types. Its gene locus maps at 20q13, a chromosomal region frequently amplified in many cancers, including breast [Cancer Res. 1999, 59(9), 2041-4] and colon.

20q13 amplification correlates with poor prognosis in patients with node-negative breast cancer and increased Aurora-2 expression is indicative of poor prognosis and decreased survival time in bladder cancer patients [J. Natl. Cancer Inst., 2002, 94(17), 1320-9]. For a general reference to Aurora-2 role in the abnormal centrosome function in cancer see also Molecular Cancer Therapeutics, 2003, 2, 589-595.

The insulin-like growth factor 1 receptor (IGF-1R, IGF1R) is a member of the insulin receptor subfamily of RTKs. There exist several lines of evidence suggesting that IGF-1R signaling can contribute to tumour genesis, and that interfering with IGF-1R function represents a valid therapeutic option in cancer. Forced expression of the receptor leads to ligand-dependent transformed growth of murine and of rat fibroblasts (e.g. Kaleko M., Rutter W. J. and Miller A. D. Mol Cell Biol vol. 10, pages 464-73, 1990; Rubini M., Hongo A., D'Ambrosio C. and Baserga R. Exp Cell Res vol. 230, pages 284-92, 1997), and such transformed cells are able to form tumors in vivo, with both in vitro transformation and tumor formation in vivo being dependent upon an active kinase domain (reviewed in Blakesley V. A., Stannard B. S., Kalebic T., Heiman L. J., and LeRoith D. J. Endocrinol. vol. 152, pages 339-44, 1997). Compounds that are claimed having protein kinases inhibition activity for use in treating numerous diseases due to the malfunctioning of protein kinases are disclosed for example in WO 02/12242 (Various fused Pyrazoles); WO 03/028720, WO 08/074,749 and WO 09/013,126 (Aminoindazoles); WO 04/056827, WO 05/005427, WO2008017465 and WO2008043745 (Pyrrolo-pyrazoles); WO 04/007504, WO 04/013146, WO 05/074922, WO 07/009898, WO07/138017 and EP 2058315 (Furo- and Thieno-pyrazoles); WO 07/099171, WO 07/068637, WO 07/99166 and WO 07/068619 (Arylsulfo-pyrrolo-pyrazoles and arylsulfo-pyrrolo-pyridines).

Such patent applications also disclose processes for preparing the claimed compounds, which processes can comprise intermediates characterized from an ethoxycarbonyl group on one of the nitrogen atoms present in the pyrazole ring.

All the patents, patent applications and scientific publications cited in the present disclosure are incorporated herein by references.

The administration and therapeutic effectiveness of such compounds having protein kinases inhibition could be limited, however, for example for low or absence of oral bioavailability, low water solubility or stability.

Moreover, since these chemotherapeutic agents can be cytotoxic to normal tissues, the use of prodrugs is beneficial in terms of reduction of the side-effects.

A large amount of prodrug strategies are known, based on various modifications of the parent drug, but none of them teaches or suggests the specific prodrugs of the present inventions.

On the contrary, the above noted patent applications describe some carbamoyl derivatives as useful intermediates for the chemical preparation of the desired final active drugs. The identification of the new use is therefore completely unexpected.

It is an object of the invention to provide a compound of the formula (I) for use as medicament, preferably as prodrug, useful in therapy as agent against a host of diseases caused by and/or associated to a disregulated protein kinase activity, that is for the treatment of diseases due to the malfunctioning of protein kinases (PKs), such cancer or tumors.

More specifically, the prodrugs of this invention are useful in the treatment of a variety of cancers including, but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these prodrugs are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

Accordingly, in a first embodiment, the present invention provides a compound of the formula (I):

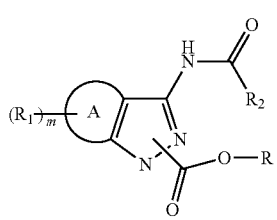

wherein
R represents a straight or branched $C_1$-$C_{12}$ alkyl, an aryl or heteroaryl group,
$R_1$ represents a hydrogen atom or a substituent attached to any available atom of the A ring,
$R_2$ represents an optionally substituted group selected from straight or branched $C_1$-$C_6$ alkyl, aryl, heteroaryl, $C_3$-$C_6$ cycloalkyl, $C_2$-$C_6$ alkenyl or alkynyl, $C_3$-$C_6$ cycloalkyl $C_1$-$C_6$ alkyl, aryl $C_1$-$C_6$ alkyl, heteroaryl $C_1$-$C_6$ alkyl, a 5 or 6 membered heterocyclyl and heterocyclyl $C_1$-$C_6$ alkyl with from 1 to 3 heteroatoms selected from nitrogen, oxygen and sulphur,
A ring represents a phenyl or a heterocycle and
m is a value from 1 to 6,
or a pharmaceutically acceptable salt thereof, for use as a medicament.

More preferably, the present invention provide a compound of formula (I) as defined above for use as a prodrug. Even more preferably, the invention provides a compound of formula (I) as above defined for use as prodrug for treating cell proliferative disorders caused by and/or associated with an altered protein kinase activity, in particular cancer.

The invention further provides any therapeutic method of treatment using as prodrug a compound of the formula (I) as defined above.

It is still a further object of the present invention a compound of the formula (I) as defined above characterized in that R does not represent an usubstituted ethyl group.

The present invention also provides a method for treating cell proliferative disorders caused by and/or associated with an altered protein kinase activity, which comprises administering to a mammal in need thereof an effective amount of a compound of formula (I) as above defined.

The above method enables treatment of cell proliferative disorders caused by and/or associated with altered protein kinases, for example Aurora kinases or IGF-1R activity.

In a preferred embodiment of the method described above, the cell proliferative disorder is cancer.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

The present invention also includes pharmaceutical compositions comprising a compound of formula (I) as defined above or a pharmaceutically acceptable salt thereof in association with a pharmaceutically acceptable excipient, which may be a carrier or a diluent, and to a method for treating cell proliferative disorders caused by and/or associated with an altered protein kinase activity, which comprises administering to a mammal in need thereof an effective amount of a compound of formula (I) as above defined or a pharmaceutical composition as specified herein. A more complete appreciation of the invention and many of the attendant advantages thereof will be readily obtained as the same becomes better understood by reference to the following detailed description.

The compounds of formula (I) may have asymmetric carbons and may therefore exist either as racemic admixtures or as individual optical isomers.

Accordingly, all the possible isomers and their admixtures are also within the scope of the present invention. In addition to the above, as will be readily appreciated, the compounds of formula (I) may exist as isomers or mixtures thereof of the formulas (Ia) and (Ib):

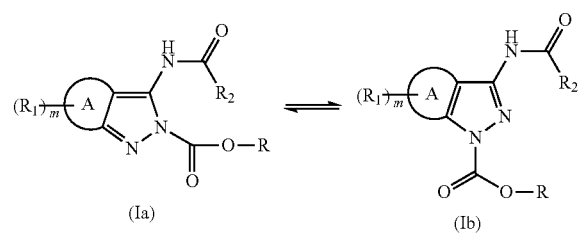

The two isomers of formula (Ia) and (Ib) may be conveniently separated according to well-known methods, for instance under chromatographic conditions, and each isomer so isolated subsequently worked out. In the alternative, the mixture of isomers can be treated as such in the subsequent steps of the process, without providing any separation.

The above process can be carried out according to methods well known in the art.

From all of the above, it is clear to the person skilled in the art that if a compound of formula (I), prepared according to the above process, is obtained as a mixture of isomers, their separation into the single isomers of formula (I), carried out according to conventional techniques, is still within the scope of the present invention.

Likewise, the conversion into the free compound (I) of a corresponding salt thereof, according to well-known methods, is still within the scope of the invention.

As used herein, unless otherwise specified, with the term straight or branched $C_1$-$C_{12}$ or
$C_1$-$C_6$ alkyl, either as such or as aryl $C_1$-$C_6$ alkyl or heteroaryl $C_1$-$C_6$ alkyl, we intend a group such as, for instance methyl, ethyl, n-propyl, isopropyl, n-butyl, t-butyl, sec-butyl, n-pentyl, n-hexyl, n-heptyl, and the like. Preferably, it is a $C_1$-$C_4$ alkyl, e.g. methyl, ethyl, n-propyl, isopropyl, n-butyl, t-butyl, sec-butyl.

With the term aryl group we intend any aromatic carbocyclic ring system of 1 or 2 ring moieties, either fused or linked to each other through a single bond, for instance including phenyl, -or -naphthyl or biphenyl groups. With the term heteroaryl we intend any aromatic heterocyclic ring which may comprise an optionally benzocondensed 5 or 6 membered heterocycle with from 1 to 3 heteroatoms selected among N, O or S.

Non limiting examples of heteroaryl groups according to the invention may thus include, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, and the like.

With the term halogen atom we intend a fluorine, chlorine, bromine or iodine atom.

With the term $C_3$-$C_6$ cycloalkyl we intend any group such as cyclopropyl, cyclobutyl, cyclopentyl or cyclohexyl.

With the term $C_2$-$C_6$ alkenyl or $C_2$-$C_6$ alkynyl group we intend any unsaturated straight or branched group such as, for instance, vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term heterocycle, heterocyclyl or heterocyclic group we also intend an optionally benzocondensed 4 to 7 membered heterocycle, hence encompassing aromatic heterocyclic groups also known as heteroaryl groups, either saturated or partially unsaturated, with from 1 to 3 heteroatoms selected among N, O and S.

Examples of these 4 or 7 membered heterocyclic groups are, for instance, 1,3-dioxolane, pyran, pyrrolidine, pyrroline, imidazoline, imidazolidine, pyrazolidine, pyrazoline, piperidine, piperazine, morpholine, tetrahydrofuran, hexamethyleneimine, 1,4-hexahydrodiazepine, azetidine, and the like.

According to the present invention, A ring in formula (I) above represents a phenyl or a heterocycle such as

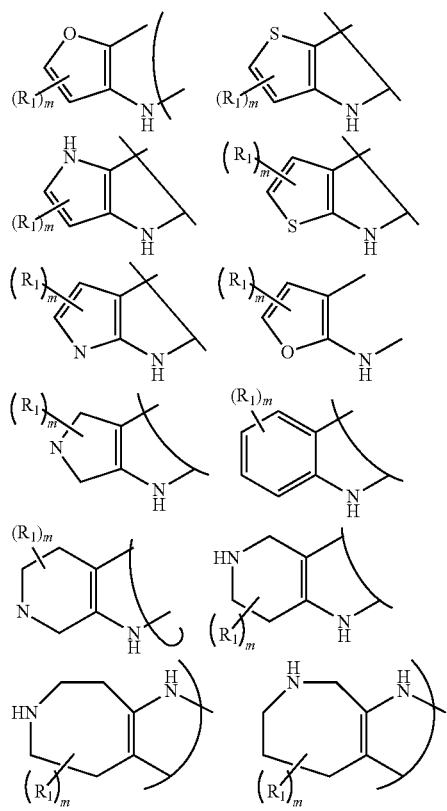

wherein $R_1$ and m are as defined above.

When $R_1$ represents a substituent attached to any available atom of the A ring, it is selected from: halogen, nitro, oxo groups (=O), carboxy, cyano, alkyl, polyfluorinated alkyl, alkenyl, alkynyl, cycloalkyl, cycloalkenyl; aryl, heterocyclyl, alkyl-heterocyclyl, heterocyclyl-alkyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, heterocylyloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

Needless to say, when m is neither one nor zero, the two or more substituents that $R_1$ represents may be the same, such as two methyl groups, or have different meanings, for example halogen atom and alkyl, on the same atom or on two or more different atoms of the A ring.

In their turn, whenever appropriate, each of the above substituents may be further substituted by one or more of the aforementioned groups.

According to the meanings provided to the groups R and $R_2$, any of the groups in their definitions above may be optionally further substituted in any of their free positions by one or more groups, for instance 1 to 6 groups, such substituents being as defined above for $R_1$.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic or organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, arylaliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base. Preferably, the present invention provides a compound of formula (I'), (I''), (I'''), (I''''), (I'''''), (I''''''), (I''''''') and (I$^{viii}$):

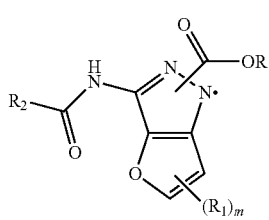

(I$^{ii}$)

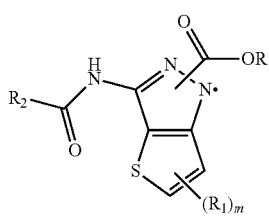

(I$^{iii}$)

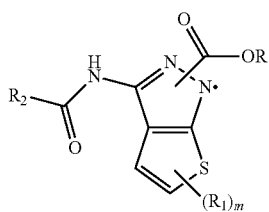

(I$^{iv}$)

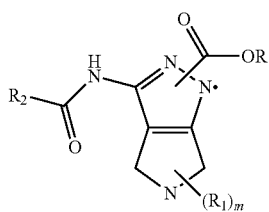

(I$^{v}$)

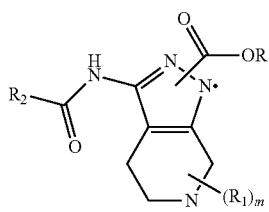

(I$^{vi}$)

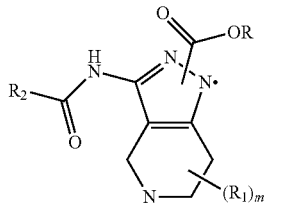

(I$^{vii}$)

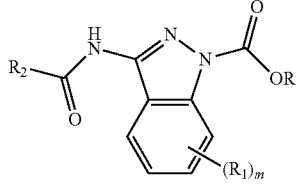

(I$^{i}$)

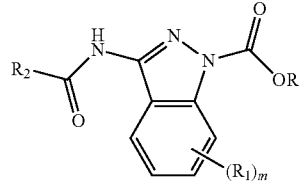

(I$^{viii}$)

wherein m, R, R$_1$ and R$_2$ are as defined above; for example when m is 2 or 3, the further R$_1$ substituent(s) on the phenyl or heterocyclic ring represent(s) a methyl, ethyl or cyclopropyl group.

In the displayed formulas in the present specification, a dotted line crosses the bond that links the substituent to the main framework of the molecule.

Preferably, R is a group selected from

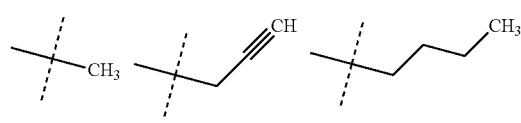

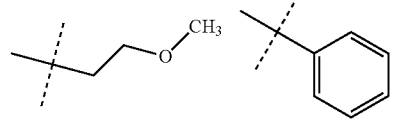

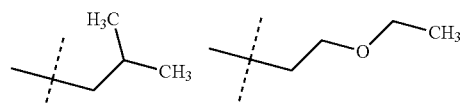

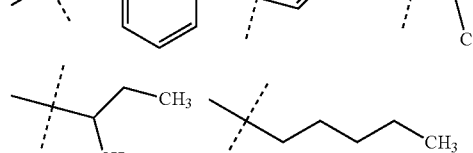

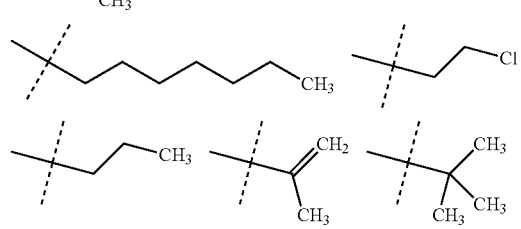

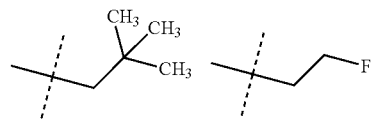

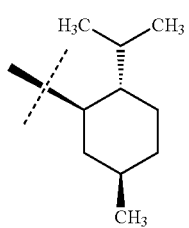
Preferably, for a compound of the formula (I'), (I''), (I'''), (I''''), (I'''''), (I''''''), R$_1$ is a group selected from:
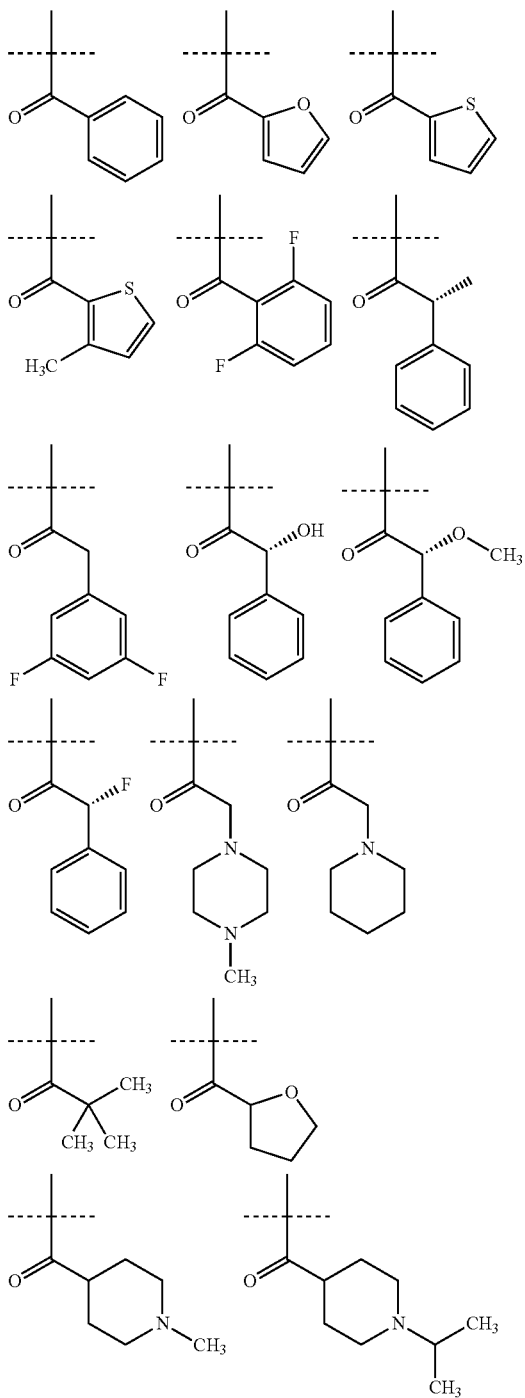
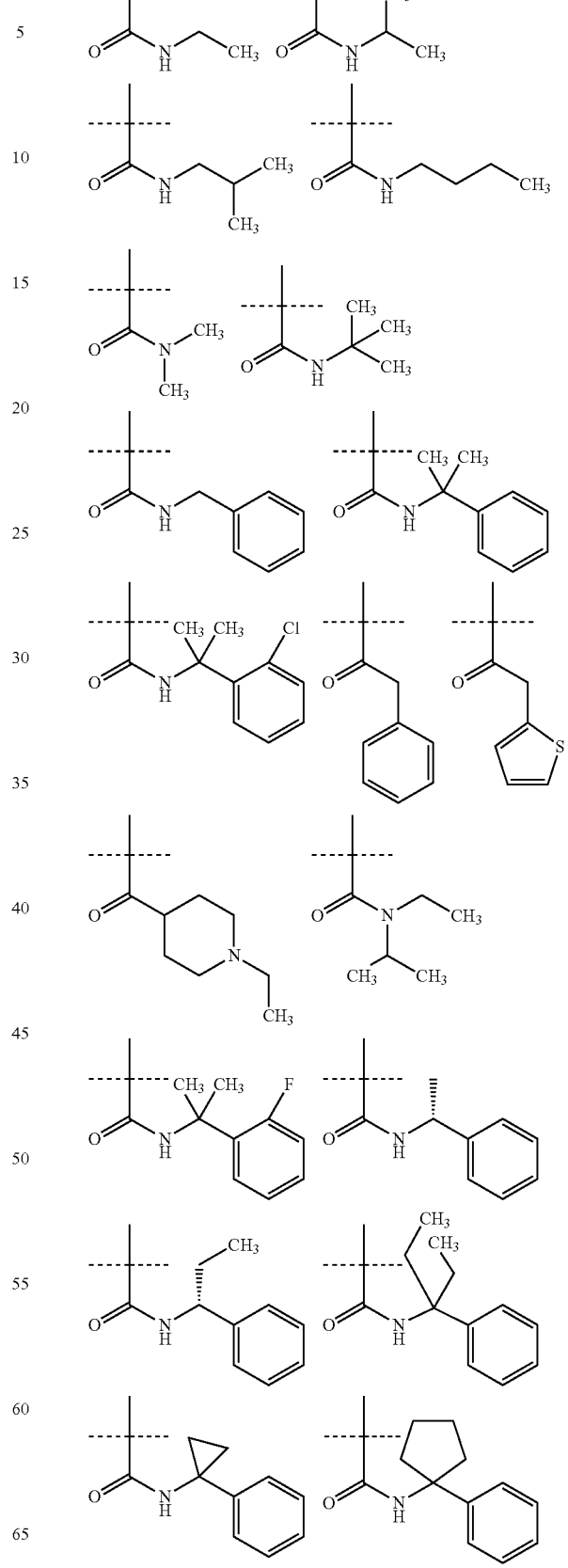

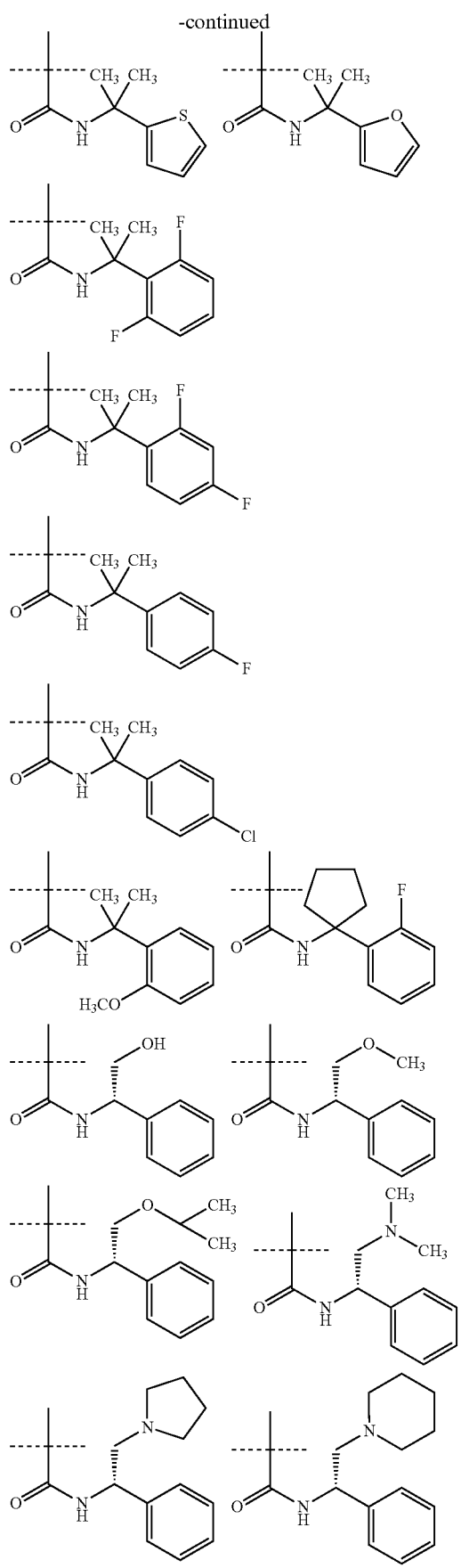
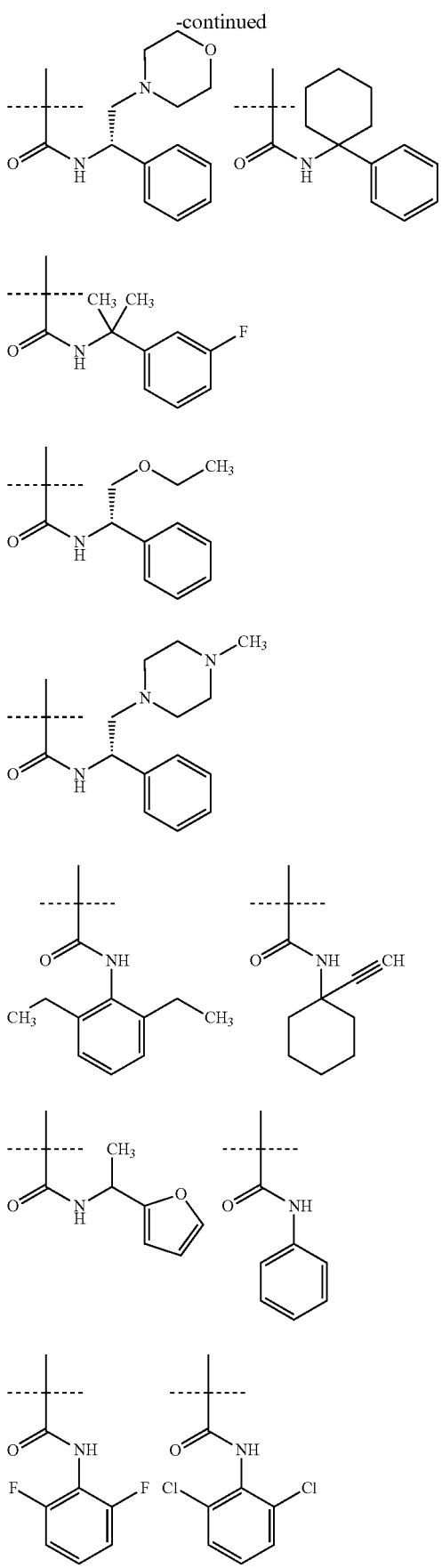

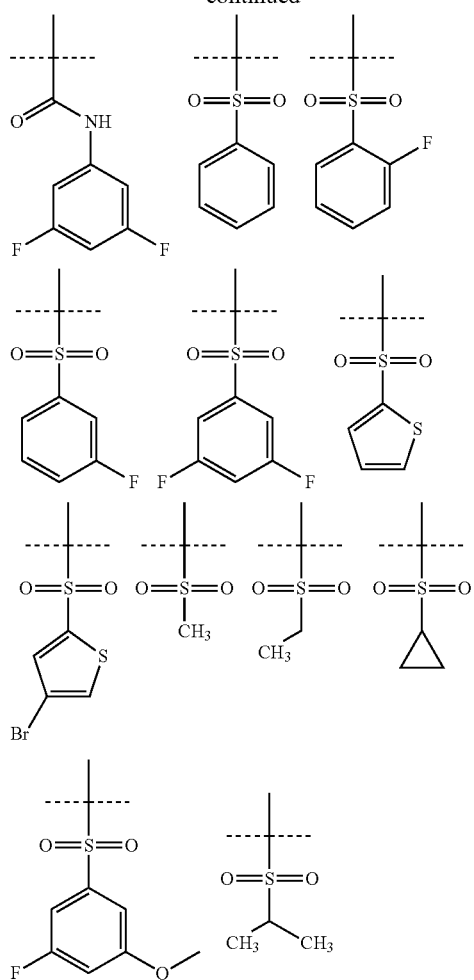
and, more preferably, the above defined $R_1$ substituent in a compound of the formula ($I^{iv}$), ($I^v$) or ($I^{vi}$) is on the heteroatom.
Preferably, for a compound of the formula ($I^{vii}$) or ($I^{viii}$), $R_1$ is a group selected from:
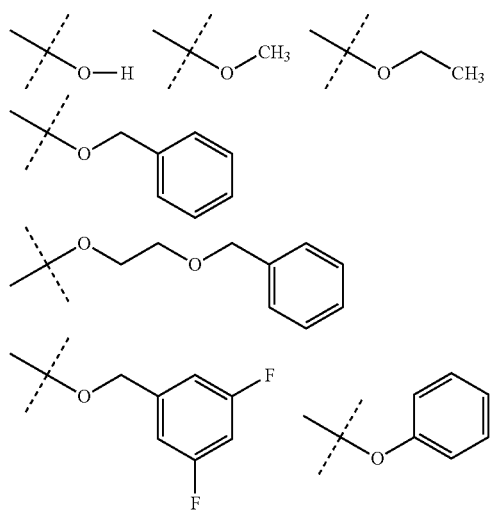
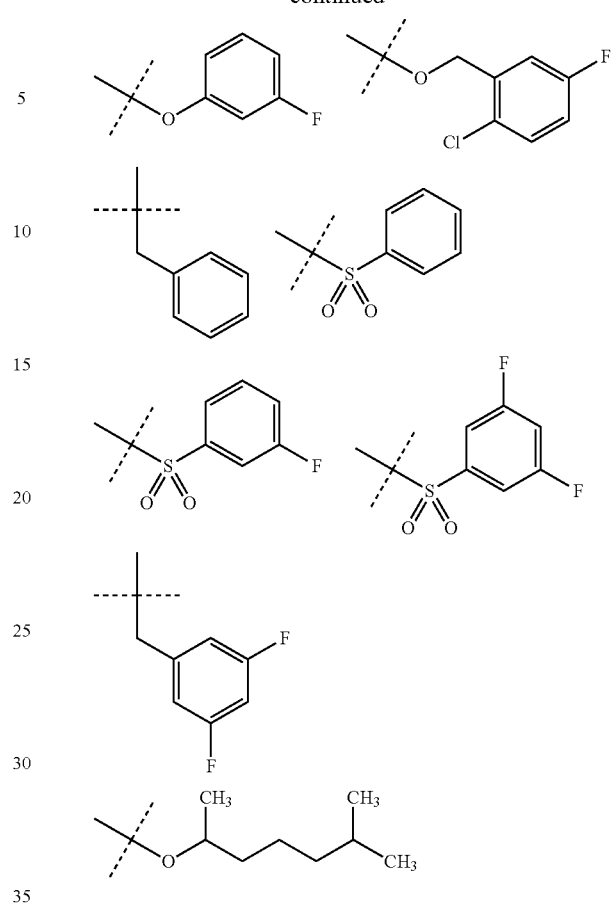
Lastly, preferably $R_2$ is a group selected from:
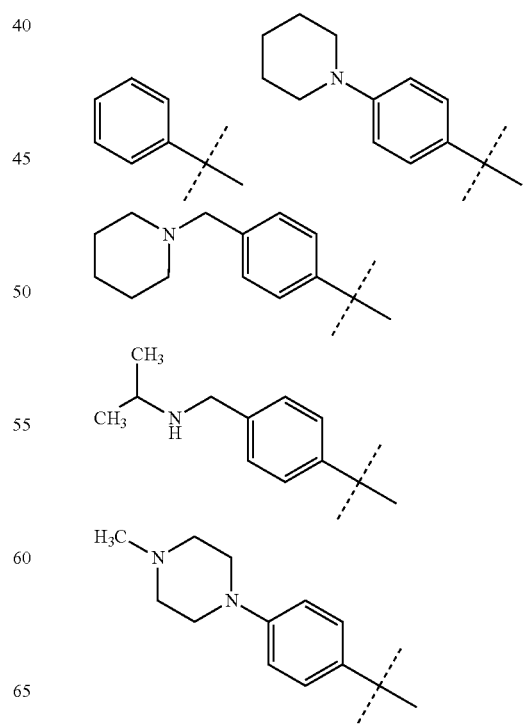

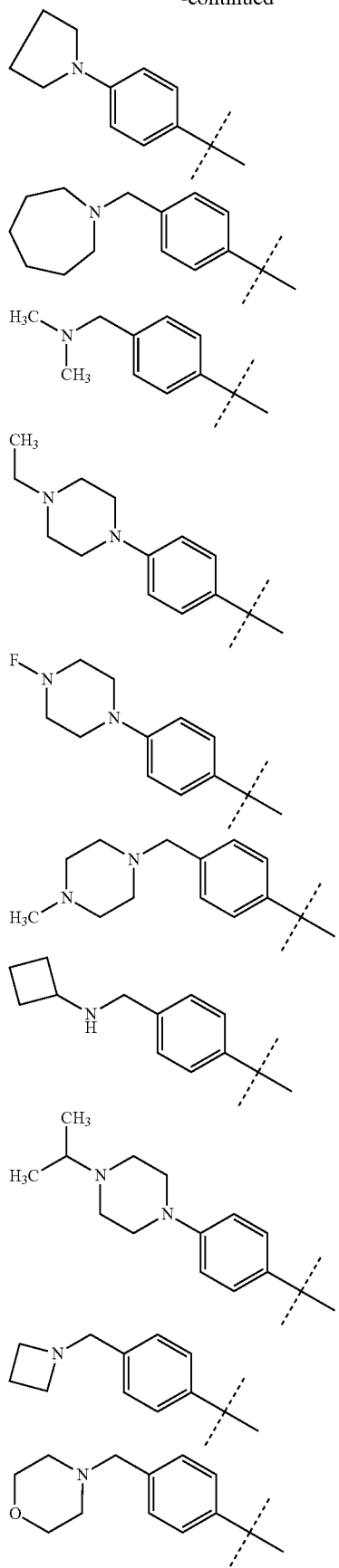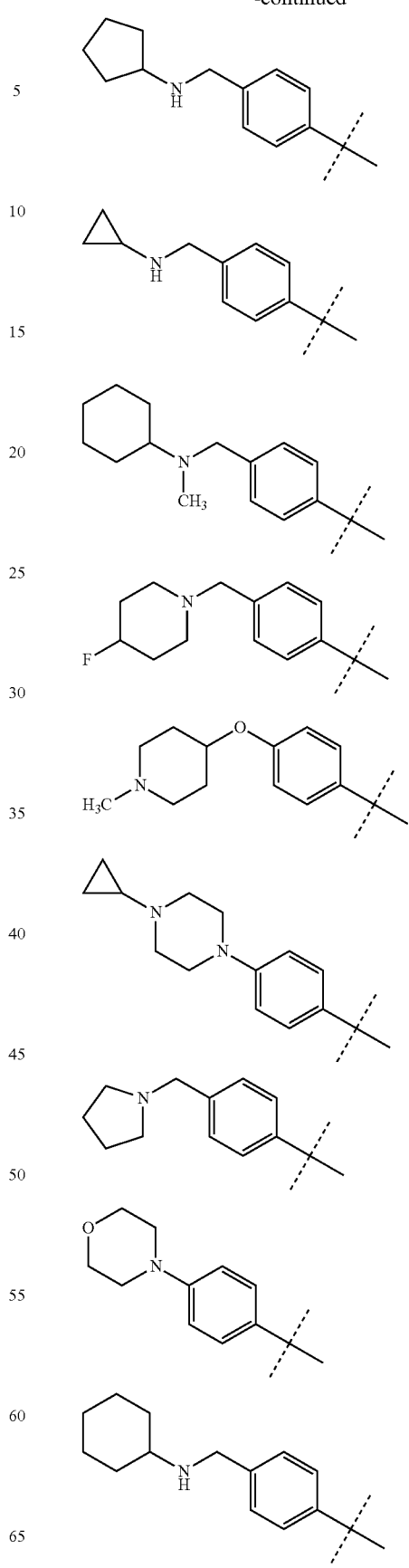

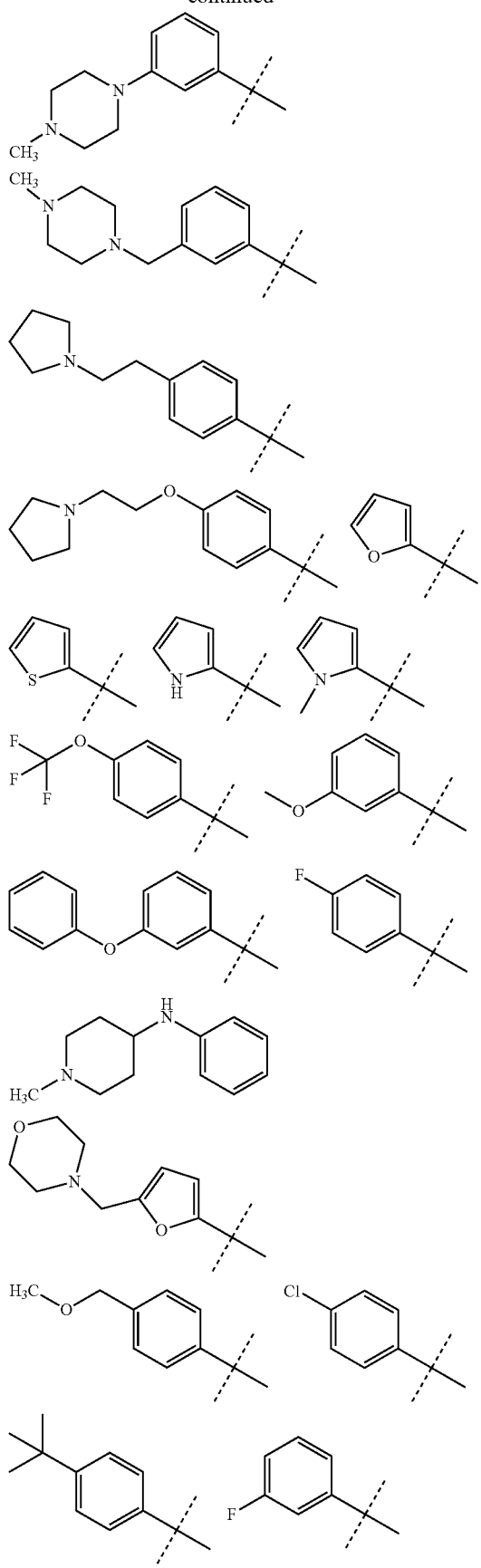
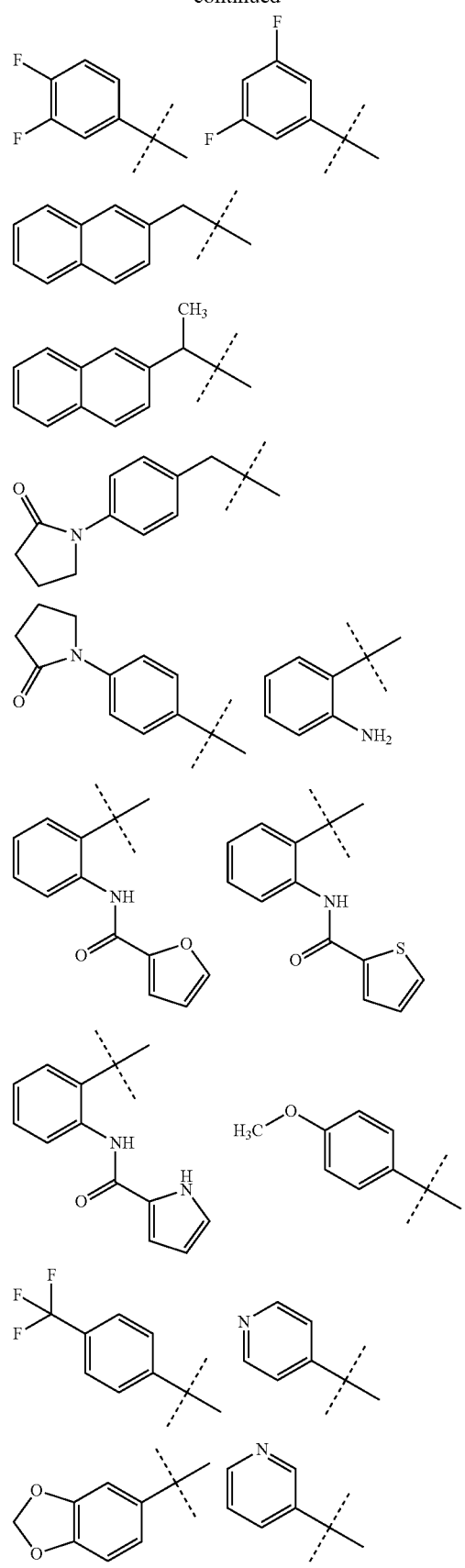

-continued
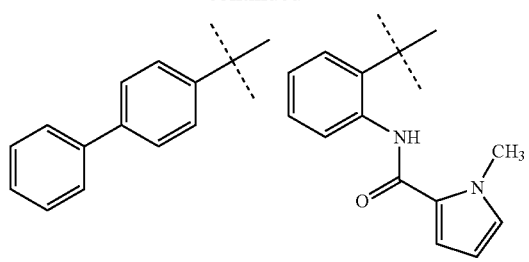
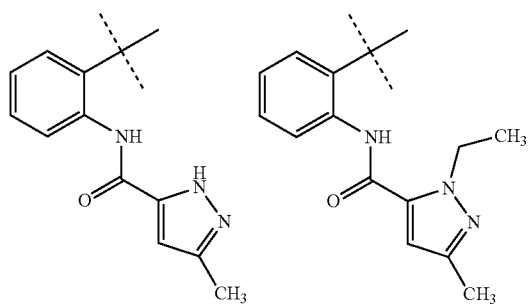
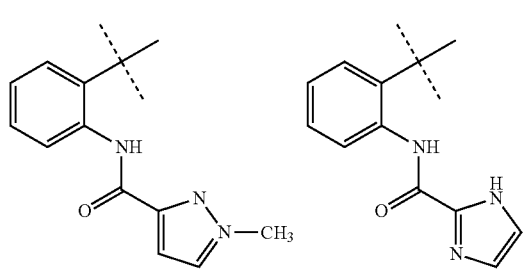
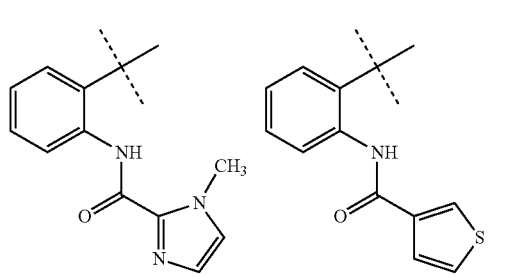
-continued
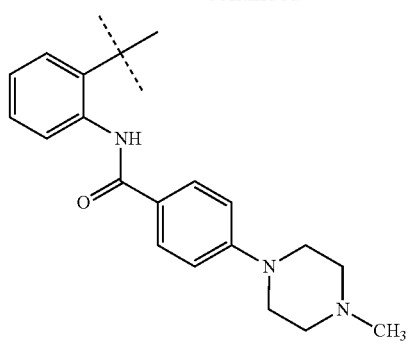
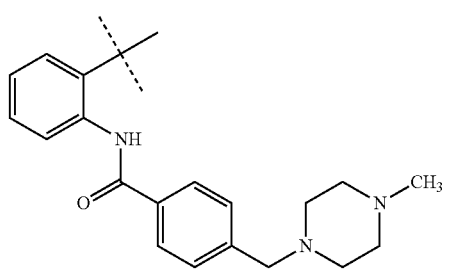
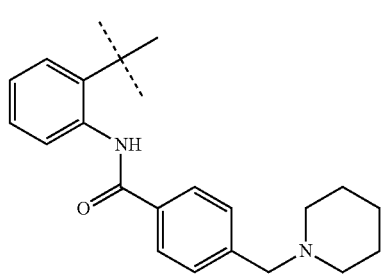
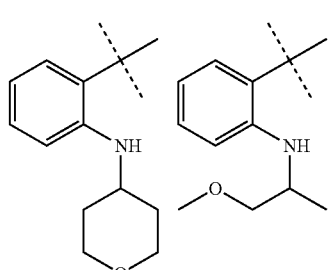
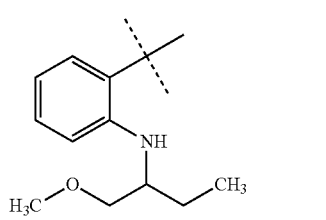
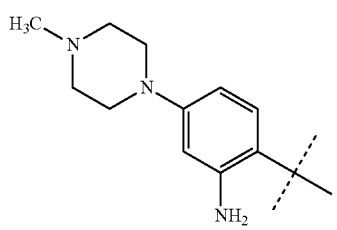

-continued
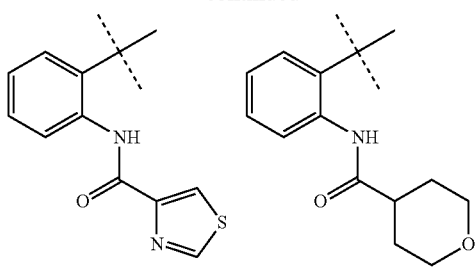
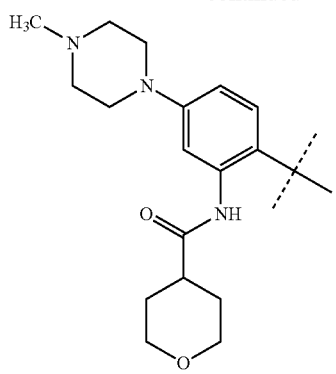
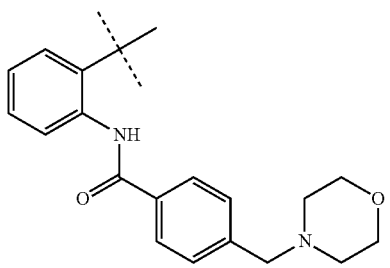
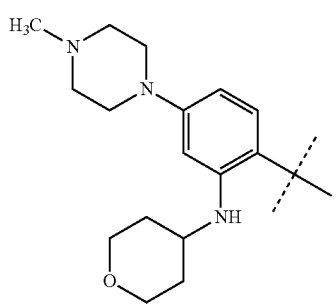
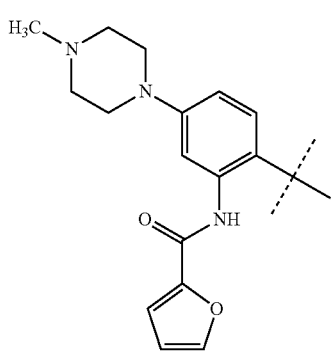
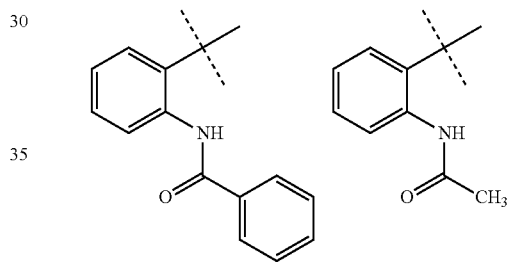
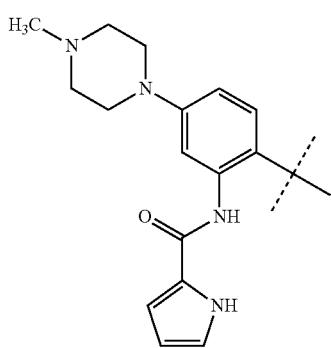
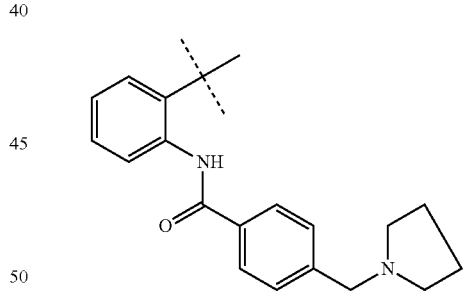
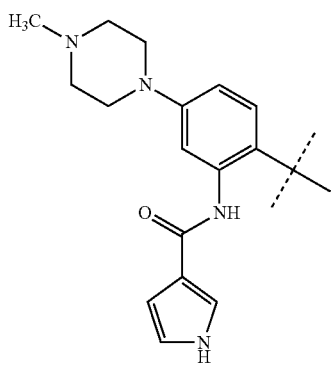
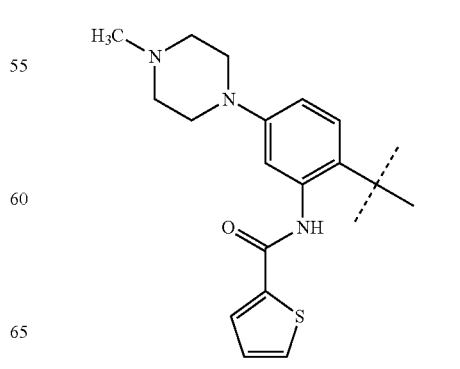

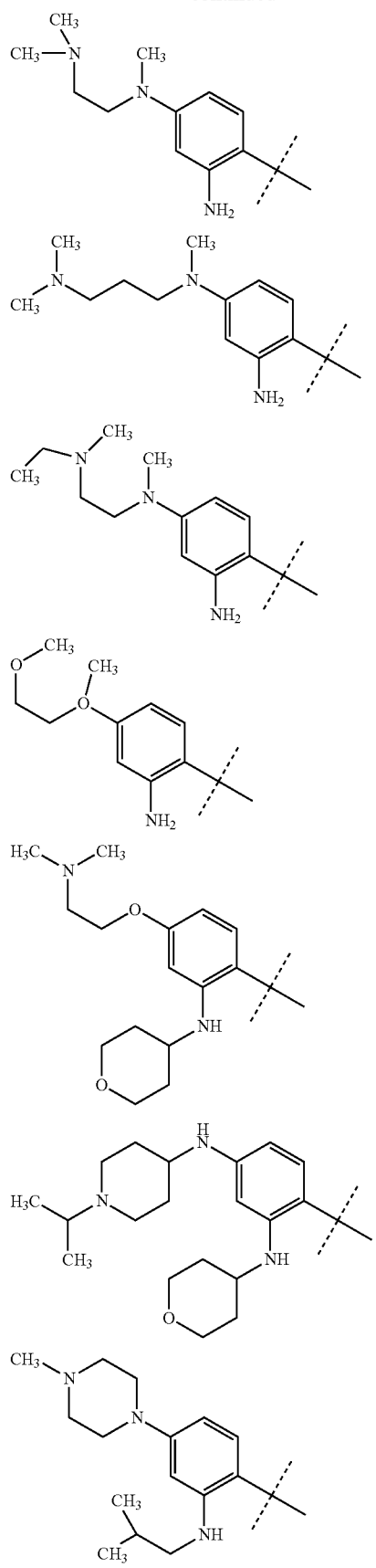
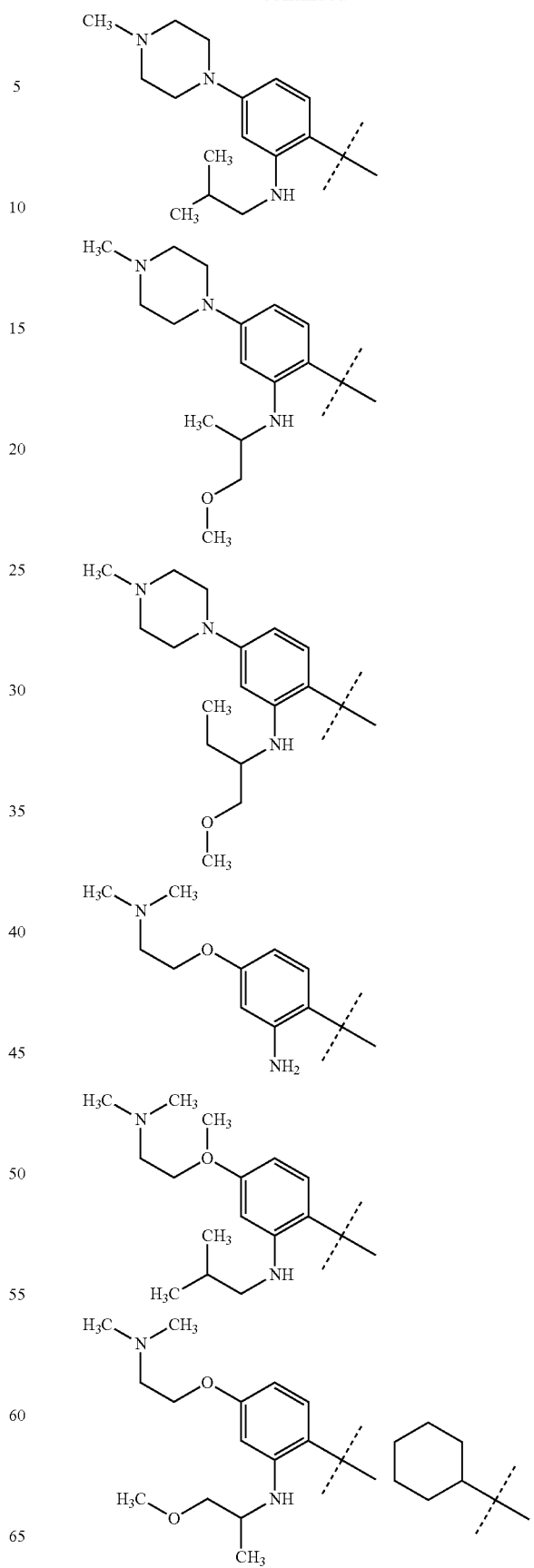

25

-continued

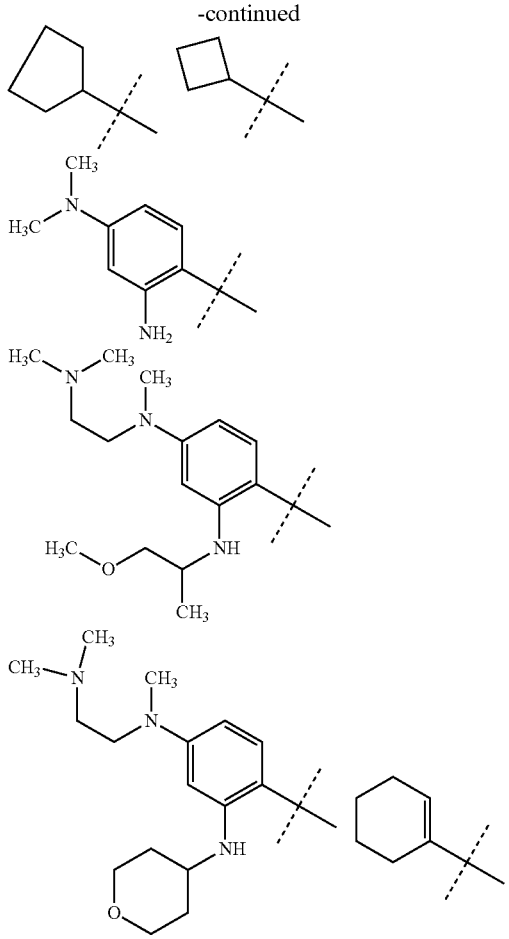

In another preferred aspect, the present invention provides a compound of formula (I$^{iv'}$):

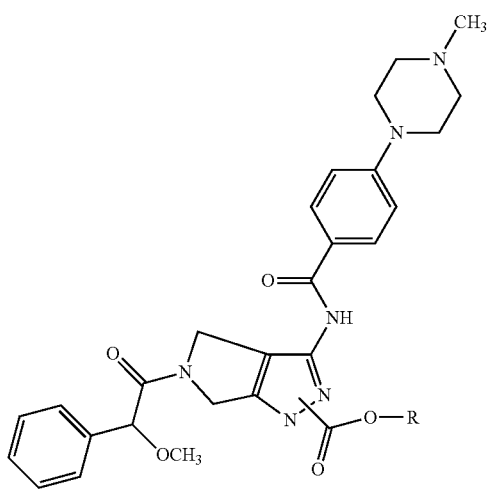

(I$^{iv'}$)

wherein

R is as defined above, or a pharmaceutically acceptable salt thereof, for use as a medicament; more preferably as prodrug, even more preferably as anticancer produg.

26

Preferably, the configuration of the asymmetric carbon atom is (R), and R is selected from methyl, ethyl, cyclopentyl, n-pentyl, t-butyl, 2-propynyl, allyl, benzyl, n-heptyl, neopentyl, n-butyl, iso-butyl, vinyl, 3-chloro-propyl, 3-fluoro-propyl, 2-methoxyethyl, 2-ethoxyethyl, iso-propyl, n-propyl, phenyl, n-hexyl, sec-butyl, isopropenyl or a group of formula:

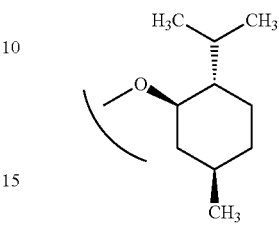

More preferably, the present invention provides a compound of formula (I$^{iv'}$) having (R) configuration and characterized in that R is a ethyl group for use as a medicament; more preferably as prodrug, even more preferably as anticancer produg.

Even more preferably, the present invention provides the compound of the formula:

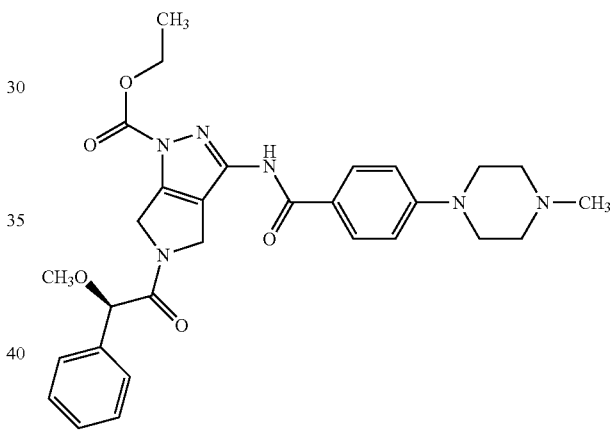

or a pharmaceutically acceptable salt thereof for use as a medicament, preferably as prodrug, even more preferably as prodrug for treating cell proliferative disorders caused by and/or associated with an altered protein kinase activity, in particular as prodrug for treating cancer.

Such compound is coded A024 herein below.

The invention further provides any therapeutic method of treatment using as prod rug the compound coded A024 as defined above.

The present invention also includes pharmaceutical compositions comprising a compound coded A024 as defined above or a pharmaceutically acceptable salt thereof in association with a pharmaceutically acceptable excipient, which may be a carrier or a diluent, and to a method for treating cell proliferative disorders caused by and/or associated with an altered protein kinase activity, which comprises administering to a mammal in need thereof an effective amount of a compound coded A24 as defined above or a pharmaceutical composition as specified herein.

In another aspect, there is provided a compound of formula (I$^{iv'}$) wherein R is a straight or branched $C_1$-$C_{12}$ alkyl, an aryl or heteroaryl group, but not an ethyl group.

Specific, non limiting, examples of compounds of the invention, whenever appropriate in the form of pharmaceutically acceptable salts, as such, for use as medicament or both, are the following:

A01 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid methyl ester;
A02 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid ethyl ester;
A03 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid vinyl ester;
A04 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid propyl ester;
A05 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid isopropyl ester;
A06 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid allyl ester;
A07 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid propargyl ester;
A08 5-(2,6-Diethyl-phenylcarbamoyl)-3-[4-(4-methyl-piperazin-1-1)-benzoylamino]-5,6-dihydro-4H-pyrrolo[3,4-c]pyrazole-1-carboxylic acid butyl ester;
A09 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid isobutyl ester;
A010 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid sec-butyl ester;
A011 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid tert-butyl ester;
A012 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid pentyl ester;
A013 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid neopentyl ester;
A014 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid hexyl ester;
A015 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid heptyl ester;
A016 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid benzyl ester;
A017 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid phenyl ester;
A018 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid 2-methoxyethyl ester;
A019 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid cyclopentyl ester;
A020 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;
A021 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid 2-fluoroethyl ester;
A022 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid 2-chloroethyl ester;
A023 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid methyl ester;
A024 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid ethyl ester;
A025 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid vinyl ester;
A026 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid propyl ester;
A027 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isopropyl ester;
A028 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid allyl ester;
A029 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid propargyl ester;
A030 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid butyl ester;
A031 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid sec-butyl ester;
A032 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isobutyl ester;
A033 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid tert-butyl ester;
A034 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid pentyl ester;
A035 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid neopentyl ester;
A036 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid hexyl ester;
A037 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid heptyl ester;
A038 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid benzyl ester;
A039 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid phenyl ester;
A040 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid cyclopentyl ester;
A041 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-methoxyethyl ester;
A042 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;

A043  5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-fluoroethyl ester;

A044  5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-chloroethyl ester;

B01  5-(1-Methyl-1-phenyl-ethylcarbamoyl)-3-[4-(4-methyl-piperazin-1-ylmethyl)-benzoylamino]-furo[3,2-c]pyrazole-1-carboxylic acid methyl ester;

B02  5-(1-Methyl-1-phenyl-ethylcarbamoyl)-3-[4-(4-methyl-piperazin-1-ylmethyl)-benzoylamino]-furo[3,2-c]pyrazole-1-carboxylic acid ethyl ester;

B03  5-(1-Methyl-1-phenyl-ethylcarbamoyl)-3-[4-(4-methyl-piperazin-1-ylmethyl)-benzoylamino]-furo[3,2-c]pyrazole-1-carboxylic acid vinyl ester;

B04  5-(1-Methyl-1-phenyl-ethylcarbamoyl)-3-[4-(4-methyl-piperazin-1-ylmethyl)-benzoylamino]-furo[3,2-c]pyrazole-1-carboxylic acid propyl ester;

B05  5-(1-Methyl-1-phenyl-ethylcarbamoyl)-3-[4-(4-methyl-piperazin-1-ylmethyl)-benzoylamino]-furo[3,2-c]pyrazole-1-carboxylic acid isopropyl ester;

B06  5-(1-Methyl-1-phenyl-ethylcarbamoyl)-3-[4-(4-methyl-piperazin-1-ylmethyl)-benzoylamino]-furo[3,2-c]pyrazole-1-carboxylic acid allyl ester;

B07  5-(1-Methyl-1-phenyl-ethylcarbamoyl)-3-[4-(4-methyl-piperazin-1-ylmethyl)-benzoylamino]-furo[3,2-c]pyrazole-1-carboxylic acid propargyl ester;

B08  5-(1-Methyl-1-phenyl-ethylcarbamoyl)-3-[4-(4-methyl-piperazin-1-ylmethyl)-benzoylamino]-furo[3,2-c]pyrazole-1-carboxylic acid butyl ester;

B09  5-(1-Methyl-1-phenyl-ethylcarbamoyl)-3-[4-(4-methyl-piperazin-1-ylmethyl)-benzoylamino]-furo[3,2-c]pyrazole-1-carboxylic acid isobutyl ester;

B010  5-(1-Methyl-1-phenyl-ethylcarbamoyl)-3-[4-(4-methyl-piperazin-1-ylmethyl)-benzoylamino]-furo[3,2-c]pyrazole-1-carboxylic acid sec-butyl ester;

B011  5-(1-Methyl-1-phenyl-ethylcarbamoyl)-3-[4-(4-methyl-piperazin-1-ylmethyl)-benzoylamino]-furo[3,2-c]pyrazole-1-carboxylic acid tert-butyl ester;

B012  5-(1-Methyl-1-phenyl-ethylcarbamoyl)-3-[4-(4-methyl-piperazin-1-ylmethyl)-benzoylamino]-furo[3,2-c]pyrazole-1-carboxylic acid pentyl ester;

B013  5-(1-Methyl-1-phenyl-ethylcarbamoyl)-3-[4-(4-methyl-piperazin-1-ylmethyl)-benzoylamino]-furo[3,2-c]pyrazole-1-carboxylic acid neopentyl ester;

B014  5-(1-Methyl-1-phenyl-ethylcarbamoyl)-3-[4-(4-methyl-piperazin-1-ylmethyl)-benzoylamino]-furo[3,2-c]pyrazole-1-carboxylic acid hexyl ester;

B015  5-(1-Methyl-1-phenyl-ethylcarbamoyl)-3-[4-(4-methyl-piperazin-1-ylmethyl)-benzoylamino]-furo[3,2-c]pyrazole-1-carboxylic acid heptyl ester;

B016  5-(1-Methyl-1-phenyl-ethylcarbamoyl)-3-[4-(4-methyl-piperazin-1-ylmethyl)-benzoylamino]-furo[3,2-c]pyrazole-1-carboxylic acid benzyl ester;

B017  5-(1-Methyl-1-phenyl-ethylcarbamoyl)-3-[4-(4-methyl-piperazin-1-ylmethyl)-benzoylamino]-furo[3,2-c]pyrazole-1-carboxylic acid phenyl ester;

B018  5-(1-Methyl-1-phenyl-ethylcarbamoyl)-3-[4-(4-methyl-piperazin-1-ylmethyl)-benzoylamino]-furo[3,2-c]pyrazole-1-carboxylic acid cyclopentyl ester;

B019  5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-methoxyethyl ester;

B020  5-(1-Methyl-1-phenyl-ethylcarbamoyl)-3-[4-(4-methyl-piperazin-1-ylmethyl)-benzoylamino]-furo[3,2-c]pyrazole-1-carboxylic acid (1R,2S,5R)-2-isopropyl-5-methyl-cyclohexyl ester;

B021  5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-fluoroethyl ester;

B022  5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-chloroethyl ester;

B023  5-(1-Methyl-1-phenyl-ethylcarbamoyl)-3-(4-pyrrolidin-1-ylmethyl-benzoylamino)-furo[3,2-c]pyrazole-1-carboxylic acid methyl ester;

B024  5-(1-Methyl-1-phenyl-ethylcarbamoyl)-3-(4-pyrrolidin-1-ylmethyl-benzoylamino)-furo[3,2-c]pyrazole-1-carboxylic acid ethyl ester;

B025  5-(1-Methyl-1-phenyl-ethylcarbamoyl)-3-(4-pyrrolidin-1-ylmethyl-benzoylamino)-furo[3,2-c]pyrazole-1-carboxylic acid vinyl ester;

B026  5-(1-Methyl-1-phenyl-ethylcarbamoyl)-3-(4-pyrrolidin-1-ylmethyl-benzoylamino)-furo[3,2-c]pyrazole-1-carboxylic acid propyl ester;

B027  5-(1-Methyl-1-phenyl-ethylcarbamoyl)-3-(4-pyrrolidin-1-ylmethyl-benzoylamino)-furo[3,2-c]pyrazole-1-carboxylic acid isopropyl ester;

B028  5-(1-Methyl-1-phenyl-ethylcarbamoyl)-3-(4-pyrrolidin-1-ylmethyl-benzoylamino)-furo[3,2-c]pyrazole-1-carboxylic acid allyl ester;

B029  5-(1-Methyl-1-phenyl-ethylcarbamoyl)-3-(4-pyrrolidin-1-ylmethyl-benzoylamino)-furo[3,2-c]pyrazole-1-carboxylic acid propargyl ester;

B030  5-(1-Methyl-1-phenyl-ethylcarbamoyl)-3-(4-pyrrolidin-1-ylmethyl-benzoylamino)-furo[3,2-c]pyrazole-1-carboxylic acid butyl ester;

B031  5-(1-Methyl-1-phenyl-ethylcarbamoyl)-3-(4-pyrrolidin-1-ylmethyl-benzoylamino)-furo[3,2-c]pyrazole-1-carboxylic acid isobutyl ester;

B032-phenyl-ethylcarbamoyl)-3-(4-pyrrolidin-1-ylmethyl-benzoylamino)-furo[3,2-c]pyrazole-1-carboxylic acid sec-butyl ester;

B033-phenyl-ethylcarbamoyl)-3-(4-pyrrolidin-1-ylmethyl-benzoylamino)-furo[3,2-c]pyrazole-1-carboxylic acid tert-butyl ester;

B034  5-(1-Methyl-1-phenyl-ethylcarbamoyl)-3-(4-pyrrolidin-1-ylmethyl-benzoylamino)-furo[3,2-c]pyrazole-1-carboxylic acid pentyl ester;

B035  phenyl-ethylcarbamoyl)-3-(4-pyrrolidin-1-ylmethyl-benzoylamino)-furo[3,2-c]pyrazole-1-carboxylic acid neopentyl ester;

B036  5-(1-Methyl-1-phenyl-ethylcarbamoyl)-3-(4-pyrrolidin-1-ylmethyl-benzoylamino)-furo[3,2-c]pyrazole-1-carboxylic acid hexyl ester;

B037  5-(1-Methyl-1-phenyl-ethylcarbamoyl)-3-(4-pyrrolidin-1-ylmethyl-benzoylamino)-furo[3,2-c]pyrazole-1-carboxylic acid heptyl ester;

B038  5-(1-Methyl-1-phenyl-ethylcarbamoyl)-3-(4-pyrrolidin-1-ylmethyl-benzoylamino)-furo[3,2-c]pyrazole-1-carboxylic acid benzyl ester;

B039  5-(1-Methyl-1-phenyl-ethylcarbamoyl)-3-(4-pyrrolidin-1-ylmethyl-benzoylamino)-furo[3,2-c]pyrazole-1-carboxylic acid phenyl ester;

B040  5-(1-Methyl-1-phenyl-ethylcarbamoyl)-3-(4-pyrrolidin-1-ylmethyl-benzoylamino)-furo[3,2-c]pyrazole-1-carboxylic acid cyclopentyl ester;

B041  5-(1-Methyl-1-phenyl-ethylcarbamoyl)-3-(4-pyrrolidin-1-ylmethyl-benzoylamino)-furo[3,2-c]pyrazole-1-carboxylic acid 2-methoxyethyl ester;

B042  5-(1-Methyl-1-phenyl-ethylcarbamoyl)-3-(4-pyrrolidin-1-ylmethyl-benzoylamino)-furo[3,2-c]pyrazole-1-carboxylic acid (1R,2S,5R)-2-isopropyl-5-methyl-cyclohexyl ester;

B043 5-(1-Methyl-1-phenyl-ethylcarbamoyl)-3-(4-pyrrolidin-1-ylmethyl-benzoylamino)-furo[3,2-c]pyrazole-1-carboxylic acid 2-fluoroethyl ester;

B044 5-(1-Methyl-1-phenyl-ethylcarbamoyl)-3-(4-pyrrolidin-1-ylmethyl-benzoylamino)-furo[3,2-c]pyrazole-1-carboxylic acid 2-chloroethyl ester;

B045 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid methyl ester;

B046 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid ethyl ester;

B047 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid vinyl ester;

B048 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid propyl ester;

B049 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid isopropyl ester;

B050 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid allyl ester;

B051 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid propargyl ester;

B052 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid butyl ester;

B053 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid isobutyl ester;

B054-phenyl-ethylcarbamoyl)-3-{2-[(2-methyl-2H-pyrazole-3-carbonyl)-amino]-benzoylamino}-furo[3,2-c]pyrazole-1-carboxylic acid sec-butyl ester;

B055-phenyl-ethylcarbamoyl)-3-{2-[(2-methyl-2H-pyrazole-3-carbonyl)-amino]-benzoylamino}-furo[3,2-c]pyrazole-1-carboxylic acid tert-butyl ester;

B056-phenyl-ethylcarbamoyl)-3-{2-[(2-methyl-2H-pyrazole-3-carbonyl)-amino]-benzoylamino}-furo[3,2-c]pyrazole-1-carboxylic acid pentyl ester;

B057-phenyl-ethylcarbamoyl)-3-{2-[(2-methyl-2H-pyrazole-3-carbonyl)-amino]-benzoylamino}-furo[3,2-c]pyrazole-1-carboxylic acid neopentyl ester;

B058 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid hexyl ester;

B059-phenyl-ethylcarbamoyl)-3-{2-[(2-methyl-2H-pyrazole-3-carbonyl)-amino]-benzoylamino}-furo[3,2-c]pyrazole-1-carboxylic acid heptyl ester;

B060 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid benzyl ester;

B061 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid phenyl ester;

B062 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid cyclopentyl ester;

B063 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid 2-methoxyethyl ester;

B064 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid (1R,2S,5R)-2-isopropyl-5-methyl-cyclohexyl ester;

B065 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid 2-fluoroethyl ester;

B066 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid 2-chloroethyl ester;

B067 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid methyl ester;

B068 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid ethyl ester;

B069 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid vinyl ester;

B070 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid propyl ester;

B071 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid isopropyl ester;

B072 5-(1-Methyl-1-phenyl-ethyl carbamoyl)-3-{2-[(1-methyl-1H-pyrrole-2-carbonyl)-amino]-benzoylamino}-furo[3,2-c]pyrazole-1-carboxylic acid allyl ester;

B073 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid propargyl ester;

B074 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid butyl ester;

B075 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid isobutyl ester;

B076 5-phenyl-ethylcarbamoyl)-3-{2-[(1-methyl-1H-pyrrole-2-carbonyl)-amino]-benzoylamino}-furo[3,2-c]pyrazole-1-carboxylic acid sec-butyl ester;

B077 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid tert-butyl ester;

B078 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid pentyl ester;

B079 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid neopentyl ester;

B080-phenyl-ethylcarbamoyl)-3-{2-[(1-methyl-1H-pyrrole-2-carbonyl)-amino]-benzoylamino}-furo[3,2-c]pyrazole-1-carboxylic acid hexyl ester;

B081-phenyl-ethylcarbamoyl)-3-{2-[(1-methyl-1H-pyrrole-2-carbonyl)-amino]-benzoylamino}-furo[3,2-c]pyrazole-1-carboxylic acid heptyl ester;

B082 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid benzyl ester;

B083 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid phenyl ester;

B084 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid 2-methoxyethyl ester;

B085 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid cyclopentyl ester;

B086 5-(1-Methyl-1-phenyl-ethylcarbamoyl)-3-{2-[(1-methyl-1H-pyrrole-2-carbonyl)-amino]-benzoylamino}-furo

[3,2-c]pyrazole-1-carboxylic acid (1R,2S,5R)-2-isopropyl-5-methyl-cyclohexyl ester;

B087 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid 2-fluoroethyl ester;

B088 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid 2-chloroethyl ester;

C01 5-(1-Methyl-1-phenyl-ethylcarbamoyl)-3-(4-piperidin-1-ylmethyl-benzoylamino)-thieno[2,3-c]pyrazole-1-carboxylic acid methyl ester;

C02 5-(1-Methyl-1-phenyl-ethylcarbamoyl)-3-(4-piperidin-1-ylmethyl-benzoylamino)-thieno[2,3-c]pyrazole-1-carboxylic acid ethyl ester;

C03 5-(1-Methyl-1-phenyl-ethylcarbamoyl)-3-(4-piperidin-1-ylmethyl-benzoylamino)-thieno[2,3-c]pyrazole-1-carboxylic acid vinyl ester;

C04 5-(1-Methyl-1-phenyl-ethylcarbamoyl)-3-(4-piperidin-1-ylmethyl-benzoylamino)-thieno[2,3-c]pyrazole-1-carboxylic acid propyl ester;

C05 5-(1-Methyl-1-phenyl-ethylcarbamoyl)-3-(4-piperidin-1-ylmethyl-benzoylamino)-thieno[2,3-c]pyrazole-1-carboxylic acid isopropyl ester;

C06 5-(1-Methyl-1-phenyl-ethylcarbamoyl)-3-(4-piperidin-1-ylmethyl-benzoylamino)-thieno[2,3-c]pyrazole-1-carboxylic acid allyl ester;

C07 5-(1-Methyl-1-phenyl-ethylcarbamoyl)-3-(4-piperidin-1-ylmethyl-benzoylamino)-thieno[2,3-c]pyrazole-1-carboxylic acid propargyl ester;

C08 5-(1-Methyl-1-phenyl-ethylcarbamoyl)-3-(4-piperidin-1-ylmethyl-benzoylamino)-thieno[2,3-c]pyrazole-1-carboxylic acid butyl ester;

C09 5-(1-Methyl-1-phenyl-ethylcarbamoyl)-3-(4-piperidin-1-ylmethyl-benzoylamino)-thieno[2,3-c]pyrazole-1-carboxylic acid isobutyl ester;

C010 5-(1-Methyl-1-phenyl-ethylcarbamoyl)-3-(4-piperidin-1-ylmethyl-benzoylamino)-thieno[2,3-c]pyrazole-1-carboxylic acid sec-butyl ester;

C011-phenyl-ethylcarbamoyl)-3-(4-piperidin-1-ylmethyl-benzoylamino)-thieno[2,3-c]pyrazole-1-carboxylic acid tert-butyl ester;

C012 5-(1-Methyl-1-phenyl-ethylcarbamoyl)-3-(4-piperidin-1-ylmethyl-benzoylamino)-thieno[2,3-c]pyrazole-1-carboxylic acid pentyl ester;

C013-phenyl-ethylcarbamoyl)-3-(4-piperidin-1-ylmethyl-benzoylamino)-thieno[2,3-c]pyrazole-1-carboxylic acid neopentyl ester;

C014 5-(1-Methyl-1-phenyl-ethylcarbamoyl)-3-(4-piperidin-1-ylmethyl-benzoylamino)-thieno[2,3-c]pyrazole-1-carboxylic acid hexyl ester;

C015-phenyl-ethylcarbamoyl)-3-(4-piperidin-1-ylmethyl-benzoylamino)-thieno[2,3-c]pyrazole-1-carboxylic acid heptyl ester;

C016 5-(1-Methyl-1-phenyl-ethylcarbamoyl)-3-(4-piperidin-1-ylmethyl-benzoylamino)-thieno[2,3-c]pyrazole-1-carboxylic acid benzyl ester;

C017 5-(1-Methyl-1-phenyl-ethylcarbamoyl)-3-(4-piperidin-1-ylmethyl-benzoylamino)-thieno[2,3-c]pyrazole-1-carboxylic acid phenyl ester;

C018-phenyl-ethylcarbamoyl)-3-(4-piperidin-1-ylmethyl-benzoylamino)-thieno[2,3-c]pyrazole-1-carboxylic acid cyclopentyl ester;

C019 5-(1-Methyl-1-phenyl-ethylcarbamoyl)-3-(4-piperidin-1-ylmethyl-benzoylamino)-thieno[2,3-c]pyrazole-1-carboxylic acid 2-methoxyethyl ester;

C020 5-(1-Methyl-1-phenyl-ethylcarbamoyl)-3-(4-piperidin-1-ylmethyl-benzoylamino)-thieno[2,3-c]pyrazole-1-carboxylic acid (1R,2S,5R)-2-isopropyl-5-methyl-cyclohexyl ester;

C021 5-(1-Methyl-1-phenyl-ethylcarbamoyl)-3-(4-piperidin-1-ylmethyl-benzoylamino)-thieno[2,3-c]pyrazole-1-carboxylic acid 2-fluoroyethyl ester;

C022 5-(1-Methyl-1-phenyl-ethylcarbamoyl)-3-(4-piperidin-1-ylmethyl-benzoylamino)-thieno[2,3-c]pyrazole-1-carboxylic acid 2-chloroethyl ester;

C023 5-(1-Menthyl-phenyl-ethylcarbamoyl)-3-(4-morpholin-4-yl-benzoylamino)-thieno[2,3-c]pyrazole-1-carboxylic acid methyl ester;

C024 5-(1-Methyl-1-phenyl-ethylcarbamoyl)-3-(4-morpholin-4-yl-benzoylamino)-thieno[2,3-c]pyrazole-1-carboxylic acid ethyl ester;

C025 5-(1-Methyl-1-phenyl-ethylcarbamoyl)-3-(4-morpholin-4-yl-benzoylamino)-thieno[2,3-c]pyrazole-1-carboxylic acid vinyl ester;

C026 5-(1-Methyl-1-phenyl-ethylcarbamoyl)-3-(4-morpholin-4-yl-benzoylamino)-thieno[2,3-c]pyrazole-1-carboxylic acid propyl ester;

C027 5-(1-Methyl-1-phenyl-ethylcarbamoyl)-3-(4-morpholin-4-yl-benzoylamino)-thieno[2,3-c]pyrazole-1-carboxylic acid allyl ester;

C028-phenyl-ethylcarbamoyl)-3-(4-morpholin-4-yl-benzoylamino)-thieno[2,3-c]pyrazole-1-carboxylic acid propargyl ester;

C029 5-(1-Methyl-1-phenyl-ethyl carbamoyl)-3-(4-morpholin-4-yl-benzoylamino)-thieno[2,3-c]pyrazole-1-carboxylic acid isopropyl ester;

C030 5-(1-Methyl-1-phenyl-ethylcarbamoyl)-3-(4-morpholin-4-yl-benzoylamino)-thieno[2,3-c]pyrazole-1-carboxylic acid butyl ester;

C031 5-(1-Methyl-1-phenyl-ethylcarbamoyl)-3-(4-morpholin-4-yl-benzoylamino)-thieno[2,3-c]pyrazole-1-carboxylic acid isobutyl ester;

C032 5-(1-Methyl-1-phenyl-ethylcarbamoyl)-3-(4-morpholin-4-yl-benzoylamino)-thieno[2,3-c]pyrazole-1-carboxylic acid sec-butyl ester;

C033 5-(1-Methyl-1-phenyl-ethylcarbamoyl)-3-(4-morpholin-4-yl-benzoylamino)-thieno[2,3-c]pyrazole-1-carboxylic acid tert-butyl ester;

C034 5-(1-Methyl-1-phenyl-ethylcarbamoyl)-3-(4-morpholin-4-yl-benzoylamino)-thieno[2,3-c]pyrazole-1-carboxylic acid pentyl ester;

C035 5-(1-Methyl-1-phenyl-ethylcarbamoyl)-3-(4-morpholin-4-yl-benzoylamino)-thieno[2,3-c]pyrazole-1-carboxylic acid neopentyl ester;

C036 5-(1-Methyl-1-phenyl-ethylcarbamoyl)-3-(4-morpholin-4-yl-benzoylamino)-thieno[2,3-c]pyrazole-1-carboxylic acid hexyl ester;

C037 5-(1-Methyl-1-phenyl-ethylcarbamoyl)-3-(4-morpholin-4-yl-benzoylamino)-thieno[2,3-c]pyrazole-1-carboxylic acid heptyl ester;

C038 5-(1-Methyl-1-phenyl-ethylcarbamoyl)-3-(4-morpholin-4-yl-benzoylamino)-thieno[2,3-c]pyrazole-1-carboxylic acid benzyl ester;

C039 5-(1-Methyl-1-phenyl-ethylcarbamoyl)-3-(4-morpholin-4-yl-benzoylamino)-thieno[2,3-c]pyrazole-1-carboxylic acid phenyl ester;

C040 5-(1-Methyl-1-phenyl-ethylcarbamoyl)-3-(4-morpholin-4-yl-benzoylamino)-thieno[2,3-c]pyrazole-1-carboxylic acid 2-methoxyethyl ester;

C041 5-(1-Methyl-1-phenyl-ethylcarbamoyl)-3-(4-morpholin-4-yl-benzoylamino)-thieno[2,3-c]pyrazole-1-carboxylic acid cyclopentyl ester;

C042 5-(1-Methyl-1-phenyl-ethylcarbamoyl)-3-(4-morpholin-4-yl-benzoylamino)-thieno[2,3-c]pyrazole-1-carboxylic acid (1R,2S,5R)-2-isopropyl-5-methyl-cyclohexyl ester;
C043 5-(1-Methyl-1-phenyl-ethylcarbamoyl)-3-(4-morpholin-4-yl-benzoylamino)-thieno[2,3-c]pyrazole-1-carboxylic acid 2-fluoroethyl ester;
C044 5-(1-Methyl-1-phenyl-ethylcarbamoyl)-3-(4-morpholin-4-yl-benzoylamino)-thieno[2,3-c]pyrazole-1-carboxylic acid 2-chloroethyl ester;
C045 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid methyl ester;
C046 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid ethyl ester;
C047 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid vinyl ester;
C048 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid propyl ester;
C049 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid isopropyl ester;
C050 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid allyl ester;
C051 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid propargyl ester;
C052 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid butyl ester;
C053 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid isobutyl ester;
C054 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid sec-butyl ester;
C055 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid tert-butyl ester;
C056 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid pentyl ester;
C057 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid neopentyl ester;
C058 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid hexyl ester;
C059 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid heptyl ester;
C060 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid benzyl ester;
C061 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid phenyl ester;
C062-phenyl-ethylcarbamoyl)-3-[4-(4-methyl-piperazin-1-ylmethyl)-benzoylamino]-thieno[2,3-c]pyrazole-1-carboxylic acid 2-methoxyethyl ester;
C063 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid cyclopentyl ester;
C064 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid (1R,2S,5R)-2-isopropyl-5-methyl-cyclohexyl ester;
C065 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid 2-fluoroethyl ester;
C066 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid 2-chloroethyl ester;
C067 3-[4-(Isopropylamino-methyl)-benzoylamino]-5-(1-methyl-1-phenyl-ethylcarbamoyl)-thieno[2,3-c]pyrazole-1-carboxylic acid methyl ester;
C068 3-[4-(Isopropylamino-methyl)-benzoylamino]-5-(1-methyl-1-phenyl-ethylcarbamoyl)-thieno[2,3-c]pyrazole-1-carboxylic acid ethyl ester;
C069 3-[4-(Isopropylamino-methyl)-benzoylamino]-5-(1-methyl-1-phenyl-ethylcarbamoyl)-thieno[2,3-c]pyrazole-1-carboxylic acid vinyl ester;
C070 3-[4-(Isopropylamino-methyl)-benzoylamino]-5-(1-methyl-1-phenyl-ethylcarbamoyl)-thieno[2,3-c]pyrazole-1-carboxylic acid propyl ester;
C071 3-[4-(Isopropylamino-methyl)-benzoylamino]-5-(1-methyl-1-phenyl-ethylcarbamoyl)-thieno[2,3-c]pyrazole-1-carboxylic acid isopropyl ester;
C072 3-[4-(Isopropylamino-methyl)-benzoylamino]-5-(1-methyl-1-phenyl-ethylcarbamoyl)-thieno[2,3-c]pyrazole-1-carboxylic acid allyl ester;
C073 3-[4-(Isopropylamino-methyl)-benzoylamino]-5-(1-methyl-1-phenyl-ethylcarbamoyl)-thieno[2,3-c]pyrazole-1-carboxylic acid propargyl ester;
C074 3-[4-(Isopropylamino-methyl)-benzoylamino]-5-(1-methyl-1-phenyl-ethylcarbamoyl)-thieno[2,3-c]pyrazole-1-carboxylic acid butyl ester;
C075 3-[4-(Isopropylamino-methyl)-benzoylamino]-5-(1-methyl-1-phenyl-ethylcarbamoyl)-thieno[2,3-c]pyrazole-1-carboxylic acid isobutyl ester;
C076 3-[4-(Isopropylamino-methyl)-benzoylamino]-5-(1-methyl-1-phenyl-ethylcarbamoyl)-thieno[2,3-c]pyrazole-1-carboxylic acid sec-butyl ester;
C077 3-[4-(Isopropylamino-methyl)-benzoylamino]-5-(1-methyl-1-phenyl-ethylcarbamoyl)-thieno[2,3-c]pyrazole-1-carboxylic acid tert-butyl ester;
C078 3-[4-(Isopropylamino-methyl)-benzoylamino]-5-(1-methyl-1-phenyl-ethyl carbamoyl)-thieno[2,3-c]pyrazole-1-carboxylic acid pentyl ester;
C079 3-[4-(Isopropylamino-methyl)-benzoylamino]-5-(1-methyl-1-phenyl-ethylcarbamoyl)-thieno[2,3-c]pyrazole-1-carboxylic acid neopentyl ester;
C080 3-[4-(Isopropylamino-methyl)-benzoylamino]-5-(1-methyl-1-phenyl-ethylcarbamoyl)-thieno[2,3-c]pyrazole-1-carboxylic acid hexyl ester;
C081 3-[4-(isopropylamino-methyl)-benzoylamino]-5-(1-methyl-1-phenyl-ethylcarbamoyl)-thieno[2,3-c]pyrazole-1-carboxylic acid heptyl ester;
C082 3-[4-(Isopropylamino-methyl)-benzoylamino]-5-(1-methyl-1-phenyl-ethylcarbamoyl)-thieno[2,3-c]pyrazole-1-carboxylic acid benzyl ester;
C083 3-[4-(Isopropylamino-methyl)-benzoylamino]-5-(1-methyl-1-phenyl-ethylcarbamoyl)-thieno[2,3-c]pyrazole-1-carboxylic acid phenyl ester;
C084 3-[4-(Isopropylamino-methyl)-benzoylamino]-5-(1-methyl-1-phenyl-ethylcarbamoyl)-thieno[2,3-c]pyrazole-1-carboxylic acid cyclopentyl ester;
C085 3-[4-(Isopropylamino-methyl)-benzoylamino]-5-(1-methyl-1-phenyl-ethylcarbamoyl)-thieno[2,3-c]pyrazole-1-carboxylic acid 2-methoxyethyl ester;

C086 3-[4-(Isopropylamino-methyl)-benzoylamino]-5-(1-methyl-1-phenyl-ethylcarbamoyl)-thieno[2,3-c]pyrazole-1-carboxylic acid (1R,2S,5R)-2-isopropyl-5-methyl-cyclohexyl ester;

C087 3-[4-(Isopropylamino-methyl)-benzoylamino]-5-(1-methyl-1-phenyl-ethylcarbamoyl)-thieno[2,3-c]pyrazole-1-carboxylic acid 2-fluoroethyl ester;

C088 3-[4-(Isopropylamino-methyl)-benzoylamino]-5-(1-methyl-1-phenyl-ethylcarbamoyl)-thieno[2,3-c]pyrazole-1-carboxylic acid 2-chloroethyl ester;

C089 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid methyl ester;

C090 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid ethyl ester;

C091 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid vinyl ester;

C092 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid propyl ester;

C093 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid isopropyl ester;

C094 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid propargyl ester;

C095 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid allyl ester;

C096 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid butyl ester;

C097 5-[1-(2-Chloro-phenyl)-1-methyl-ethylcarbamoyl]-3-(4-piperidin-1-ylmethyl-benzoylamino)-thieno[2,3-c]pyrazole-1-carboxyl is acid isobutyl ester;

C098 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid sec-butyl ester;

C099 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid tert-butyl ester;

C0100 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid pentyl ester;

C0101 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid neopentyl ester;

C0102 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid hexyl ester;

C0103 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid heptyl ester;

C0104 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid benzyl ester;

C0105 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid phenyl ester;

C0106 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid cyclopentyl ester;

C0107 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid 2-methoxyethyl ester;

C0108 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid (1R,2S,5R)-2-isopropyl-5-methyl-cyclohexyl ester;

C0109 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid 2-fluoroethyl ester;

C0110 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid 2-chloroethyl ester;

C0111 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid methyl ester;

C0112 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid ethyl ester;

C0113 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid vinyl ester;

C0114 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid propyl ester;

C0115 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid isopropyl ester;

C0116 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid allyl ester;

C0117 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid propargyl ester;

C0118 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid butyl ester;

C0119 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid sec-butyl ester;

C0120 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid isobutyl ester;

C0121 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid tert-butyl ester;

C0122 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid pentyl ester;

C0123 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid neopentyl ester;

C0124 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid hexyl ester;

C0125 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid heptyl ester;

C0126 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid benzyl ester;

C0127 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid phenyl ester;

C0128 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid cyclopentyl ester;

C0129 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid 2-methoxyethyl ester;

C0130 5-[1-(2-Fluoro-phenyl)-1-methyl-ethylcarbamoyl]-3-(4-morpholin-4-ylmethyl-benzoylamino)-thieno[2,3-e]pyrazole-1-carboxylic acid (1R,2S,5R)-2-isopropyl-5-methyl-cyclohexyl ester;

C0131 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid 2-fluoroethyl ester;

C0132 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid 2-chloroethyl ester;

C0133 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid methyl ester;

C0134 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid ethyl ester;

C0135 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid vinyl ester;

C0136 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid propyl ester;

C0137 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid isopropyl ester;

C0138 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid allyl ester;

C0139 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid propargyl ester;

C0140 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid butyl ester;

C0141 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid isobutyl ester;

C0142 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid sec-butyl ester;

C0143 3-{2-[(1-Methyl-1H-imidazole-2-carbonyl)-amino]-benzoylamino}-5-(1-methyl-1-phenyl-ethylcarbamoyl)-thieno[2,3-e]pyrazole-1-carboxylic acid tert-butyl ester;

C0144 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid pentyl ester;

C0145 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid neopentyl ester;

C0146 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid hexyl ester;

C0147 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid heptyl ester;

C0148 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid benzyl ester;

C0149 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid phenyl ester;

C0150 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid 2-methoxyethyl ester;

C0151 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid cyclopentyl ester;

C0152 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid (1R,2S,5R)-2-isopropyl-5-methyl-cyclohexyl ester;

C0153 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid 2-fluoroethyl ester;

C0154 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid 2-chloroethyl ester;

C0155 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid methyl ester;

C0156 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid ethyl ester;

C0157 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid vinyl ester;

C0158 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid propyl ester;

C0159 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid isopropyl ester;

C0160 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid allyl ester;

C0161 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid propargyl ester;

C0162 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid butyl ester;

C0163 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid isobutyl ester;

C0164 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid sec-butyl ester;

C0165 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid tert-butyl ester;

C0166 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid pentyl ester;

C0167 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid neopentyl ester;

C0168 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid hexyl ester;

C0169 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid heptyl ester;

C0170 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid benzyl ester;

C0171 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid phenyl ester;

C0172 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid cyclopentyl ester;

C0173 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid 2-methoxyethyl ester;

C0174 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid (1R,2S,5R)-2-isopropyl-5-methyl-cyclohexyl ester;

C0175 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid 2-fluoroethyl ester;

C0176 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid 2-chloroethyl ester;

C0177 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid methyl ester;

C0178 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid ethyl ester;

C0179 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid vinyl ester;

C0180 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid propyl ester;

C0181-phenyl-ethylcarbamoyl)-3-{2-[(1H-pyrrole-3-carbonyl)-amino]-benzoylamino}-thieno[2,3-c]pyrazole-1-carboxylic acid isopropyl ester;

C0182 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid allyl ester;

C0183 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid propargyl ester;

C0184 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid butyl ester;

C0185 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid isobutyl ester;

C0186 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid sec-butyl ester;

C0187 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid tert-butyl ester;

C0188 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid pentyl ester;

C0189 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid neopentyl ester;

C0190 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid hexyl ester;

C0191 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid heptyl ester;

C0192 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid heptyl ester;

C0193 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid benzyl ester;

C0194 5-(1-Methyl-1-phenyl-ethyl carbamoyl)-3-{2-[(1H-pyrrole-3-carbonyl)-amino]-benzoylamino}-thieno[2,3-c]pyrazole-1-carboxylic acid cyclopentyl ester;

C0195 5-(1-Methyl-1-phenyl-ethyl carbamoyl)-3-{2-[(1H-pyrrole-3-carbonyl)-amino]-benzoylamino}-thieno[2,3-c]pyrazole-1-carboxylic acid 2-methoxyethyl ester;

C0196 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid (1R,2S,5R)-2-isopropyl-5-methyl-cyclohexyl ester;

C0197 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid 2-fluoroethyl ester;

C0198 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid 2-chloroethyl ester;

D01 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid methyl ester;

D02 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid ethyl ester;

D03 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-methoxy-ethyl ester;

D04 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-ethoxy-ethyl ester;

C05 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-(2-methoxy-ethoxy)-ethyl ester;

D06 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D07 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D08 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid 2-methoxy-ethyl ester;

D09 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid 2-ethoxy-ethyl ester;

D010 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid 2-(2-methoxy-ethoxy)-ethyl ester;

D011 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D012 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D013 5-(3,5-Difluoro-benzenesulfonyl)-3-[4-[(2-dimethylamino-propyl)-methyl-amino]-2-(tetrahydro-pyran-4- ylamino)-benzoylamino]-4,5,6,7-tetrahydro-pyrazolo[4,3-c]pyridine-1-carboxylic acid 2-methoxy-ethyl ester;
D014 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid 2-ethoxy-ethyl ester;
D015 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid 2-(2-methoxy-ethoxy)-ethyl ester;
D016 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid methyl ester;
D017 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid ethyl ester;
D018 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid propyl ester;
D019 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid ispropyl ester;
D020 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid methyl ester;
D021 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid ethyl ester;
D022 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid 2-methoxy-ethyl ester;
D023 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid 2-ethoxy-ethyl ester;
D024 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid methyl ester;
D025 5-(3,5-Difluoro-benzenesulfonyl)-3-[4-(pyrrolidin-1-ylmethyl)-2-(tetrahydro-pyren-4-ylamino)-benzoylamino]-4,5,6,7-tetrahydro-pyrazolo[4,3-c]pyridine-1-carboxylic acid ethyl ester;
D026 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid propyl ester;
D027 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid isopropyl ester;
D028 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid methyl ester;
D029 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid ethyl ester;
D030 5-(3,5-Difluoro-benzenesulfonyl)-3-[4-(4-methyl-piperazin-1-yl)-2-(2-methoxy-ethylamino)-benzoylamino]-4,5,6,7-tetrahydro-pyrazolo[4,3-c]pyridine-1-carboxylic acid 2-methoxy-ethyl ester;
D031 5-(3,5-Difluoro-benzenesulfonyl)-3-[4-(4-methyl-piperazin-1-yl)-2-(2-methoxy-ethylamino)-benzoylamino]-4,5,6,7-tetrahydro-pyrazolo[4,3-c]pyridine-1-carboxylic acid 2-ethoxy-ethyl ester;
D032 5-(3,5-Difluoro-benzenesulfonyl)-3-[4-(4-methyl-piperazin-1-yl)-2-(2-methoxy-ethylamino)-benzoylamino]-4,5,6,7-tetrahydro-pyrazolo[4,3-c]pyridine-1-carboxylic acid 2-(2-methoxy-ethoxy)-ethyl ester;
D033 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid methyl ester;
D034 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid ethyl ester;
D035 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid 2-methoxy-ethyl ester;
D036 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid 2-ethoxy-ethyl ester;
D037 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid 2-(2-methoxy-ethoxy)-ethyl ester;
D038 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid methyl ester;
D039 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid ethyl ester;
D040 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid 2-methoxy-ethyl ester;
D041 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid 2-ethoxy-ethyl ester;
D042 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid 2-(2-methoxy-ethoxy)-ethyl ester;
C043 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid methyl ester;
D044 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid ethyl ester;
D045 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid propyl ester;

D046 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid ispropyl ester;

D047 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid methyl ester;

D048 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid ethyl ester;

D049 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid 2-methoxy-ethyl ester;

D050 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid 2-ethoxy-ethyl ester;

D051 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid methyl ester;

D052 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid ethyl ester;

D053 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid propyl ester;

D054 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid isopropyl ester;

D055 S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D056 S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D057 S-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D058 S-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D059 S-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D060 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D061 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D062 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D063 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-o]pyridine-1-carboxylic acid 2-ethoxy-ethyl ester;

D064 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D065 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D066 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D067 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D068 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D069 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D070 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid methyl ester;

D071 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D072 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid propyl ester;

D073 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ispropyl ester;

D074 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D075 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D076 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D077 S-5-(3,5-Difluoro-benzenesulfonyl)-3-[4-(2-pyrrolidin-1-yl-ethoxy)-2-(2-methoxy-1-methyl-ethylamino)- benzoylamino]-4,5,6,7-tetrahydro-pyrazolo[4,3-c]pyridine-1-carboxylic acid 2-ethoxy-ethyl ester;

D078 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D079 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid ethyl ester;

D080 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid propyl ester;

D081 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid isopropyl ester;

C082 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D083 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D084 R-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D085 R-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D086 R-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D087 R-5-(3,5-Difluoro-benzenesulfonyl)-3-[4-[(2-dimethylamino-ethyl)-methyl-amino]-2-(2-methoxy-1-methy)-ethylamino)-benzoylamino]-4,5,6,7-tetrahydro-pyrazolo[4,3-c]pyridine-1-carboxylic acid methyl ester;

D088 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D089 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D090 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D091 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D092 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D093 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D094 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D095 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D096 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D097 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid methyl ester;

D098 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D099 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid propyl ester;

D0100 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ispropyl ester;

D0101 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D0102 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D0103 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D0104 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D0105 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D0106 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid ethyl ester;

D0107 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid propyl ester;

D0108 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid isopropyl ester;

E01 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid ethyl ester;

E02 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-methoxy-ethyl ester;

E03 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-ethoxy-ethyl ester;

E04 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-(2-methoxy-ethoxy)-ethyl ester;

E05 5-(3,5-Difluoro-benzenesulfonyl)-3-[4-(2-dimethylamino-ethyl)-2-(tetrahydro-pyran-4-ylamino)-benzoylamino]-indazole-1-carboxylic acid methyl ester;

E06 5-(3,5-Difluoro-benzenesulfonyl)-3-[4-(2-dimethylamino-ethyl)-2-(tetrahydro-pyran-4-ylamino)-benzoylamino]-indazole-1-carboxylic acid ethyl ester;

E07 5-(3,5-Difluoro-benzenesulfonyl)-3-[4-(2-dimethylamine-ethyl)-2-(tetrahydro-pyran-4-ylamino)-benzoylamino]-indazole-1-carboxylic acid 2-methoxy-ethyl ester;

E08 5-(3,5-Difluoro-benzenesulfonyl)-3-[4-(2-dimethylamino-ethyl)-2-(tetrahydro-pyran-4-ylamino)-benzoylamino]-indazole-1-carboxylic acid 2-ethoxy-ethyl ester;

E09 5-(3,5-Difluoro-benzenesulfonyl)-3-[4-(2-dimethylamino-propyl)-2-(tetrahydro-pyran-4-ylamino)-benzoylamino]-indazole-1-carboxylic acid methyl ester;

E010 5-(3,5-Difluoro-benzenesulfonyl)-3-[4-(2-dimethylamino-propyl)-2-(tetrahydro-pyran-4-ylamino)-benzoylamino]-indazole-1-carboxylic acid ethyl ester;

E011 5-(3,5-Difluoro-benzenesulfonyl)-3-[4-(2-dimethylamino-propyl)-2-(tetrahydro-pyran-4-ylamino)-benzoylamino]-indazole-1-carboxylic acid 2-methoxy-ethyl ester;

E012 5-(3,5-Difluoro-benzenesulfonyl)-3-[4-(2-dimethylamino-propyl)-2-(tetrahydro-pyran-4-ylamino)-benzoylamino]-indazole-1-carboxylic acid 2-ethoxy-ethyl ester;

E013 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid methyl ester;

E014 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid ethyl ester;

E015 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid 2-methoxy-ethyl ester;

E016 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid 2-ethoxy-ethyl ester;

E017 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid methyl ester;

E018 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid ethyl ester;

E019 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid 2-methoxy-ethyl ester;

E020 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid 2-ethoxy-ethyl ester;

E021 5-(3,5-Difluoro-benzenesulfonyl)-3-[4-(4-methyl-piperazin-1-yl)-2-(2-methoxy-ethylamino)-benzoylamino]-indazole-1-carboxylic acid 2-methoxy-ethyl ester;

E022 5-(3,5-Difluoro-benzenesulfonyl)-3-[4-(4-methyl-piperazin-1-yl)-2-(2-methoxy-ethylamino)-benzoylamino]-indazole-1-carboxylic acid 2-ethoxy-ethyl ester;

E023 5-(3,5-Difluoro-benzenesulfonyl)-3-[4-(4-methyl-piperazin-1-yl)-2-(2-methoxy-ethylamino)-benzoylamino]-indazole-1-carboxylic acid 2-(2-methoxy-ethoxy)-ethyl ester;

E024 5-(3,5-Difluoro-benzenesulfonyl)-3-[4-(2-dimethylamino-ethyl)-2-(2-methoxy-ethylamino)-benzoylamino]-indazole-1-carboxylic acid methyl ester;

E025 5-(3,5-Difluoro-benzenesulfonyl)-3-[4-(2-dimethylamino-ethyl)-2-(2-methoxy-ethylamino)-benzoylamino]-indazole-1-carboxylic acid ethyl ester;

E026 5-(3,5-Difluoro-benzenesulfonyl)-3-[4-(2-dimethylamino-ethyl)-2-(2-methoxy-ethylamino)-benzoylamino]-indazole-1-carboxylic acid 2-methoxy-ethyl ester;

E027 5-(3,5-Difluoro-benzenesulfonyl)-3-[4-(2-dimethylamino-ethyl)-2-(2-methoxy-ethylamino)-benzoylamino]-indazole-1-carboxylic acid 2-ethoxy-ethyl ester;

E028 5-(3,5-Difluoro-benzenesulfonyl)-3-[4-(2-dimethylamino-propyl)-2-(2-methoxy-ethylamino)-benzoylamino]-indazole-1-carboxylic acid methyl ester;

E029 5-(3,5-Difluoro-benzenesulfonyl)-3-[4-(2-dimethylamino-propyl)-2-(2-methoxy-ethylamino)-benzoylamino]-indazole-1-carboxylic acid ethyl ester;

E030 5-(3,5-Difluoro-benzenesulfonyl)-3-[4-(2-dimethylamino-propyl)-2-(2-methoxy-ethylamino)-benzoylamino]-indazole-1-carboxylic acid 2-methoxy-ethyl ester;

E031 5-(3,5-Difluoro-benzenesulfonyl)-3-[4-(2-dimethylamino-propyl)-2-(2-methoxy-ethylamino)-benzoylamino]-indazole-1-carboxylic acid 2-ethoxy-ethyl ester;

E032 5-(3,5-Difluoro-benzenesulfonyl)-3-[4-(2-dimethylamino-ethoxy)-2-(2-methoxy-ethylamino)-benzoylamino]-indazole-1-carboxylic acid methyl ester;

E033 5-(3,5-Difluoro-benzenesulfonyl)-3-[4-(2-dimethylamino-ethoxy)-2-(2-methoxy-ethylamino)-benzoylamino]-indazole-1-carboxylic acid ethyl ester;

E034 5-(3,5-Difluoro-benzenesulfonyl)-3-[4-(2-dimethylamino-ethoxy)-2-(2-methoxy-ethylamino)-benzoylamino]-indazole-1-carboxylic acid 2-methoxy-ethyl ester;

E035 5-(3,5-Difluoro-benzenesulfonyl)-3-[4-(2-dimethylamino-ethoxy)-2-(2-methoxy-ethylamino)-benzoylamino]-indazole-1-carboxylic acid 2-ethoxy-ethyl ester;

E036 5-(3,5-Difluoro-benzenesulfonyl)-3-[4-(pyrrolidin-1-ylmethyl)-2-(2-methoxy-ethylamino)-benzoylamino]-indazole-1-carboxylic acid methyl ester;

E037 5-(3,5-Difluoro-benzenesulfonyl)-3-[4-(pyrrolidin-1-ylmethyl)-2-(2-methoxy-ethylamino)-benzoylamino]-indazole-1-carboxylic acid ethyl ester;

E038 5-(3,5-Difluoro-benzenesulfonyl)-3-[4-(pyrrolidin-1-ylmethyl)-2-(2-methoxy-ethylamino)-benzoylamino]-indazole-1-carboxylic acid 2-methoxy-ethyl ester;

E039 5-(3,5-Difluoro-benzenesulfonyl)-3-[4-(pyrrolidin-1-ylmethyl)-2-(2-methoxy-ethylamino)-benzoylamino]-indazole-1-carboxylic acid 2-ethoxy-ethyl ester;

E040 5-(3,5-Difluoro-benzenesulfonyl)-3-[2-((S)-2-methoxy-1-methyl-ethylamino)-4-(4-methyl-piperazin-1-yl)-benzoylamino]-indazole-1-carboxylic acid ethyl ester;

E041 S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-methoxy-ethyl ester;

E042 S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-ethoxy-ethyl ester;

E043 S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxy-ethoxy)-ethyl ester;

E044 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E045 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E046 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-methoxy-ethyl ester;

E047 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-ethoxy-ethyl ester;

E048 S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E049 S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid ethyl ester;

E050 S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-methoxy-ethyl ester;

E051 S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-ethoxy-ethyl ester;

E052 S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid methyl ester;

E053 S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid ethyl ester;

E054 S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-methoxy-ethyl ester;

E055 S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-ethoxy-ethyl ester;

E056 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E057 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester;

E058 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-methoxy-ethyl ester;

E059 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-ethoxy-ethyl ester;

E060 5-(3,5-Difluoro-benzenesulfonyl)-3-[2-((R)-2-methoxy-1-methyl-ethylamino)-4-(4-methyl-piperazin-1-yl)-benzoylamino]-indazole-1-carboxylic acid ethyl ester;

E061 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-methoxy-ethyl ester;

E062 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-ethoxy-ethyl ester;

E063 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxy-ethoxy)-ethyl ester;

E064 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E065 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E066 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-methoxy-ethyl ester;

E067 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-ethoxy-ethyl ester;

E068 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E069 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid ethyl ester;

E070 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-methoxy-ethyl ester;

E071 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-ethoxy-ethyl ester;

E072 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid methyl ester;

E073 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid ethyl ester;

E074 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-methoxy-ethyl ester;

E075 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-ethoxy-ethyl ester;

E076 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E077 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester;

E078 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-methoxy-ethyl ester;

E079 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-ethoxy-ethyl ester and E080 5-(3,5-Difluoro-benzenesulfonyl)-3-[2-(2-methoxy-ethylamino)-4-(4-methyl-piperazin-1-yl)-benzoylamino]-indazole-1-carboxylic acid ethyl ester.

As stated, the compounds listed above "per se" are another object of the present invention as such their pharmaceutically acceptable salts, but for the compounds coded A02, A024 and C024, known as intermediates, that are object of the present invention for use as medicament as above described only.

Even more preferred compound of the present invention are the following ones:

A02 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid ethyl ester;

A04 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid propyl ester;

A05 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid isopropyl ester;

A08 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid butyl ester;

A09 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid isobutyl ester;

A020 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;

A021 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid 2-fluoroethyl ester;

A024 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid ethyl ester;

A026 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid propyl ester;

A027 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isopropyl ester;

A030 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid butyl ester;

A032 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isobutyl ester;

A042 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;

A043 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-fluoroethyl ester;

B02 5-(1-Methyl-1-phenyl-ethylcarbamoyl)-3-[4-(4-methyl-piperazin-1-ylmethyl)-benzoylamino]-furo[3,2-c]pyrazole-1-carboxylic acid ethyl ester;

B04 5-(1-Methyl-1-phenyl-ethylcarbamoyl)-3-[4-(4-methyl-piperazin-1-ylmethyl)-benzoylamino]-furo[3,2-c]pyrazole-1-carboxylic acid propyl ester;

B05 5-(1-Methyl-1-phenyl-ethylcarbamoyl)-3-[4-(4-methyl-piperazin-1-ylmethyl)-benzoylamino]-furo[3,2-c]pyrazole-1-carboxylic acid isopropyl ester;

B08 5-(1-Methyl-1-phenyl-ethylcarbamoyl)-3-[4-(4-methyl-piperazin-1-ylmethyl)-benzoylamino]-furo[3,2-c]pyrazole-1-carboxylic acid butyl ester;

B09 5-(1-Methyl-1-phenyl-ethylcarbamoyl)-3-[4-(4-methyl-piperazin-1-ylmethyl)-benzoylamino]-furo[3,2-c]pyrazole-1-carboxylic acid isobutyl ester;

B020 5-(1-Methyl-1-phenyl-ethylcarbamoyl)-3-[4-(4-methyl-piperazin-1-ylmethyl)-benzoylamino]-furo[3,2-c]pyrazole-1-carboxylic acid (1R,2S,5R)-2-isopropyl-5-methyl-cyclohexyl ester;

B021 5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-fluoroethyl ester;

B024 5-(1-Methyl-1-phenyl-ethylcarbamoyl)-3-(4-pyrrolidin-1-ylmethyl-benzoylamino)-furo[3,2-c]pyrazole-1-carboxylic acid ethyl ester;

B026 5-(1-Methyl-1-phenyl-ethylcarbamoyl)-3-(4-pyrrolidin-1-ylmethyl-benzoylamino)-furo[3,2-c]pyrazole-1-carboxylic acid propyl ester;

B027 5-(1-Methyl-1-phenyl-ethylcarbamoyl)-3-(4-pyrrolidin-1-ylmethyl-benzoylamino)-furo[3,2-c]pyrazole-1-carboxylic acid isopropyl ester;

B030 5-(1-Methyl-1-phenyl-ethylcarbamoyl)-3-(4-pyrrolidin-1-ylmethyl-benzoylamino)-furo[3,2-c]pyrazole-1-carboxylic acid butyl ester;

B031 5-(1-Methyl-1-phenyl-ethylcarbamoyl)-3-(4-pyrrolidin-1-ylmethyl-benzoylamino)-furo[3,2-c]pyrazole-1-carboxylic acid isobutyl ester;

B042 5-(1-Methyl-1-phenyl-ethylcarbamoyl)-3-(4-pyrrolidin-1-ylmethyl-benzoylamino)-furo[3,2-c]pyrazole-1-carboxylic acid (1R,2S,5R)-2-isopropyl-5-methyl-cyclohexyl ester;

B043 5-(1-Methyl-1-phenyl-ethyl carbamoyl)-3-(4-pyrrolidin-1-ylmethyl-benzoylamino)-furo[3,2-c]pyrazole-1-carboxylic acid 2-fluoroethyl ester;

B046 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid ethyl ester;

B048 5-(1-Methyl-1-phenyl-ethylcarbamoyl)-3-{2-[(2-methyl-2H-pyrazole-3-carbonyl)-amino]benzoylamino}-furo[3,2-c]pyrazole-1-carboxylic acid propyl ester;

B049 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid isopropyl ester;

B052 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid butyl ester;

B053 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid isobutyl ester;

B064 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid (1R,2S,5R)-2-isopropyl-5-methyl-cyclohexyl ester;

B065 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid 2-fluoroethyl ester;

B068 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid ethyl ester;

B070-phenyl-ethyl carbamoyl)-3-{2-[(1-methyl-1H-pyrrole-2-carbonyl)-amino]-benzoylamino}-furo[3,2-c]pyrazole-1-carboxylic acid propyl ester;

B071 5-(1-Methyl-1-phenyl-ethyl carbamoyl)-3-{2-[(1-methyl-1H-pyrrole-2-carbonyl)-amino]-benzoylamino}-furo[3,2-c]pyrazole-1-carboxylic acid isopropyl ester;

B074 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid butyl ester;

B075 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid isobutyl ester;

B086 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid (1R,2S,5R)-2-isopropyl-5-methyl-cyclohexyl ester;

B087 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid 2-fluoroethyl ester;

C02 5-(1-Methyl-1-phenyl-ethylcarbamoyl)-3-(4-piperidin-1-ylmethyl-benzoylamino)-thieno[2,3-c]pyrazole-1-carboxylic acid ethyl ester;

C04 5-(1-Methyl-1-phenyl-ethylcarbamoyl)-3-(4-piperidin-1-ylmethyl-benzoylamino)-thieno[2,3-c]pyrazole-1-carboxylic acid propyl ester;

C05 5-(1-Methyl-1-phenyl-ethylcarbamoyl)-3-(4-piperidin-1-ylmethyl-benzoylamino)-thieno[2,3-c]pyrazole-1-carboxylic acid isopropyl ester;

C08 5-(1-Methyl-1-phenyl-ethylcarbamoyl)-3-(4-piperidin-1-ylmethyl-benzoylamino)-thieno[2,3-c]pyrazole-1-carboxylic acid butyl ester;

C09 5-(1-Methyl-1-phenyl-ethylcarbamoyl)-3-(4-piperidin-1-ylmethyl-benzoylamino)-thieno[2,3-c]pyrazole-1-carboxylic acid isobutyl ester;

C20 5-(1-Methyl-1-phenyl-ethylcarbamoyl)-3-(4-piperidin-1-ylmethyl-benzoylamino)-thieno[2,3-c]pyrazole-1-carboxylic acid (1R,2S,5R)-2-isopropyl-5-methyl-cyclohexyl ester;

C21 5-(1-Methyl-1-phenyl-ethylcarbamoyl)-3-(4-piperidin-1-ylmethyl-benzoylamino)-thieno[2,3-c]pyrazole-1-carboxylic acid 2-fluoroyethyl ester;

C024 5-(1-Methyl-1-phenyl-ethylcarbamoyl)-3-(4-morpholin-4-yl-benzoylamino)-thieno[2,3-c]pyrazole-1-carboxylic acid ethyl ester;

C026 5-(1-Methyl-1-phenyl-ethylcarbamoyl)-3-(4-morpholin-4-yl-benzoylamino)-thieno[2,3-c]pyrazole-1-carboxylic acid propyl ester;

C029 5-(1-Methyl-1-phenyl-ethylcarbamoyl)-3-(4-morpholin-4-yl-benzoylamino)-thieno[2,3-c]pyrazole-1-carboxylic acid isopropyl ester;

C030 5-(1-Methyl-1-phenyl-ethylcarbamoyl)-3-(4-morpholin-4-yl-benzoylamino)-thieno[2,3-c]pyrazole-1-carboxylic acid butyl ester;

C031 5-(1-Methyl-1-phenyl-ethylcarbamoyl)-3-(4-morpholin-4-yl-benzoylamino)-thieno[2,3-c]pyrazole-1-carboxylic acid isobutyl ester;

C042 5-(1-Methyl-1-phenyl-ethylcarbamoyl)-3-(4-morpholin-4-yl-benzoylamino)-thieno[2,3-c]pyrazole-1-carboxylic acid (1R,2S,5R)-2-isopropyl-5-methyl-cyclohexyl ester;

C043 5-(1-Methyl-1-phenyl-ethylcarbamoyl)-3-(4-morpholin-4-yl-benzoylamino)-thieno[2,3-c]pyrazole-1-carboxylic acid 2-fluoroethyl ester;

C046 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid ethyl ester;

C048 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid propyl ester;

C049 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid isopropyl ester;

C052-phenyl-ethylcarbamoyl)-3-[4-(4-methyl-piperazin-1-ylmethyl)-benzoylamino]-thieno[2,3-c]pyrazole-1-carboxylic acid butyl ester;

C053 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid isobutyl ester;

C064 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid (1R,2S,5R)-2-isopropyl-5-methyl-cyclohexyl ester;

C065 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid 2-fluoroethyl ester;

C068 3-[4-(Isopropylamino-methyl)-benzoylamino]-5-(1-methyl-1-phenyl-ethylcarbamoyl)-thieno[2,3-c]pyrazole-1-carboxylic acid ethyl ester;

C070 3-[4-(Isopropylamino-methyl)-benzoylamino]-5-(1-methyl-1-phenyl-ethylcarbamoyl)-thieno[2,3-c]pyrazole-1-carboxylic acid propyl ester;

C071 3-[4-(Isopropylamino-methyl)-benzoylamino]-5-(1-methyl-1-phenyl-ethylcarbamoyl)-thieno[2,3-c]pyrazole-1-carboxylic acid isopropyl ester;

C074 3-[4-(Isopropylamino-methyl)-benzoylamino]-5-(1-methyl-1-phenyl-ethylcarbamoyl)-thieno[2,3-c]pyrazole-1-carboxylic acid butyl ester;

C075 3-[4-(Isopropylamino-methyl)-benzoylamino]-5-(1-methyl-1-phenyl-ethylcarbamoyl)-thieno[2,3-c]pyrazole-1-carboxylic acid isobutyl ester;

C086 3-[4-(Isopropylamino-methyl)-benzoylamino]-5-(1-methyl-1-phenyl-ethylcarbamoyl)-thieno[2,3-c]pyrazole-1-carboxylic acid (1R,2S,5R)-2-isopropyl-5-methyl-cyclohexyl ester;

C087 3-[4-(Isopropylamino-methyl)-benzoylamino]-5-(1-methyl-1-phenyl-ethylcarbamoyl)-thieno[2,3-c]pyrazole-1-carboxylic acid 2-fluoroethyl ester;

C090 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid ethyl ester;

C092 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid propyl ester;

C093 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid isopropyl ester;

C096 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid butyl ester;

C097 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid isobutyl ester;

C0108 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid (1R,2S,5R)-2-isopropyl-5-methyl-cyclohexyl ester;

C0109 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid 2-fluoroethyl ester;

C0112 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid ethyl ester;

C0114 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid propyl ester;

C0115 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid isopropyl ester;

C0118 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid butyl ester;

C0120 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid isobutyl ester;

C0130 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid (1R,2S,5R)-2-isopropyl-5-methyl-cyclohexyl ester;

C0131 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid 2-fluoroethyl ester;

C0134 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid ethyl ester;

C0136 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid propyl ester;

C0137 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid isopropyl ester;

C0140 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid butyl ester;

C0141 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid isobutyl ester;

C0152 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid (1R,2S,5R)-2-isopropyl-5-methyl-cyclohexyl ester;

C0153 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid 2-fluoroethyl ester;

C0156 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid ethyl ester;

C0158 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid propyl ester;

C0159 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid isopropyl ester;

C0162 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid butyl ester;

C0163 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid isobutyl ester;

C0174 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid (1R,2S,5R)-2-isopropyl-5-methyl-cyclohexyl ester;

C0175 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid 2-fluoroethyl ester;

C0178 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid ethyl ester;

C0180 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid propyl ester;

C0181 -phenyl-ethylcarbamoyl)-3-{2-[(1H-pyrrole-3-carbonyl)-amino]-benzoylamino}-thieno[2,3-c]pyrazole-1-carboxylic acid isopropyl ester;

C0184 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid butyl ester;

C0185 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid isobutyl ester;

C0196 -(1-Methyl-1-phenyl-ethylcarbamoyl)-3-{2-[(1H-pyrrole-3-carbonyl)-amino]-benzoylamino}-thieno[2,3-c]pyrazole-1-carboxylic acid (1R,2S,5R)-2-isopropyl-5-methyl-cyclohexyl ester;

C0197 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid 2-fluoroethyl ester;

D01 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid methyl ester;

D02 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid ethyl ester;

D03 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-methoxy-ethyl ester;

D04 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-ethoxy-ethyl ester;

D05 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-(2-methoxy-ethoxy)-ethyl ester;

D06 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D07 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D011 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D012 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D016 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid methyl ester;

D017 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid ethyl ester;

D018 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid propyl ester;

D020 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid methyl ester;

D021 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid ethyl ester;

D024 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid methyl ester;

D025 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid ethyl ester;

D028 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid methyl ester;

D029 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid ethyl ester;

D030 5-(3,5-Difluoro-benzenesulfonyl)-3-[4-(4-methyl-piperazin-1-yl)-2-(2-methoxy-ethylamino)-benzoylamino]-4,5,6,7-tetrahydro-pyrazolo[4,3-c]pyridine-1-carboxylic acid 2-methoxy-ethyl ester;

D033 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid methyl ester;

D034 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid ethyl ester;

D038 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid methyl ester;

D039 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid ethyl ester;

D043 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid methyl ester;

D044 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid ethyl ester;

D047 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid methyl ester;

D048 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid ethyl ester;

D051 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid methyl ester;

D052 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid ethyl ester;

D055 S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D056 S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D057 S-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D060 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D061 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D065 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D066 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D070 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid methyl ester;

D071 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D074 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D075 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D078 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D079 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid ethyl ester;

D082 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D083 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D087 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D088 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D092 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D093 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D097 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid methyl ester;

D098 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D0101 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D0102 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D0105 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D0106 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-e]pyridine-1-carboxylic acid ethyl ester;

E01 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid ethyl ester;

E02 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-methoxy-ethyl ester;

E05 5-(3,5-Difluoro-benzenesulfonyl)-3-[4-(2-dimethylamino-ethyl)-2-(tetrahydro-pyran-4-ylamino)-benzoylamino]-indazole-1-carboxylic acid methyl ester;

E06 5-(3,5-Difluoro-benzenesulfonyl)-3-[4-(2-dimethylamino-ethyl)-2-(tetrahydro-pyran-4-ylamino)-benzoylamino]-indazole-1-carboxylic acid ethyl ester;

E09 5-(3,5-Difluoro-benzenesulfonyl)-3-[4-(2-dimethylamino-propyl)-2-(tetrahydro-pyran-4-ylamino)-benzoylamino]-indazole-1-carboxylic acid methyl ester;

E010 5-(3,5-Difluoro-benzenesulfonyl)-3-[4-(2-dimethylamino-propyl)-2-(tetrahydro-pyran-4-ylamino)-benzoylamino]-indazole-1-carboxylic acid ethyl ester;

E013 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid methyl ester;

E014 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid ethyl ester;

E017 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid methyl ester;

E018 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid ethyl ester;

E024 5-(3,5-Difluoro-benzenesulfonyl)-3-[4-(2-dimethylamino-ethyl)-2-(2-methoxy-ethylamino)-benzoylamino]-indazole-1-carboxylic acid methyl ester;

E025 5-(3,5-Difluoro-benzenesulfonyl)-3-[4-(2-dimethylamino-ethyl)-2-(2-methoxy-ethylamino)-benzoylamino]-indazole-1-carboxylic acid ethyl ester;

E028 5-(3,5-Difluoro-benzenesulfonyl)-3-[4-(2-dimethylamino-propyl)-2-(2-methoxy-ethylamino)-benzoylamino]-indazole-1-carboxylic acid methyl ester;

E029 5-(3,5-Difluoro-benzenesulfonyl)-3-[4-(2-dimethylamino-propyl)-2-(2-methoxy-ethylamino)-benzoylamino]-indazole-1-carboxylic acid ethyl ester;

E032 5-(3,5-Difluoro-benzenesulfonyl)-3-[4-(2-dimethylamino-ethoxy)-2-(2-methoxy-ethylamino)-benzoylamino]-indazole-1-carboxylic acid methyl ester;

E033 5-(3,5-Difluoro-benzenesulfonyl)-3-[4-(2-dimethylamino-ethoxy)-2-(2-methoxy-ethylamino)-benzoylamino]-indazole-1-carboxylic acid ethyl ester;

E036 5-(3,5-Difluoro-benzenesulfonyl)-3-[4-(pyrrolidin-1-ylmethyl)-2-(2-methoxy-ethylamino)-benzoylamino]-indazole-1-carboxylic acid methyl ester;

E037 5-(3,5-Difluoro-benzenesulfonyl)-3-[4-(pyrrolidin-1-ylmethyl)-2-(2-methoxy-ethylamino)-benzoylamino]-indazole-1-carboxylic acid ethyl ester;

E040 5-(3,5-Difluoro-benzenesulfonyl)-3-[2-((S)-2-methoxy-1-methyl-ethylamino)-4-(4-methyl-piperazin-1-yl)-benzoylamino]-indazole-1-carboxylic acid ethyl ester;

E043 S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxy-ethoxy)-ethyl ester;

E044 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E045 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E048 S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E052 S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid methyl ester;

E053 S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid ethyl ester;

E056 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E057 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester;

E060 5-(3,5-Difluoro-benzenesulfonyl)-3-[2-((R)-2-methoxy-1-methyl-ethylamino)-4-(4-methyl-piperazin-1-yl)-benzoylamino]-indazole-1-carboxylic acid ethyl ester;

E063 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxy-ethoxy)-ethyl ester;

E064 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E065 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E068 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E069 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid ethyl ester;

E072 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid methyl ester;

E076 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E077 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester and E080 5-(3,5-Difluoro-benzenesulfonyl)-3-[2-(2-methoxy-ethylamino)-4-(4-methyl-piperazin-1-yl)-benzoylamino]-indazole-1-carboxylic acid ethyl ester.

Even most preferred compounds of the present invention are the following ones:

A02 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid ethyl ester;

A04 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid propyl ester;

A05 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid isopropyl ester;

A08 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid butyl ester;

A024 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid ethyl ester;

A026 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid propyl ester;

A027 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isopropyl ester;

A030 5-((R)-2-Methoxy-2-phenyl-acetyl)-3-[4-(4-methyl-piperazin-111)-benzoylamino]-5,6-dihydro-4H-pyrrolo[3,4-c]pyrazole-1-carboxylic acid butyl ester;

A032 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isobutyl ester;

A042 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;

A043 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-fluoroethyl ester:

B02 5-(1-Methyl-1-phenyl-ethylcarbamoyl)-3-[4-(4-methyl-piperazin-1-ylmethyl)-benzoylamino]-furo[3,2-c]pyrazole-1-carboxylic acid ethyl ester;

B04 5-(1-Methyl-1-phenyl-ethylcarbamoyl)-3-[4-(4-methyl-piperazin-1-ylmethyl)-benzoylamino]-furo[3,2-c]pyrazole-1-carboxylic acid propyl ester;

B05 5-(1-Methyl-1-phenyl-ethylcarbamoyl)-3-[4-(4-methyl-piperazin-1-ylmethyl)-benzoylamino]-furo[3,2-c]pyrazole-1-carboxylic acid isopropyl ester;

B020 5-(1-Methyl-1-phenyl-ethylcarbamoyl)-3-[4-(4-methyl-piperazin-1-ylmethyl)-benzoylamino]-furo[3,2-c]pyrazole-1-carboxylic acid (1R,2S,5R)-2-isopropyl-5-methyl-cyclohexyl ester;

B021 5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-fluoroethyl ester;

B024 5-(1-Methyl-1-phenyl-ethylcarbamoyl)-3-(4-pyrrolidin-1-ylmethyl-benzoylamino)-furo[3,2-c]pyrazole-1-carboxylic acid ethyl ester;

B026 5-(1-Methyl-1-phenyl-ethylcarbamoyl)-3-(4-pyrrolidin-1-ylmethyl-benzoylamino)-furo[3,2-c]pyrazole-1-carboxylic acid propyl ester;

B027 5-(1-Methyl-1-phenyl-ethylcarbamoyl)-3-(4-pyrrolidin-1-ylmethyl-benzoylamino)-furo[3,2-c]pyrazole-1-carboxylic acid isopropyl ester;

B042 5-(1-Methyl-1-phenyl-ethylcarbamoyl)-3-(4-pyrrolidin-1-ylmethyl-benzoylamino)-furo[3,2-c]pyrazole-1-carboxylic acid (1R,2S,5R)-2-isopropyl-5-methyl-cyclohexyl ester;

B046 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid ethyl ester;

B048 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid propyl ester;

B049 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid isopropyl ester;

B064 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid (1R,2S,5R)-2-isopropyl-5-methyl-cyclohexyl ester;

B068 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid ethyl ester;

B070 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid propyl ester;

B071 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid isopropyl ester;

C02 5-(1-Methyl-1-phenyl-ethylcarbamoyl)-3-(4-piperidin-1-ylmethyl-benzoylamino)-thieno[2,3-c]pyrazole-1-carboxylic acid ethyl ester;

C04 5-(1-Methyl-1-phenyl-ethylcarbamoyl)-3-(4-piperidin-1-ylmethyl-benzoylamino)-thieno[2,3-c]pyrazole-1-carboxylic acid propyl ester;

C05 5-(1-Methyl-1-phenyl-ethylcarbamoyl)-3-(4-piperidin-1-ylmethyl-benzoylamino)-thieno[2,3-c]pyrazole-1-carboxylic acid isopropyl ester;

C024 5-(1-Methyl-1-phenyl-ethylcarbamoyl)-3-(4-morpholin-4-yl-benzoylamino)-thieno[2,3-c]pyrazole-1-carboxylic acid ethyl ester;

C026 5-(1-Methyl-1-phenyl-ethylcarbamoyl)-3-(4-morpholin-4-yl-benzoylamino)-thieno[2,3-c]pyrazole-1-carboxylic acid propyl ester;

C029 5-(1-Methyl-1-phenyl-ethylcarbamoyl)-3-(4-morpholin-4-yl-benzoylamino)-thieno[2,3-c]pyrazole-1-carboxylic acid isopropyl ester;

C046 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid ethyl ester;

C048 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid propyl ester;

C049 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid isopropyl ester;

C068 3-[4-(Isopropylamino-methyl)-benzoylamino]-5-(1-methyl-1-phenyl-ethylcarbamoyl)-thieno[2,3-c]pyrazole-1-carboxylic acid ethyl ester;

C070 3-[4-(Isopropylamino-methyl)-benzoylamino]-5-(1-methyl-1-phenyl-ethylcarbamoyl)-thieno[2,3-c]pyrazole-1-carboxylic acid propyl ester;

C071 3-[4-(Isopropylamino-methyl)-benzoylamino]-5-(1-methyl-1-phenyl-ethylcarbamoyl)-thieno[2,3-c]pyrazole-1-carboxylic acid isopropyl ester;

C090 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid ethyl ester;

C092 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid propyl ester;

C093 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid isopropyl ester;

C0112 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid ethyl ester;

C0114 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid propyl ester;

C0115 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid isopropyl ester;

C0134 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid ethyl ester;

C0136 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid propyl ester;

C0137 3-{2-[(1-Methyl-1H-imidazole-2-carbonyl)-amino]-benzoylamino}-5-(1-methyl-1-phenyl-ethylcarbamoyl)-thieno[2,3-c]pyrazole-1-carboxylic acid isopropyl ester;

C0156 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid ethyl ester;

C0158 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid propyl ester;

C0159 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid isopropyl ester;

C0178 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid ethyl ester;

C0180 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid propyl ester;

C0181 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid isopropyl ester;

D01 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid methyl ester;

D02 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid ethyl ester;

D06 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D07 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D11 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D012 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D020 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid methyl ester;

D021 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid ethyl ester;

D024 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid methyl ester;

D025 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid ethyl ester;

D029 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid ethyl ester;

D033 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid methyl ester;

D034 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid ethyl ester;

D038 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid methyl ester;

D039 5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid ethyl ester;

D047 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid methyl ester;

D048 5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid ethyl ester;

D051 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid methyl ester;

D052 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid ethyl ester;

D055 S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D056 S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D060 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D061 S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D064 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D066 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-o]pyridine-1-carboxylic acid ethyl ester;

D074 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D075 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D078 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D079 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid ethyl ester;

D082 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D083 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D087 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D088 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D092 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D093 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

C0101 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D0102 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D0105 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D0106 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid ethyl ester;

E01 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid ethyl ester;

E02 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-methoxy-ethyl ester;

E05 5-(3,5-Difluoro-benzenesulfonyl)-3-[4-(2-dimethylamino-ethyl)-2-(tetrahydro-pyran-4-ylamino)-benzoylamino]-indazole-1-carboxylic acid methyl ester;

E06 5-(3,5-Difluoro-benzenesulfonyl)-3-[4-(2-dimethylamino-ethyl)-2-(tetrahydro-pyran-4-ylamino)-benzoylamino]-indazole-1-carboxylic acid ethyl ester;

E09 5-(3,5-Difluoro-benzenesulfonyl)-3-[4-(2-dimethylamino-propyl)-2-(tetrahydro-pyran-4-ylamino)-benzoylamino]-indazole-1-carboxylic acid methyl ester;

E010 5-(3,5-Difluoro-benzenesulfonyl)-3-[4-(2-dimethylamino-propyl)-2-(tetrahydro-pyran-4-ylamino)-benzoylamino]-indazole-1-carboxylic acid ethyl ester;

E017 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid methyl ester;

E018 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid ethyl ester;

E024 5-(3,5-Difluoro-benzenesulfonyl)-3-[4-(2-dimethylamino-ethyl)-2-(2-methoxy-ethylamino)-benzoylamino]-indazole-1-carboxylic acid methyl ester;

E025 5-(3,5-Difluoro-benzenesulfonyl)-3-[4-(2-dimethylamino-ethyl)-2-(2-methoxy-ethylamino)-benzoylamino]-indazole-1-carboxylic acid ethyl ester;

E028 5-(3,5-Difluoro-benzenesulfonyl)-3-[4-(2-dimethylamino-propyl)-2-(2-methoxy-ethylamino)-benzoylamino]-indazole-1-carboxylic acid methyl ester;

E029 5-(3,5-Difluoro-benzenesulfonyl)-3-[4-(2-dimethylamino-propyl)-2-(2-methoxy-ethylamino)-benzoylamino]-indazole-1-carboxylic acid ethyl ester;

E036 5-(3,5-Difluoro-benzenesulfonyl)-3-[4-(pyrrolidin-1-ylmethyl)-2-(2-methoxy-ethylamino)-benzoylamino]-indazole-1-carboxylic acid methyl ester;

E037 5-(3,5-Difluoro-benzenesulfonyl)-3-[4-(pyrrolidin-1-ylmethyl)-2-(2-methoxy-ethylamino)-benzoylamino]-indazole-1-carboxylic acid ethyl ester;

E040 5-(3,5-Difluoro-benzenesulfonyl)-3-[2-((S)-2-methoxy-1-methyl-ethylamino)-4-(4-methyl-piperazin-1-yl)-benzoylamino]-indazole-1-carboxylic acid ethyl ester;

E043 S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxy-ethoxy)-ethyl ester;

E044 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E045 S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E048 S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E056 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E057 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester;

E060 5-(3,5-Difluoro-benzenesulfonyl)-3-[2-((R)-2-methoxy-1-methyl-ethylamino)-4-(4-methyl-piperazin-1-yl)-benzoylamino]-indazole-1-carboxylic acid ethyl ester;

E063 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxyethoxy)-ethyl ester;

E064 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E065 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E068 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E069 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid ethyl ester;

E076 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E077 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester and E080 5-(3,5-Difluoro-benzenesulfonyl)-3-[2-(2-methoxyethylamino)-4-(4-methyl-piperazin-1-yl)-benzoylamino]-indazole-1-carboxylic acid ethyl ester.

Lastly, the most preferred compounds are listed below:

A024 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid ethyl ester;

A026 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid propyl ester;

A027 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isopropyl ester;

A030 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid butyl ester;

A032 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isobutyl ester;

A042 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;

B02 5-(1-Methyl-1-phenyl-ethylcarbamoyl)-3-[4-(4-methyl-piperazin-1-ylmethyl)-benzoylamino]-furo[3,2-c]pyrazole-1-carboxylic acid ethyl ester;

C02 5-(1-Methyl-1-phenyl-ethylcarbamoyl)-3-(4-piperidin-1-ylmethyl-benzoylamino)-thieno[2,3-c]pyrazole-1-carboxylic acid ethyl ester;

C024 5-(1-Methyl-1-phenyl-ethylcarbamoyl)-3-(4-morpholin-4-yl-benzoylamino)-thieno[2,3-c]pyrazole-1-carboxylic acid ethyl ester;

C068 3-[4-(Isopropylamino-methyl)-benzoylamino]-5-(1-methyl-1-phenyl-ethylcarbamoyl)-thieno[2,3-c]pyrazole-1-carboxylic acid ethyl ester;

D02 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid ethyl ester;

D029 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid ethyl ester;

D056 S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D083 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

E01 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid ethyl ester;

E040 5-(3,5-Difluoro-benzenesulfonyl)-3-[2-((S)-2-methoxy-1-methyl-ethylamino)-4-(4-methyl-piperazin-1-yl)-benzoylamino]-indazole-1-carboxylic acid ethyl ester;

E043 S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxyethoxy)-ethyl ester;

E060 5-(3,5-Difluoro-benzenesulfonyl)-3-[2-((R)-2-methoxy-1-methyl-ethylamino)-4-(4-methyl-piperazin-1-yl)-benzoylamino]-indazole-1-carboxylic acid ethyl ester;

E063 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxyethoxy)-ethyl ester and E080 5-(3,5-Difluoro-benzenesulfonyl)-3-[2-(2-methoxyethylamino)-4-(4-methyl-piperazin-1-yl)-benzoylamino]-indazole-1-carboxylic acid ethyl ester.

As formerly indicated, the process for preparing the compounds of formula (I) represents a further object of the invention.

The compounds of formula (I) and the pharmaceutically acceptable salt thereof can be thus prepared according to a process comprising:

a) reacting an optionally protected bi-cyclic compound of formula (II):

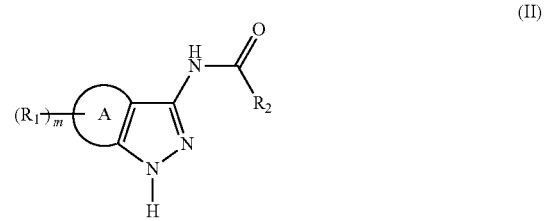

(II)

wherein A, $R_1$, $R_2$ and m are as defined above, with any suitable agent for inserting the desired —C(O)OR group wherein R is as defined above on one of the pyrazole nitrogen atoms, such as a chloroformate derivative, followed by optional removal of the protecting group, if present;

b) if necessary converting the resultant compound of formula (I):

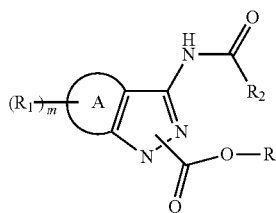

wherein A, R, $R_1$, $R_2$ and m are as defined above, into another compound of formula (I) wherein one or more of $R_1$, $R_2$ or m is different by known reactions;

separating if necessary the obtained isomers of formula (Ia) and (Ib) as defined above according to well-known methods;

converting a compound of formula (I) as defined above into a pharmaceutically acceptable salt or converting the salt thereof into the free compound of formula (I) as defined above.

For a reference to any specific compound of formula (I) of the invention, optionally in the form of a pharmaceutically acceptable salt, see the following experimental section.

Alternatively, the compounds of the formula (I) of present invention may also be obtained by means of well known method described in the patent literature cited above, wherein such compounds are described as useful intermediates.

It is to be noted that also the compounds of formula (II) as above defined can be in any one of its tautomeric forms a or b, not only in the a form depicted above:

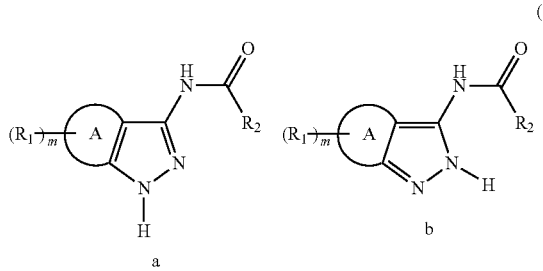

The above processes are analogy processes, which can be carried out according to methods known in the art.

As stated above, it is clear to the person skilled in the art that if a compound of formula (I), prepared according to the above process, is obtained as an admixture of isomers, their separation into the single isomers of formula (I), carried out according to conventional techniques, is still within the scope of the present invention.

According to step (a) of the process, the fused-pyrazole derivative of formula (II) is reacted, according to well-known methods, with an agent for introducing the desired carbamoyl group (—COOR) on one of the pyrazole nitrogen atoms. As an example, the above reaction may occur with an alkyl chloroformate, also named chlorocarbonate, in a suitable solvent such as tetrahydrofuran, dichloromethane, chloroform, acetonitrile, toluene or mixtures thereof, at a temperature ranging from about −5° C. to about 35° C. and for a time varying from about 30 minutes to about 72 hours, in the presence of an opportune proton scavenger such as triethylamine or diisopropylethylamine.

From the above it is clear to the skilled person that this reaction may be accomplished in a variety of ways and operative conditions, which are widely known in the art for the preparation of carbamoyl derivatives.

For a reference to the preparation of the starting compounds of formula (II) see the published patent application cited above.

Pharmacology

As stated above, the compounds of formula (I) of the present invention can use as medicament, and in particular as prodrugs for releasing the active parent drug, according to formula (IA):

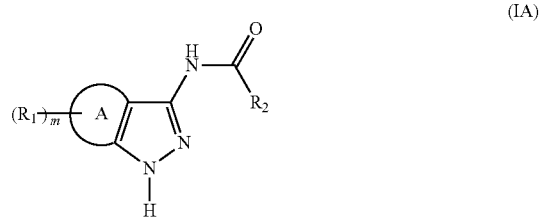

wherein A, $R_1$, $R_2$ and m are as defined above defined, in vivo.

The released compounds of formula (IA) are active as protein kinase inhibitors, more particularly Aurora kinases inhibitors or IGF-R1 inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis.

The inhibiting activity and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay for IGF-1 R Kinase Activity

The buffers/components used in the assay were as follows. Kinase Buffer (buffer KB) was composed of 50 mM HEPES, 3 mM MnCl2, 1 mM DTT, 3 microM Na3VO4, pH 7.9. Enzyme Buffer (buffer EB) was composed of buffer KB containing 0.6 mg/ml BSA (bovine serum albumin). SPA scintillation beads (Product Code Number RPNQ0007, Amersham Biosciences, Piscataway, N.J. USA) were prepared as a 10 mg/ml suspension in PBS containing 32 mM EDTA, 500 microM unlabeled ATP, and 0.1% Triton X-100. This preparation is referred to below as "SPA bead suspension". On the day of assay, IGF-1R was pre-phosphorylated in order to linearize reaction kinetics. To achieve this, the desired quantity of enzyme was incubated for 30 min at 28° C. at a concentration of 1050 nM enzyme in buffer EB containing 100 microM unlabeled ATP. After preincubation, and immediately before assay, this pre-phosphorylated IGF-1R kinase preparation was diluted to an enzyme concentration of 60 nM by addition of 16.5 volumes of buffer KB. This diluted prephosphorylated enzyme is referred to below as "enzyme mix".

The substrate used in the assay was a carboxy-terminally biotinylated peptide of the following sequence: KKKSPGEYVNIEFGGGGGK-biotin. The peptide was obtained in batches of >95% peptide purity from American Peptide Company, Inc. (Sunnyvale, Calif., USA). "ATP Mix", referred to below, consisted of buffer KB containing 6 nM 33 Pg-ATP (gamma phosphate-labeled, Redivue™ Code Number AH9968, 1000-3000 Ci/mmole, Amersham Biosciences Piscataway, N.J. USA), 18 microM unlabeled ATP, and 30 microM biotinylated substrate peptide. This solution contained these components at 3× their final reaction concentrations. Compounds to be tested were prepared in 100% DMSO at appropriate concentrations. These preparations were then diluted 33-fold using buffer KB, so as to obtain compound at 3× the desired final assay concentration in buffer KB containing 3% DMSO. This 3× preparation is referred to below as "compound working solution".

Kinase reaction: Reactions were performed in 96-well U-bottom microtiter plates (such as Product #650101, Greiner Bio-One, Kremsmuenster Austria) in a final reaction volume of 30 microL. To each test well were added 10 microL of "compound working solution" containing appropriate dilution of compound, followed by 10 microL "ATP Mix" and 10 microL "Enzyme Mix", thus starting the reaction. Well contents were immediately mixed by pipetting, and reactions were incubated for 60 minutes at room temperature. After incubation, reactions were stopped by adding 100 microL/well "SPA bead suspension". Wells were incubated a further 15 minutes at room temperature, then 110 microL were withdrawn from each well and transferred to separate wells of 96-well opaque scintillation counting plates (such as OptiPlate™-96, PerkinElmer LAS, Inc. Boston, Mass., USA), each containing 100 microL/well 5M CsCl. After 4 hours resting at room temperature to allow SPA bead floatation, these plates were read using a scintillation counter (Packard TopCount NXT, PerkinElmer LAS, Inc. Boston, Mass., USA) in order to quantitate the light emitted from each well (proportional to the amount of phosphate incorporated into the substrate peptide during kinase reaction).

Many of the steps described above, such as those involving compound dilution, addition of mixes to the reaction, and transfer of completed reaction to counting plates can be automated using robotized pipetting stations (such as Multimek and Biomek liquid handlers, Beckman Coulter Inc., Fullerton Calif. USA), and a dilution curve of a known kinase inhibitor such as staurosporine can be routinely included as a positive control for IGF-1R inhibition.

Results: data were analysed using the "Assay Explorer" software package (Elsevier M D L, San Leandro, Calif. 94577). For single compound concentrations, inhibitory activity was typically expressed as expressed as % inhibition obtained in presence of compound, compared to total activity of enzyme obtained when inhibitor is omitted. Compounds showing desired inhibition can be further analysed in order to study the potency of the inhibitor through IC50 calculation. In this case, inhibition data obtained using serial dilutions of the inhibitor can be fitted by non-linear regression using the following equation:

$$v = v_0 + \frac{(v_0 - v_b)}{1 + 10^{n(\log IC_{50} - \log[I])}}$$

where vb is the baseline velocity, v is the observed reaction velocity, vo is the velocity in the absence of inhibitors, and [I] is the inhibitor concentration.

Western Blot Analysis of Receptor Phosphorylation Following Stimulation with IGF-1 in MCF-7 Human Breast Cancer Cells MCF-7 cells (ATCC# HTB-22) were seeded in 12-well tissue culture plates at 2×10^5 cells/well in E-MEM medium (MEM+ Earle's BSS+2 mM glutamine+0.1 mM non-essential amino acids)+10% FCS, and incubated overnight at 37° C., 5% CO2, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+ Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% BSA+0.15% Tween 20), and probed for 2 hours in the same buffer containing 1/1000 rabbit anti-phospho IGF-1R Tyr1131/InsR Tyr 1146 antibody (product #3021, Cell Signaling Technology, Beverly, Mass., USA) for the detection of phosphorylated IGF-1R, or 1/1000 dilution of rabbit IGF-Irβ(H-60) antibody (product #sc-9038, Santa Cruz Biotechnology, Inc., Santa Cruz, Calif., USA) for detecting total IGF-1R β chain. In either case, filters were then washed for 30 minutes with several changes of TBS+ 0.15% Tween 20, and incubated for 1 hour in washing buffer containing 1/5000 dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts.

Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% CO2 in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., CA, USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed ×2 with PBS, and permeabilized with PBS/0.3% Triton X-100 for 15 minutes. Wells were then saturated with PBS/1% non-fat dry milk (Bio-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at 1/200 dilution in PBS/1% milk/0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+1/500 Goat anti-rabbit Cy5™-conjugated secondary antibody (Amersham Biosciences, Little Chalfont, Buckinghamshire, UK). Wells were then washed ×2 with PBS, and 40 microL PBS are left in each well for immunofluorescence analysis. Fluorescence images in the DAPI and Cy5™ channels were automatically acquired, stored and analysed using a Cellomics ArrayScan™ IV instrument (Cellomics, Pittsburgh, USA); the Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich. St. Louis, Mo., USA.

Inhibition Assay of Aurora-2 Activity

Kinase reaction: 8 biotinylated peptide (4 repeats of LRRWSLG), 10 ATP (0.5 uCi $P^{33}$-ATP), 7.5 ng Aurora 2, inhibitor in a final volume of 30 l buffer (HEPES 50 mM pH 7.0, $MgCl_2$ 10 mM, 1 mM DTT, 0.2 mg/mL BSA, 3M orthovanadate) were added to each well of a 96 U bottom well plate. After 60 minutes at room temperature incubation, reaction was stopped and biotinylated peptide captured by adding 100 l of bead suspension.

Stratification: 100 l of CsCl 5M were added to each well and let stand 4 hour before radioactivity was counted in the Top-Count instrument.

IC50 determination: inhibitors were tested at different concentrations ranging from 0.0015 to 10M. Experimental data were analyzed by the computer program GraphPad Prizm using the four parameter logistic equation:

$y$=bottom+(top−bottom)/(1+10^((logIC50−$x$)*slope))

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM $MgCl_2$, 0.2 mg/mL BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq.1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + a \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. and the cooperativity factor between substrate and ATP binding and substrate and inhibitor binding respectively.

The compounds of the invention were further tested, in vitro, to assess the anti-proliferative effect onto cell cultures.

In Vitro Cell Proliferation Assay

The human colon cancer cell line HCT-116 was seeded at 5000 cells/$cm^2$ in 24 wells plate (Costar) using F12 medium (Gibco) supplemented with 10% FCS (EuroClone, Italy) 2 mM L-glutamine and 1% penicillin/streptomycin and maintained at 37° C., 5% $CO_2$ and 96% relative humidity. The following day, plates were treated in duplicates with 5 ul of an appropriate dilution of compounds starting from a 10 mM stock in DMSO. Two untreated control wells were included in each plate. After 72 hours of treatment, medium was withdrawn and cells detached from each well using 0.5 mL of 0.05% (w/v) Trypsin, 0.02% (w/v) EDTA (Gibco). Samples were diluted with 9.5 mL of Isoton (Coulter) and counted using a Multisizer 3 cell counter (Beckman Coulter). Data were evaluated as percent of the control wells:

% of CTR=(Treated−Blank)/(Control−Blank).

$IC_{50}$ values were calculated by LSW/Data Analysis using Microsoft Excel sigmoidal curve fitting.

As stated above, the compounds of formula (I) of the invention resulted to be very useful as medicament, preferably as prodrugs, even more preferably as prodrugs for the treatment of diseases due to the malfunctioning of protein kinases (PKs), such tumors.

Bioavailability Examples

The following table I reporting the experimental data of some representative compounds of the invention being tested. The compounds of formula (I), formulated in 0.5% Methocel®, were administered orally to mice (10 to 100 mg/Kg) in pharmacokinetic studies and the conversion of the compounds of formula (I) into the corresponding parent active compound (IA) as defined above (i.e. without the —COOR group, wherein R is as defined above) was monitored in blood by HPLC/MS analysis at 15 and 30 min, 1, 6 and 24 h post-dosing. All blood samples were taken from saphenous vein.

Oral bioavailability (Fos) was calculated as percent ratio of average oral AUC value of parent compound after prodrug to average IV AUC value of parent compound after parent compound itself following parent compound dose normalization.

| Compound | Identification or Code | Fos (mouse) |
|---|---|---|
| N-[5-((R)-2-Methoxy-2-phenyl-acetyl)-1,4,5,6-tetrahydro-pyrrolo[3,4-c]pyrazol-3-yl]-4-(4-methyl-piperazin-1-yl)-benzamide | Parent Compound | 1 |
| 5-((R)-2-Methoxy-2-phenyl-acetyl)-3-[4-(4-methyl-piperazin-1-yl)-benzoylamino]-5,6-dihydro-4H-pyrrolo[3,4-c]pyrazoles-1-carboxylic acid ethyl ester | A024 | 13 |
| 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isopropyl ester | A027 | 27 |
| 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester | A042 | 16 |
| N-[5-(3,5-Difluoro-benzenesulfonyl)-1H-indazol-3-yl]-2-((R)-2-methoxy-1-methyl-ethylamino)-4-(4-methyl-piperazin-1-yl)-benzamide | Parent Compound | 53 |
| 5-(3,5-Difluoro-benzenesulfonyl)-3-[2-((R)-2-methoxy-1-methyl-ethylamino)-4-(4-methyl-piperazin-1-yl)-benzoylamino]-indazole-1-carboxylic acid ethyl ester | E060 | 100 |
| 3-(4-Piperidin-1-ylmethyl-benzoylamino)-1H-thieno[2,3-c]pyrazole-5-carboxylic acid (1-methyl-1-phenyl-ethyl)-amide | Parent Compound | 5 |
| 5-(1-Methyl-1-phenyl-ethylcarbamoyl)-3-(4-piperidin-1-ylmethyl-benzoylamino)-thieno[2,3-c]pyrazole-1-carboxylic acid ethyl ester | C02 | 33 |

Moreover, the tested compounds resulted to possess also a very remarkable cell antiproliferative effect.

From all of the above, the compounds of formula (I) of the invention appear to be endowed with a biological profile, considered as a whole, which is unexpectedly superior to that of the prior art and, hence, are particularly advantageous, in therapy, against proliferative disorders associated with an altered kinase activity, in particular altered Aurora-2 kinase activity.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

Another object is therefore the use of a compound of formula (I) or a pharmaceutically acceptable salt thereof, as defined above, in the manufacture of a medicament for treating a disease caused by and/or associated with a dysregulated protein kinase activity, in particular for treating a disease caused by and/or associated with a dysregulated IGF-1R or Aurora kinases activity, preferably with a dysregulated Aurora kinase activity. Such medicament also provides tumor angiogenesis and metastasis inhibition.

The treated disease is preferably selected from the group consisting of cancer, cell proliferative disorders, viral infections, retinopathies including diabetic and neonatal retinopathies and age related macular degeneration, atherosclerosis and conditions involving vascular smooth muscle proliferation or neointimal formation such as restenosis following angioplasty or surgery, graft vessel disease, such as can occur following vessel or organ transplantation, acromegaly and disorders secondary to acromegaly as well as other hypertrophic conditions in which IGF/IGF-1R signalling is implicated, such as benign prostatic hyperplasia, psoriasis, fibrotic lung disease, pulmonary fibrosis, pathologies related to chronic or acute oxidative stress or hyperoxia induced tissue damage, and metabolic disorders in which elevated IGF levels or IGF-1R activity are implicated, such as obesity.

Another object of the present invention is the use of a compound of formula (I) or a pharmaceutically acceptable salt thereof, as defined above, in the manufacture of a medicament with antitumor activity.

According to the invention, the treated cancer is selected from the group consisting of carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

Moreover, the treated cancer can be selected from the group consisting of breast cancer, lung cancer, colorectal cancer, prostate cancer, ovarian cancer, endometrial cancer, gastric cancer, clear cell renal cell carcinoma, uveal melanoma, multiple myeloma, rhabdomyosarcoma, Ewing's sarcoma, Kaposi' sarcoma and medulloblastoma.

The treated cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis, glomerulonephritis and post-surgical stenosis and restenosis.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXAMPLES

The following examples are intended to illustrate but not in any way limit the invention. While the invention has been described with reference to specific methods and embodiments, it will be appreciated that various modifications may be made without departing from the invention.

Example 1

5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid ethyl ester (D02)

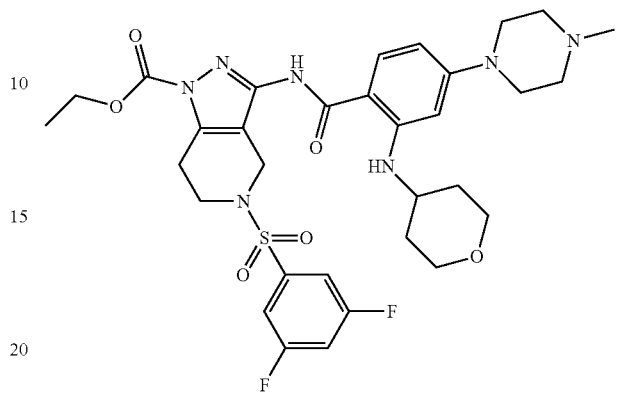

To a solution of N-[5-(3,5-difluoro-benzenesulfonyl)-4,5,6,7-tetrahydro-1H-pyrazolo[4,3-c]pyridin-3-yl]-4-(4-methyl-piperazin-1-yl)-2-(tetrahydro-pyran-4-ylamino)-benzamide (1.38 g, 2.24 mmol) in anhydrous THF (150 mL), cooled to −40° C., under argon, was added lithium bis(trimethylsilyl)amide 1.0 M in THF (2.35 mL, 2.35 mmol). The mixture was stirred for 5 min. then ethyl chloroformate (0.225 mL, 2.35 mmol) was added. The reaction was stirred at −40° C. for 1 h, then was poured in water and extracted with ethyl acetate. The organic phase was washed with water, brine and dried with sodium sulfate. After filtration and evaporation the crude was triturated with ether to give the title compound as white solid (1.32 g, 86%).

$^1$H-NMR (400 MHz), δ (ppm, DMSO-$d_6$): 10.49 (bs, 1H), 8.27 (d, J=7.56 Hz, 1H), 7.75 (d, J=9.15 Hz, 1H), 7.70 (m, 1H), 7.57 (m, 2H), 6.22 (dd, J1=2.07 Hz, J2=9.15 Hz, 1H), 6.12 (d, J=2.07 Hz, 1H), 4.39 (q, J=7.07 Hz, 2H), 4.08 (bs, 2H), 3.82 (m, 2H), 3.73 (m, 1H), 3.55-3.49 (m, 4H), 3.28 (t, J=5.12 Hz, 4H), 3.02 (t, J=5.61 Hz, 2H), 2.43 (t, J=5.12 Hz, 4H), 2.23 (s, 3H), 1.96 (m, 2H), 1.38 (m, 2H), 1.32 (t, J=7.07 Hz, 3H).

Example 2

5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid ethyl ester (E01)

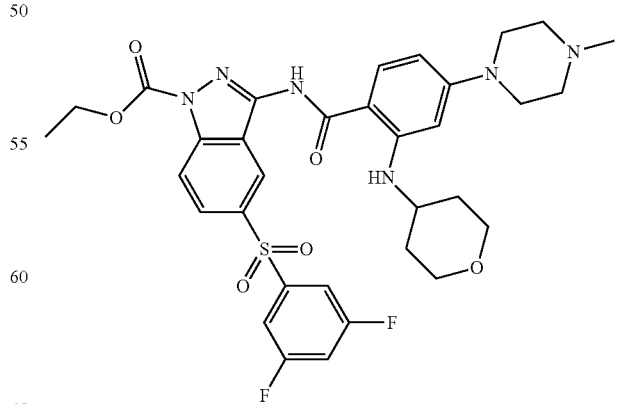

Operating in an analogous way of that described in Example 1, the title compound was obtained.

¹H-NMR (400 MHz), δ (ppm, DMSO-d₆): 10.99 (bs, 1H), 8.59 (d, J=1.71 Hz, 1H), 8.35 (d, J=9.02 Hz, 1H), 8.28 (d, J=7.68 Hz, 1H), 8.25 (dd, J1=1.71 Hz, J2=9.02 Hz, 1H), 7.88 (d, J=9.15 Hz, 1H), 7.77 (m, 2H), 7.68 (m, 1H), 6.32 (dd, J1=2.07 Hz, J2=9.15 Hz, 1H), 6.19 (d, J=2.07 Hz, 1H), 4.53 (q, J=7.07 Hz, 2H), 3.85 (m, 2H), 3.77 (m, 1H), 3.53 (m, 2H), 3.40 (m, 4H), 2.76 (m, 4H), 2.47 (s, 3H), 2.00 (m, 2H), 1.45-1.36 (m, 5H).

Example 3

5-(3,5-Difluoro-benzenesulfonyl)-3-[2-((S)-2-methoxy-1-methyl-ethylamino)-4-(4-methyl-piperazin-1-yl)-benzoylamino]-indazole-1-carboxylic acid ethyl ester (E040)

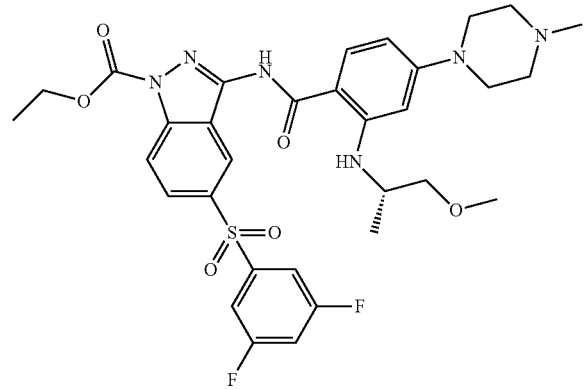 [SMILES: CCOC(=O)n1nc(NC(=O)c2ccc(N3CCN(C)CC3)cc2N[C@@H](C)COC)c2cc(S(=O)(=O)c3cc(F)cc(F)c3)ccc21]

Operating in an analogous way of that described in Example 1, the title compound was obtained.

H-NMR (400 MHz), δ (ppm, DMSO-d₆): 10.93 (bs, 1H), 8.60 (d, J=1.83 Hz, 1H), 8.35 (d, J=9.02 Hz, 1H), 8.24 (dd, J1=1.83 Hz, J2=9.02 Hz, 1H), 8.20 (d, J=7.80 Hz, 1H), 7.83 (d, J=9.02 Hz, 1H), 7.78 (m, 2H), 7.67 (m, 1H), 6.30 (dd, J1=2.32 Hz, J2=9.02 Hz, 1H), 6.15 (d, J=2.32 Hz, 1H), 4.53 (q, J=7.07 Hz, 2H), 3.86 (m, 1H), 3.39 (m, 2H), 3.31-3.30 (m, 5H), 2.44 (m, 4H), 2.24 (s, 3H), 1.41 (t, J=7.07 Hz, 3H), 1.19 (d, J=6.46 Hz, 3H).

Example 4

5-(3,5-Difluoro-benzenesulfonyl)-3-[2-((R)-2-methoxy-1-methyl-ethylamino)-4-(4-methyl-piperazin-1-yl)-benzoylamino]-indazole-1-carboxylic acid ethyl ester (E060)

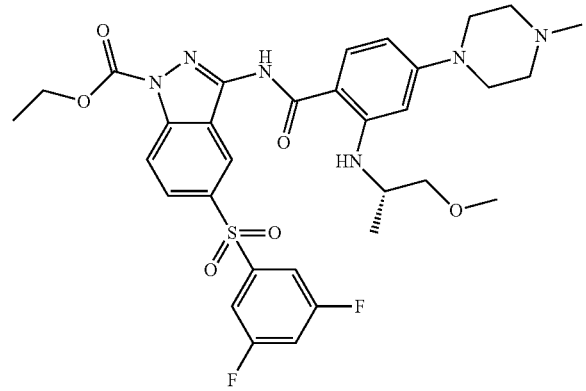 [SMILES: CCOC(=O)n1nc(NC(=O)c2ccc(N3CCN(C)CC3)cc2N[C@@H](C)COC)c2cc(S(=O)(=O)c3cc(F)cc(F)c3)ccc21]

Operating in an analogous way of that described in Example 1, the title compound was obtained.
1H-NMR (400 MHz), δ (ppm, DMSO-d₆): 10.93 (bs, 1H), 8.60 (d, J=1.83 Hz, 1H), 8.35 (d, J=9.02 Hz, 1H), 8.24 (dd, J1=183 Hz, J2=9.02 Hz, 1H), 8.20 (d, J=7.80 Hz, 1H), 7.83 (d, J=9.02 Hz, 1H), 7.78 (m, 2H), 7.67 (m, 1H), 6.30 (dd, J1=2.32 Hz, J2=9.02 Hz, 1H), 6.15 (d, J=2.32 Hz, 1H), 4.53 (q, J=7.07 Hz, 2H), 3.86 (m, 1H), 3.39 (m, 2H), 3.31-3.30 (m, 5H), 2.44 (m, 4H), 2.24 (s, 3H), 1.41 (t, J=7.07 Hz, 3H), 1.19 (d, J=6.46 Hz, 3H).

Example 5

5-(3,5-Difluoro-benzenesulfonyl)-3-[2-(2-methoxy-ethylamino)-4-(4-methyl-piperazin-1-yl)-benzoylamino]-indazole-1-carboxylic acid ethyl ester
(E080)

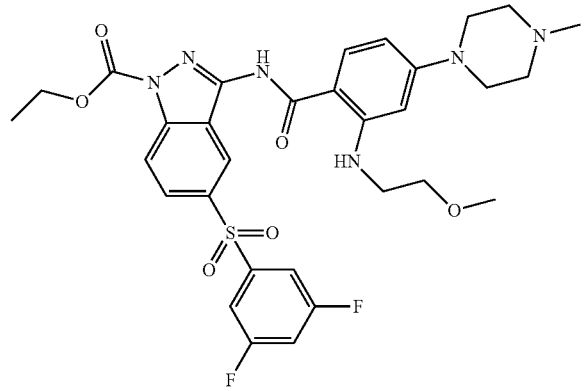 [SMILES: CCOC(=O)n1nc(NC(=O)c2ccc(N3CCN(C)CC3)cc2NCCOC)c2cc(S(=O)(=O)c3cc(F)cc(F)c3)ccc21]

Operating in an Analogous Way of that Described in Example 1, the Title Compound was Obtained 1H-NMR (400 MHz), δ (ppm, DMSO-d₆): 10.94 (bs, 1H), 8.62 (d, J=1.83 Hz, 1H), 8.35 (d, J=9.02 Hz, 1H), 8.24-8.20 (m, 2H), 7.85 (d, J=9.15 Hz, 1H), 7.78 (m, 2H), 7.68 (m, 1H), 6.30 (dd, J1=2.19 Hz, J2=9.15 Hz, 1H), 6.10 (d, J=2.20 Hz, 1H), 4.52 (q, J=7.07 Hz, 2H), 3.58 (t, J=5.37 Hz, 2H), 3.37-3.30 (m, 9H), 2.44 (t, J=5.0 Hz, 4H), 2.24 (s, 3H), 1.41 (t, J=7.07 Hz, 3H).

Example 6

3-[4-(Isopropylamino-methyl)-benzoylamino]-5-(1-methyl-1-phenyl-ethylcarbamoyl)-thieno[2,3-c]pyrazole-1-carboxylic acid ethyl ester (C068)

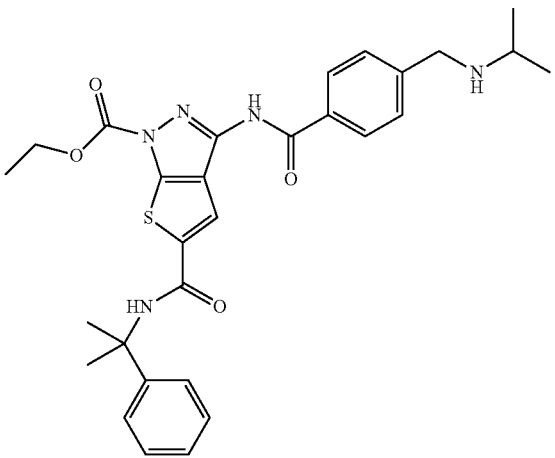 [SMILES: CCOC(=O)n1nc(NC(=O)c2ccc(CNC(C)C)cc2)c2cc(C(=O)NC(C)(C)c3ccccc3)sc21]

Operating in an analogous way of that described in Example 1, the title compound was obtained.
1H-NMR (400 MHz), δ (ppm, DMSO-d₆): 1.02 (d, 6H), 1.38 (t, 3H), 1.68 (s, 6H), 2.72 (m, 1H), 3.78 (br. S, 2H), 4.48

(q, 2H), 7.18 (m, 1H), 7.29 (m, 2H), 7.38 (m, 2H), 7.51 (m, 2H), 8.08 (m, 2H), 8.36 (s, 1H), 8.87 (br. s, 1H), 11.66 (br. s, 1H).

[M+H]$^+$ 548; HRMS (ES$^+$) cald 548.2326, found 548.2310.

Example 7

5-(1-Methyl-1-phenyl-ethylcarbamoyl)-3-(4-piperidin-1-ylmethyl-benzoylamino)-thieno[2,3-c]pyrazole-1-carboxylic acid ethyl ester (C02)

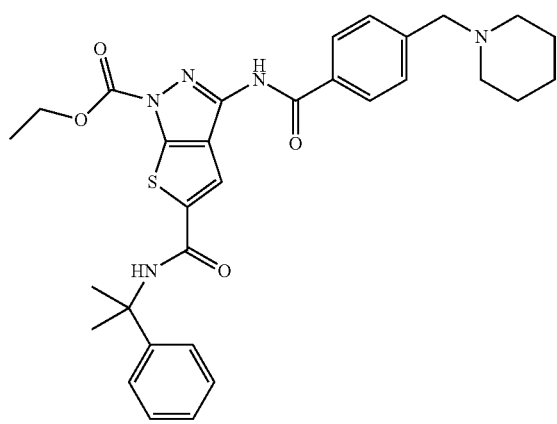 [SMILES: CCOC(=O)n1nc(NC(=O)c2ccc(CN3CCCCC3)cc2)c2cc(C(=O)NC(C)(C)c3ccccc3)sc21]

To a solution of 3-(4-Piperidin-1-ylmethyl-benzoylamino)-1H-thieno[2,3-c]pyrazole-5-carboxylic acid (1-methyl-1-phenyl-ethyl)-amide (500 mg, 1 mmol) in anhydrous THF (20 mL), diisopropylethylamine (1.027 ml, 6 mmol) was added dropwise at room temperature. The reaction was stirred for 5 minutes, and then ethyl chloroformate (130 mg, 0.115 mL, 1.2 mmol) wais also added dropwise. After stirring for 1 hour, the solvent was evaporated, the crude taken up with dichloromethane washed thoroughly with water, brine and dried with sodium sulfate. After filtration and evaporation the crude was triturated with ethyl ether to give the title compound as white solid.

$^1$H-NMR (400 MHz), δ (ppm, DMSO-d$_6$): 1.39 (t, 3H), 1.47-191 (m, 12H), 2.27-2.99 (m, 4H), 3.53 (m, 1H), 4.38 (m, 1H), 4.52 (q, 2H), 7.19 (m, 1H), 7.31 (m, 2H), 7.39 (m, 2H), 7.73 (m, 2H), 8.20 (m, 2H), 8.37 (s, 1H), 8.88 (br. s, 1H), 11.80 (br. S, 1H).

[M+H]$^+$ 574; HRMS (ES$^+$) cald 574.2483, found 574.2463.

Example 8

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid methyl ester (A023)

Operating in an analogous way of that described in Example 7, the title compound was obtained.

$^1$H NMR (400 MHz, DMSO-D6) δ ppm 2.22 (s, 3H), 2.43 (m, 4H), 3.31 (m, 4H), 3.34 (ds, 3H), 3.94 (ds, 3H), 4.36-4.99 (m, 4H), 5.12 (ds, 1H), 6.96 (d, 2H), 7.32-7.45 (m, 5H), 7.93 (dd, 2H), 11.11 (br. s, 1H) [M+H]$^+$ 533; HRMS (ES$^+$) cald 533.2507, found 533.2515

Example 9

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid vinyl ester (A025)

Operating in an analogous way of that described in Example 7, the title compound was obtained.

$^1$H NMR (400 MHz, DMSO-D6) δ ppm 2.23 (s, 3H), 2.45 (m, 4H), 3.34 (m, 4H), 3.35 (ds, 3H), 4.54-4.99 (m, 4H), 5.14 (m, 3H), 6.97 (d, 2H), 7.27 (ddd, 1H), 7.33-7.45 (m, 5H), 7.95 (dd, 2H), 11.20 (d, 1H) [M+H]$^+$ 545; HRMS (ES$^+$) cald 545.2507, found 545.2508

Example 10

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid n-propyl ester (A026)

Operating in an analogous way of that described in Example 7, the title compound was obtained.

$^1$H NMR (400 MHz, DMSO-D6) δ ppm 0.97 (t, 3H), 1.88 (m, 2H) 2.22 (s, 3H), 2.43 (m, 4H), 3.30 (m, 4H), 3.35 (ds, 3H), 4.30 (q, 2H), 4.53-4.95 (m, 4H), 5.00, 5.13 (s, 13H), 6.96 (d, 2H), 7.33-7.45 (m, 5H), 7.94 (m, 2H), 11.13 (d, 1H) [M+H]$^+$ 561; HRMS (ES$^+$) cald 561.2820, found 561.2816

Example 11

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid allyl ester (A028)

Operating in an analogous way of that described in Example 7, the title compound was obtained.

$^1$H NMR (400 MHz, DMSO-D6) δ ppm 2.22 (s, 3H), 2.43 (m, 4H), 3.31 (m, 4H), 3.35 (ds, 3H), 4.54-4.96 (m, 6H), 5.09, 5.1 (s, 13H), 5.35 (dd, 1H), 5.46 (dd, 1H), 6.02 (m, 1H), 6.95 (d, 2H), 7.34-7.45 (m, 5H), 7.94 (m, 2H), 11.14 (d, 1H)

[M+H]$^+$ 559; HRMS (ES$^+$) cald 559.2664, found 559.2651

Example 12

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid propargyl ester (A029)

Operating in an analogous way of that described in Example 7, the title compound was obtained.

$^1$H NMR (400 MHz, DMSO-D6) δ ppm 2.22 (s, 3H), 2.44 (m, 4H), 3.31 (m, 4H), 3.35 (ds, 3H), 3.76 3.82 (m, 2H), 4.45-5.14 (m, 6H), 6.98 (d, 2H), 7.34-7.47 (m, 5H), 7.94 (m, 2H), 11.17 (d, 1H)

[M+H]$^+$ 557; HRMS (ES$^+$) cald 557.2507, found 557.2504

Example 13

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isopropyl ester (A027)

Operating in an analogous way of that described in Example 7, the title compound was obtained.

¹H NMR (400 MHz, DMSO-D6) δ ppm 1.35 (d, 6H), 2.22 (s, 3H), 2.43 (m, 4H), 3.31 (m, 4H), 3.35 (ds, 3H), 4.53-4.96 (m, 4H), 5.06-5.15 (m, 2H), 6.97 (d, 2H), 7.32-7.45 (m, 5H), 7.94 (m, 2H), 11.13 (d, 1H) [M+H]+561; HRMS (ES$^+$) cald 561.2820, found 561.2823

Example 14

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid n-butyl ester (A030) Operating in an Analogous Way of that Described in Example 7, the Title Compound was Obtained ¹H NMR (400 MHz, DMSO-D6) δ ppm 0.94 (m, 3H), 1.41 (m, 2H), 1.69 (m, 2H), 2.22 (s, 3H), 2.43 (m, 4H), 3.30 (m, 4H), 3.35 (ds, 3H), 4.34 (m, 2H), 4.53-4.94 (m, 4H), 5.09 5.13 (ds, 1H), 6.97 (d, 2H), 7.32-7.44 (m, 5H), 7.94 (m, 2H), 11.13 (d, 1H)

[M+H]$^+$ 575; HRMS (ES$^+$) cald 575.2977, found 575.2953

Example 15

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isobutyl ester (A032) Operating in an Analogous Way of that Described in Example 7, the Title Compound was Obtained ¹H NMR (400 MHz, DMSO-D6) δ ppm 0.97 (d, 6H), 2.03 (m, 1H), 2.22 (s, 3H), 2.42 (m, 4H), 3.29 (m, 4H), 3.35 (ds, 3H), 4.13 (m, 2H), 4.54-4.95 (m, 4H), 5.09 5.13 (ds, 1H), 6.98 (d, 2H), 7.32-7.45 (m, 5H), 7.94 (m, 2H), 11.13 (d, 1H).

[M+H]$^+$ 575; HRMS (ES$^+$) cald 575.2977, found 575.2967

Example 16

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid tert-butyl ester (A033) Operating in an Analogous Way of that Described in Example 7, the Title Compound was Obtained ¹H NMR (400 MHz, DMSO-D6) δ ppm 1.56 (s, 9H), 2.22 (s, 3H), 2.42 (m, 4H), 3.31 (m, 4H), 3.34 (s, 3H), 4.13 (m, 2H), 4.56-4.95 (m, 4H), 5.10 5.12 (ds, 1H), 6.96 (d, 2H), 7.32-7.45 (m, 5H), 7.94 (m, 2H), 11.11 (d, 1H).

[M+H]$^+$ 575; HRMS (ES$^+$) cald 575.2977, found 575.2972

Example 17

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-methoxy-ethyl ester (A041) Operating in an Analogous Way of that Described in Example 7, the Title Compound was Obtained ¹H NMR (400 MHz, DMSO-D6) δ ppm 2.22 (s, 3H), 2.42 (m, 4H), 3.29-3.35 (m, 10H), 3.64 (m, 2H), 4.45-4.97 (m, 6H), 5.08 5.13 (ds, 1H), 6.96 (d, 2H), 7.34-7.44 (m, 5H), 7.94 (m, 2H), 11.11 (d, 1H).

[M+H]$^+$ 577; HRMS (ES$^+$) cald 577.2769, found 577.2766

Example 18

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid neopentyl ester (A035) Operating in an Analogous Way of that Described in Example 7, the Title Compound was Obtained ¹H NMR (400 MHz, DMSO-D6) δ ppm 1.00 (s, 9H), 2.22 (s, 3H), 2.44 (m, 4H), 3.29-3.33 (m, 4H), 3.35, 3.36 (ds, 3H), 4.09 (s, 2H), 4.56-4.96 (m, 4H), 5.07, 5.14 (ds, 1H), 6.98 (d, 2H), 7.34-7.46 (m, 5H), 7.94 (m, 2H), 11.13 (d, 1H).

[M+H]$^+$ 589; HRMS (ES$^+$) cald 589.3133, found 589.3135

Example 19

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid n-hexyl ester (A036) Operating in an Analogous Way of that Described in Example 7, the Title Compound was Obtained ¹H NMR (400 MHz, DMSO-D6) δ ppm 0.88 (m, 3H), 1.29-1.41 (m, 6H), 1.90 (m, 2H), 2.22 (s, 3H), 2.42 (m, 4H), 3.27-3.32 (m, 4H), 3.33, 3.34 (ds, 3H), 4.34 (m, 2H), 4.54-4.95 (m, 4H), 5.09 5.13 (ds, 1H), 6.96 (d, 2H), 7.32-7.44 (m, 5H), 7.94 (m, 2H), 11.13 (d, 1H).

[M+H]$^+$ 603; HRMS (ES$^+$) cald 603.3290, found 603.3289

Example 20

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester (A042)

Operating in an analogous way of that described in Example 7, the title compound was obtained.

¹H NMR (400 MHz, DMSO-D6) δ ppm 0.76 (m, 3H), 0.92, (m, 6H), 1.46-1.96 (m, 7H), 2.06 (m, 2H), 2.23 (s, 3H), 2.44 (m, 4H), 3.29-3.33 (m, 4H), 3.35, 3.37 (ds, 3H), 4.53-4.98 (m, 5H), 5.13 (s, 1H), 6.97 (d, 2H), 7.33-7.45 (m, 5H), 7.94 (m, 2H), 11.15 (d, 1H).

[M+H]$^+$ 657; HRMS (ES$^+$) cald 657.3759, found 657.3781

Example 21

5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid benzyl ester (A038) Operating in an Analogous Way of that Described in Example 7, the Title Compound was Obtained ¹H NMR (400 MHz, DMSO-D6) δ ppm 2.24 (s, 3H), 2.46 (m, 4H), 3.30 (m, 4H), 3.34 (s, 3H), 4.49-4.94 (m, 4H), 5.01, 5.13 (ds, 1H), 5.42 (s, 2H), 6.97 (d, 2H), 7.31-7.55 (m, 10H), 7.34 (m, 2H), 11.13 (d, 1H)

[M+H]$^+$ 608; HRMS (ES$^+$) cald 609.2820, found 609.2823.

The invention claimed is:

1. A method for treating cell proliferative disorders, the cell proliferative disorders selected from the group consisting of breast cancer, colon cancer, lung cancer, blood cancer, pancreatic cancer, skin cancer, brain cancer and bone cancer and combinations thereof, which comprises administering to a mammal in need thereof, as a prodrug, an effective amount of a compound of the formula (I):

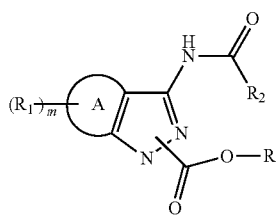

wherein
R represents a straight or branched $C_1$-$C_{12}$ alkyl, an aryl or heteroaryl group,
$R_1$ represents a hydrogen atom or a substituent attached to any available atom of the A ring,
$R_2$ represents an optionally substituted group selected from straight or branched $C_1$-$C_6$ alkyl, aryl, heteroaryl, $C_3$-$C_6$ cycloalkyl, $C_2$-$C_6$ alkenyl or alkynyl, $C_3$-$C_6$ cycloalkyl $C_1$-$C_6$ alkyl, aryl $C_1$-$C_6$ alkyl, heteroaryl $C_1$-$C_6$ alkyl, a 5 or 6 membered heterocyclyl and heterocyclyl $C_1$-$C_6$ alkyl with from 1 to 3 heteroatoms selected from nitrogen, oxygen and sulphur,
A ring represents a phenyl or a heterocycle and
m is a value from 1 to 6,
or a pharmaceutically acceptable salt thereof.

2. A method according to claim 1, wherein the compound of formula (I) is selected from the group consisting of:
A01   5-(2,6-Diethyl-phenylcarbamoyl)-3-[4-(4-methyl-piperazin-1-yl)-benzoylamino]-5,6-dihydro-4H-pyrrolo[3,4-e]pyrazole-1-carboxylic acid methyl ester;
A02   5-(2,6-Diethyl-phenylcarbamoyl)-3-[4-(4-methyl-piperazin-1-yl)-benzoylamino]-5,6-dihydro-4H-pyrrolo[3,4-e]pyrazole-1-carboxylic acid ethyl ester;
A03   5-(2,6-Diethyl-phenylcarbamoyl)-3-[4-(4-methyl-piperazin-1-yl)-benzoylamino]-5,6-dihydro-4H-pyrrolo[3,4-e]pyrazole-1-carboxylic acid vinyl ester;
A04   5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid propyl ester;
A05   5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid isopropyl ester;
A06   5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid allyl ester;
A07   5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid propargyl ester;
A08   5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid butyl ester;
A09   5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid isobutyl ester;
A010  5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid sec-butyl ester;
A011  5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid tert-butyl ester;
A012  5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid pentyl ester;
A013  5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid neopentyl ester;
A014  5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid hexyl ester;

A015 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid heptyl ester;

A016 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid benzyl ester;

A017 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid phenyl ester;

A018 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid 2-methoxyethyl ester;

A019 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid cyclopentyl ester;

A020 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;

A021 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid 2-fluoroethyl ester;

A022 5-(2,6-Diethyl-phenylcarbamoyl)-3-[4-(4-methyl-piperazin-1-yl)-benzoylamino]-5,6-dihydro-4H-pyrrolo[3,4-c]pyrazole-1-carboxylic acid 2-chloroethyl ester;

A023 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid methyl ester;

A024 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid ethyl ester;

A025 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid vinyl ester;

A026 5-((R)-2-Methoxy-2-phenyl-acetyl)-3-[4-(4-methyl-piperazin-1-yl)-benzoylamino]-5,6-dihydro-4H-pyrrolo[3,4-e]pyrazole-1-carboxylic acid propyl ester;

A027 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isopropyl ester;

A028 5-((R)-2-Methoxy-2-phenyl-acetyl)-3-[4-(4-methyl-piperazin-1-yl)-benzoylamino]-5,6-dihydro-4H-pyrrolo[3,4-e]pyrazole-1-carboxylic acid allyl ester;

A029 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid propargyl ester;

A030 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid butyl ester;

A031 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid sec-butyl ester;

A032 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid isobutyl ester;

A033 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid tert-butyl ester;

A034 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid pentyl ester;

A035 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid neopentyl ester;

A036 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid hexyl ester;

A037 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid heptyl ester;

A038 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid benzyl ester;

A039 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid phenyl ester;

A040 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid cyclopentyl ester;

A041 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-methoxyethyl ester;

A042 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid (1R,2S,5R)-2-isopropyl-5-methyl-cyclohexyl ester;

A043 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-fluoroethyl ester;

A044 5-((R)-2-Methoxy-2-phenyl-acetyl)-3-[4-(4-methyl-piperazin-1-yl)-benzoylamino]-5,6-dihydro-4H-pyrrolo[3,4-c]pyrazole-1-carboxylic acid 2-chloroethyl ester;

B01 5-(1-Methyl-1-phenyl-ethylcarbamoyl)-3-[4-(4-methyl-piperazin-1-ylmethyl)-benzoylamino]-furo[3,2-c]pyrazole-1-carboxylic acid methyl ester;

B02 5-(1-Methyl-1-phenyl-ethylcarbamoyl)-3-[4-(4-methyl-piperazin-1-ylmethyl)-benzoylamino]-furo[3,2-c]pyrazole-1-carboxylic acid ethyl ester;

B03 5-(1-Methyl-1-phenyl-ethylcarbamoyl)-3-[4-(4-methyl-piperazin-1-ylmethyl)-benzoylamino]-furo[3,2-c]pyrazole-1-carboxylic acid vinyl ester;

B04 5-(1-Methyl-1-phenyl-ethylcarbamoyl)-3-[4-(4-methyl-piperazin-1-ylmethyl)-benzoylamino]-faro[3,2-c]pyrazole-1-carboxylic acid propyl ester;

B05 5-(1-Methyl-1-phenyl-ethylcarbamoyl)-3-[4-(4-methyl-piperazin-1-ylmethyl)-benzoylamino]-furo[3,2-c]pyrazole-1-carboxylic acid isopropyl ester;

B06 5-(1-Methyl-1-phenyl-ethylcarbamoyl)-3-[4-(4-methyl-piperazin-1-ylmethyl)-benzoylamino]-furo[3,2-c]pyrazole-1-carboxylic acid allyl ester;

B07 5-(1-Methyl-1-phenyl-ethylcarbamoyl)-3-[4-(4-methyl-piperazin-1-ylmethyl)-benzoylamino]-furo[3,2-c]pyrazole-1-carboxylic acid propargyl ester;

B08 5-(1-Methyl-1-phenyl-ethylcarbamoyl)-3-[4-(4-methyl-piperazin-1-ylmethyl)-benzoylamino]-furo[3,2-c]pyrazole-1-carboxylic acid butyl ester;

B09 5-(1-Methyl-1-phenyl-ethylcarbamoyl)-3-[4-(4-methyl-piperazin-1-ylmethyl)-benzoylamino]-furo[3,2-c]pyrazole-1-carboxylic acid isobutyl ester;

B010 5-(1-Methyl-1-phenyl-ethylcarbamoyl)-3-[4-(4-methyl-piperazin-1-ylmethyl)-benzoylamino]-furo[3,2-c]pyrazole-1-carboxylic acid sec-butyl ester;
B011 5-(1-Methyl-1-phenyl-ethylcarbamoyl)-3-[4-(4-methyl-piperazin-1-ylmethyl)-benzoylamino]-furo[3,2-c]pyrazole-1-carboxylic acid tert-butyl ester;
B012 5-(1-Methyl-1-phenyl-ethylcarbamoyl)-3-[4-(4-methyl-piperazin-1-ylmethyl)-benzoylamino]-furo[3,2-c]pyrazole-1-carboxylic acid pentyl ester;
B013 5-(1-Methyl-1-phenyl-ethylcarbamoyl)-3-[4-(4-methyl-piperazin-1-ylmethyl)-benzoylamino]-furo[3,2-c]pyrazole-1-carboxylic acid neopentyl ester;
B014 5-(1-Methyl-1-phenyl-ethylcarbamoyl)-3-[4-(4-methyl-piperazin-1-ylmethyl)-benzoylamino]-furo[3,2-c]pyrazole-1-carboxylic acid hexyl ester;
B015 5-(1-Methyl-1-phenyl-ethylcarbamoyl)-3-[4-(4-methyl-piperazin-1-ylmethyl)-benzoylamino]-furo[3,2-c]pyrazole-1-carboxylic acid heptyl ester;
B016 5-(1-Methyl-1-phenyl-ethylcarbamoyl)-3-[4-(4-methyl-piperazin-1-ylmethyl)-benzoylamino]-furo[3,2-c]pyrazole-1-carboxylic acid benzyl ester;
B017 5-(1-Methyl-1-phenyl-ethylcarbamoyl)-3-[4-(4-methyl-piperazin-1-ylmethyl)-benzoylamino]-furo[3,2-c]pyrazole-1-carboxylic acid phenyl ester;
B018 5-(1-Methyl-1-phenyl-ethylcarbamoyl)-3-[4-(4-methyl-piperazin-1-ylmethyl)-benzoylamino]-furo[3,2-c]pyrazole-1-carboxylic acid cyclopentyl ester;
B019 5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-methoxyethyl ester;
B020 5-(1-Methyl-1-phenyl-ethylcarbamoyl)-3-[4-(4-methyl-piperazin-1-ylmethyl)-benzoylamino]-furo[3,2-c]pyrazole-1-carboxylic acid (1R,2S,5R)-2-isopropyl-5-methyl-cyclohexyl ester;
B021 5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-fluoroethyl ester;
B022 5-(1-Methyl-1-phenyl-ethylcarbamoyl)-3-[4-(4-methyl-piperazin-1-ylmethyl)-benzoylamino]-furo[3,2-c]pyrazole-1-carboxylic acid 2-chloroethyl ester;
B023 5-(1-Methyl-1-phenyl-ethylcarbamoyl)-3-(4-pyrrolidin-1-ylmethyl-benzoylamino)-furo[3,2-c]pyrazole-1-carboxylic acid methyl ester;
B024 5-(1-Methyl-1-phenyl-ethylcarbamoyl)-3-(4-pyrrolidin-1-ylmethyl-benzoylamino)-furo[3,2-c]pyrazole-1-carboxylic acid ethyl ester;
B025 5-(1-Methyl-1-phenyl-ethylcarbamoyl)-3-(4-pyrrolidin-1-ylmethyl-benzoylamino)-furo[3,2-c]pyrazole-1-carboxylic acid vinyl ester;
B026 5-(1-Methyl-1-phenyl-ethylcarbamoyl)-3-(4-pyrrolidin-1-ylmethyl-benzoylamino)-furo[3,2-c]pyrazole-1-carboxylic acid propyl ester;
B027 5-(1-Methyl-1-phenyl-ethylcarbamoyl)-3-(4-pyrrolidin-1-ylmethyl-benzoylamino)-furo[3,2-c]pyrazole-1-carboxylic acid isopropyl ester;
B028 5-(1-Methyl-1-phenyl-ethylcarbamoyl)-3-(4-pyrrolidin-1-ylmethyl-benzoylamino)-furo[3,2-c]pyrazole-1-carboxylic acid allyl ester;
B029 5-(1-Methyl-1-phenyl-ethylcarbamoyl)-3-(4-pyrrolidin-1-ylmethyl-benzoylamino)-furo[3,2-c]pyrazole-1-carboxylic acid propargyl ester;
B030 5-(1-Methyl-1-phenyl-ethylcarbamoyl)-3-(4-pyrrolidin-1-ylmethyl-benzoylamino)-furo[3,2-c]pyrazole-1-carboxylic acid butyl ester;
B031 5-(1-Methyl-1-phenyl-ethylcarbamoyl)-3-(4-pyrrolidin-1-ylmethyl-benzoylamino)-furo[3,2-c]pyrazole-1-carboxylic acid isobutyl ester;
B032 5-(1-Methyl-1-phenyl-ethylcarbamoyl)-3-(4-pyrrolidin-1-ylmethyl-benzoylamino)-furo[3,2-c]pyrazole-1-carboxylic acid sec-butyl ester;
B033 5-(1-Methyl-1-phenyl-ethylcarbamoyl)-3-(4-pyrrolidin-1-ylmethyl-benzoylamino)-furo[3,2-c]pyrazole-1-carboxylic acid tert-butyl ester;
B034 5-(1-Methyl-1-phenyl-ethylcarbamoyl)-3-(4-pyrrolidin-1-ylmethyl-benzoylamino)-furo[3,2-c]pyrazole-1-carboxylic acid pentyl ester;
B035 5-(1-Methyl-1-phenyl-ethylcarbamoyl)-3-(4-pyrrolidin-1-ylmethyl-benzoylamino)-furo[3,2-c]pyrazole-1-carboxylic acid neopentyl ester;
B036 5-(1-Methyl-1-phenyl-ethylcarbamoyl)-3-(4-pyrrolidin-1-ylmethyl-benzoylamino)-furo[3,2-c]pyrazole-1-carboxylic acid hexyl ester;
B037 5-(1-Methyl-1-phenyl-ethylcarbamoyl)-3-(4-pyrrolidin-1-ylmethyl-benzoylamino)-furo[3,2-c]pyrazole-1-carboxylic acid heptyl ester;
B038 5-(1-Methyl-1-phenyl-ethylcarbamoyl)-3-(4-pyrrolidin-1-ylmethyl-benzoylamino)-furo[3,2-c]pyrazole-1-carboxylic acid benzyl ester;
B039 5-(1-Methyl-1-phenyl-ethylcarbamoyl)-3-(4-pyrrolidin-1-ylmethyl-benzoylamino)-furo[3,2-c]pyrazole-1-carboxylic acid phenyl ester;
B040 5-(1-Methyl-1-phenyl-ethylcarbamoyl)-3-(4-pyrrolidin-1-ylmethyl-benzoylamino)-furo[3,2-c]pyrazole-1-carboxylic acid cyclopentyl ester;
B041 5-(1-Methyl-1-phenyl-ethylcarbamoyl)-3-(4-pyrrolidin-1-ylmethyl-benzoylamino)-furo[3,2-c]pyrazole-1-carboxylic acid 2-methoxyethyl ester;
B042 5-(1-Methyl-1-phenyl-ethylcarbamoyl)-3-(4-pyrrolidin-1-ylmethyl-benzoylamino)-furo[3,2-c]pyrazole-1-carboxylic acid (1R,2S,5R)-2-isopropyl-5-methyl-cyclohexyl ester;
B043 5-(1-Methyl-1-phenyl-ethylcarbamoyl)-3-(4-pyrrolidin-1-ylmethyl-benzoylamino)-furo[3,2-c]pyrazole-1-carboxylic acid 2-fluoroethyl ester;
B044 5-(1-Methyl-1-phenyl-ethylcarbamoyl)-3-(4-pyrrolidin-1-ylmethyl-benzoylamino)-furo[3,2-c]pyrazole-1-carboxylic acid 2-chloroethyl ester;
B045 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid methyl ester;
B046 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid ethyl ester;
B047 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid vinyl ester;
B048 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid propyl ester;
B049 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid isopropyl ester;
B050 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid allyl ester;

B051 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid propargyl ester;

B052 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid butyl ester;

B053 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid isobutyl ester;

B054 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid sec-butyl ester;

B055 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid tert-butyl ester;

B056 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid pentyl ester;

B057 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid neopentyl ester;

B058 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid hexyl ester;

B059 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid heptyl ester;

B060 5-(1-Methyl-1-phenyl-ethylcarbamoyl)-3-{2-[(2-methyl-2H-pyrazole-3-carbonyl)-amino]-benzoylamino}-furo[3,2-e]pyrazole-1-carboxylic acid benzyl ester;

B061 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid phenyl ester;

B062 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid cyclopentyl ester;

B063 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid 2-methoxyethyl ester;

B064 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid (1R,2S,5R)-2-isopropyl-5-methyl-cyclohexyl ester;

B065 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid 2-fluoroethyl ester;

B066 5-(1-Methyl-1-phenyl-ethylcarbamoyl)-3-{2-[(2-methyl-2H-pyrazole-3-carbonyl)-amino]-benzoylamino}-furo[3,2-c]pyrazole-1-carboxylic acid 2-chloroethyl ester;

B067 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid methyl ester;

B068 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid ethyl ester;

B069 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid vinyl ester;

B070 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid propyl ester;

B071 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid isopropyl ester;

B072 5-(1-Methyl-1-phenyl-ethylcarbamoyl)-3-{2-[(1-methyl-1H-pyrrole-2-carbonyl)-amino]-benzoylamino}-furo[3,2-e]pyrazole-1-carboxylic acid allyl ester;

B073 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid propargyl ester;

B074 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid butyl ester;

B075 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid isobutyl ester;

B076 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid sec-butyl ester;

B077 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid tert-butyl ester;

B078 5-(1-Methyl-1-phenyl-ethylcarbamoyl)-3-{2-[(1-methyl-1H-pyrrole-2-carbonyl)-amino]benzoylamino}-furo[3,2-c]pyrazole-1-carboxylic acid pentyl ester;

B079 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid neopentyl ester;

B080 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid hexyl ester;

B081 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid heptyl ester;

B082 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid benzyl ester;

B083 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid phenyl ester;

B084 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid 2-methoxyethyl ester;

B085 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid cyclopentyl ester;

B086 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid (1R,2S,5R)-2-isopropyl-5-methyl-cyclohexyl ester;

B087 5-(1-Methyl-1-phenyl-ethylcarbamoyl)-3-{2-[(1-methyl-1H-pyrrole-2-carbonyl)-amino]-benzoylamino}-furo[3,2-c]pyrazole-1-carboxylic acid 2-fluoroethyl ester;

B088 5-(1-Methyl-1-phenyl-ethylcarbamoyl)-3-{2-[(1-methyl-1H-pyrrole-2-carbonyl)-amino]-benzoylamino}-furo[3,2-e]pyrazole-1-carboxylic acid 2-chloroethyl ester;

C01 5-(1-Methyl-1-phenyl-ethylcarbamoyl)-3-(4-piperidin-1-ylmethyl-benzoylamino)-thieno[2,3-c]pyrazole-1-carboxylic acid methyl ester;

C02 5-(1-Methyl-1-phenyl-ethylcarbamoyl)-3-(4-piperidin-1-ylmethyl-benzoylamino)-thieno[2,3-c]pyrazole-1-carboxylic acid ethyl ester;

C03 5-(1-Methyl-1-phenyl-ethylcarbamoyl)-3-(4-piperidin-1-ylmethyl-benzoylamino)-thieno[2,3-c]pyrazole-1-carboxylic acid vinyl ester;

C04 5-(1-Methyl-1-phenyl-ethylcarbamoyl)-3-(4-piperidin-1-ylmethyl-benzoylamino)-thieno[2,3-c]pyrazole-1-carboxylic acid propyl ester;

C05 5-(1-Methyl-1-phenyl-ethylcarbamoyl)-3-(4-piperidin-1-ylmethyl-benzoylamino)-thieno[2,3-c]pyrazole-1-carboxylic acid isopropyl ester;

C06 5-(1-Methyl-1-phenyl-ethylcarbamoyl)-3-(4-piperidin-1-ylmethyl-benzoylamino)-thieno[2,3-c]pyrazole-1-carboxylic acid allyl ester;

C07 5-(1-Methyl-1-phenyl-ethylcarbamoyl)-3-(4-piperidin-1-ylmethyl-benzoylamino)-thieno[2,3-c]pyrazole-1-carboxylic acid propargyl ester;

C08 5-(1-Methyl-1-phenyl-ethylcarbamoyl)-3-(4-piperidin-1-ylmethyl-benzoylamino)-thieno[2,3-c]pyrazole-1-carboxylic acid butyl ester;

C09 5-(1-Methyl-1-phenyl-ethylcarbamoyl)-3-(4-piperidin-1-ylmethyl-benzoylamino)-thieno[2,3-c]pyrazole-1-carboxylic acid isobutyl ester;

C010 5-(1-Methyl-1-phenyl-ethylcarbamoyl)-3-(4-piperidin-1-ylmethyl-benzoylamino)-thieno[2,3-c]pyrazole-1-carboxylic acid sec-butyl ester;

C011 5-(1-Methyl-1-phenyl-ethylcarbamoyl)-3-(4-piperidin-1-ylmethyl-benzoylamino)-thieno[2,3-c]pyrazole-1-carboxylic acid tert-butyl ester;

C012 5-(1-Methyl-1-phenyl-ethylcarbamoyl)-3-(4-piperidin-1-ylmethyl-benzoylamino)-thieno[2,3-c]pyrazole-1-carboxylic acid pentyl ester;

C013 5-(1-Methyl-1-phenyl-ethylcarbamoyl)-3-(4-piperidin-1-ylmethyl-benzoylamino)-thieno[2,3-c]pyrazole-1-carboxylic acid neopentyl ester;

C014 5-(1-Methyl-1-phenyl-ethylcarbamoyl)-3-(4-piperidin-1-ylmethyl-benzoylamino)-thieno[2,3-c]pyrazole-1-carboxylic acid hexyl ester;

C015 5-(1-Methyl-1-phenyl-ethylcarbamoyl)-3-(4-piperidin-1-ylmethyl-benzoylamino)-thieno[2,3-c]pyrazole-1-carboxylic acid heptyl ester;

C016 5-(1-Methyl-1-phenyl-ethylcarbamoyl)-3-(4-piperidin-1-ylmethyl-benzoylamino)-thieno[2,3-c]pyrazole-1-carboxylic acid benzyl ester;

C017 5-(1-Methyl-1-phenyl-ethylcarbamoyl)-3-(4-piperidin-1-ylmethyl-benzoylamino)-thieno[2,3-c]pyrazole-1-carboxylic acid phenyl ester;

C018 5-(1-Methyl-1-phenyl-ethylcarbamoyl)-3-(4-piperidin-1-ylmethyl-benzoylamino)-thieno[2,3-c]pyrazole-1-carboxylic acid cyclopentyl ester;

C019 5-(1-Methyl-1-phenyl-ethylcarbamoyl)-3-(4-piperidin-1-ylmethyl-benzoylamino)-thieno[2,3-c]pyrazole-1-carboxylic acid 2-methoxyethyl ester;

C020 5-(1-Methyl-1-phenyl-ethylcarbamoyl)-3-(4-piperidin-1-ylmethyl-benzoylamino)-thieno[2,3-c]pyrazole-1-carboxylic acid (1R,2S,5R)-2-isopropyl-5-methyl-cyclohexyl ester;

C021 5-(1-Methyl-1-phenyl-ethylcarbamoyl)-3-(4-piperidin-1-ylmethyl-benzoylamino)-thieno[2,3-c]pyrazole-1-carboxylic acid 2-fluoroyethyl ester;

C022 5-(1-Methyl-1-phenyl-ethylcarbamoyl)-3-(4-piperidin-1-ylmethyl-benzoylamino)-thieno[2,3-c]pyrazole-1-carboxylic acid 2-chloroethyl ester;

C023 5-(1-Methyl-1-phenyl-ethylcarbamoyl)-3-(4-morpholin-4-yl-benzoylamino)-thieno[2,3-c]pyrazole-1-carboxylic acid methyl ester;

C024 5-(1-Methyl-1-phenyl-ethylcarbamoyl)-3-(4-morpholin-4-yl-benzoylamino)-thieno[2,3-c]pyrazole-1-carboxylic acid ethyl ester;

C025 5-(1-Methyl-1-phenyl-ethylcarbamoyl)-3-(4-morpholin-4-yl-benzoylamino)-thieno[2,3-c]pyrazole-1-carboxylic acid vinyl ester;

C026 5-(1-Methyl-1-phenyl-ethylcarbamoyl)-3-(4-morpholin-4-yl-benzoylamino)-thieno[2,3-c]pyrazole-1-carboxylic acid propyl ester;

C027 5-(1-Methyl-1-phenyl-ethylcarbamoyl)-3-(4-morpholin-4-yl-benzoylamino)-thieno[2,3-c]pyrazole-1-carboxylic acid allyl ester;

C028 5-(1-Methyl-1-phenyl-ethylcarbamoyl)-3-(4-morpholin-4-yl-benzoylamino)-thieno[2,3-c]pyrazole-1-carboxylic acid propargyl ester;

C029 5-(1-Methyl-1-phenyl-ethylcarbamoyl)-3-(4-morpholin-4-yl-benzoylamino)-thieno[2,3-c]pyrazole-1-carboxylic acid isopropyl ester;

C030 5-(1-Methyl-1-phenyl-ethylcarbamoyl)-3-(4-morpholin-4-yl-benzoylamino)-thieno[2,3-c]pyrazole-1-carboxylic acid butyl ester;

C031 5-(1-Methyl-1-phenyl-ethylcarbamoyl)-3-(4-morpholin-4-yl-benzoylamino)-thieno[2,3-c]pyrazole-1-carboxylic acid isobutyl ester;

C032 5-(1-Methyl-1-phenyl-ethylcarbamoyl)-3-(4-morpholin-4-yl-benzoylamino)-thieno[2,3-c]pyrazole-1-carboxylic acid sec-butyl ester;

C033 5-(1-Methyl-1-phenyl-ethylcarbamoyl)-3-(4-morpholin-4-yl-benzoylamino)-thieno[2,3-c]pyrazole-1-carboxylic acid tert-butyl ester;

C034 5-(1-Methyl-1-phenyl-ethylcarbamoyl)-3-(4-morpholin-4-yl-benzoylamino)-thieno[2,3-c]pyrazole-1-carboxylic acid pentyl ester;

C035 5-(1-Methyl-1-phenyl-ethylcarbamoyl)-3-(4-morpholin-4-yl-benzoylamino)-thieno[2,3-c]pyrazole-1-carboxylic acid neopentyl ester;

C036 5-(1-Methyl-1-phenyl-ethylcarbamoyl)-3-(4-morpholin-4-yl-benzoylamino)-thieno[2,3-c]pyrazole-1-carboxylic acid hexyl ester;

C037 5-(1-Methyl-1-phenyl-ethylcarbamoyl)-3-(4-morpholin-4-yl-benzoylamino)-thieno[2,3-c]pyrazole-1-carboxylic acid heptyl ester;

C038 5-(1-Methyl-1-phenyl-ethylcarbamoyl)-3-(4-morpholin-4-yl-benzoylamino)-thieno[2,3-c]pyrazole-1-carboxylic acid benzyl ester;

C039 5-(1-Methyl-1-phenyl-ethylcarbamoyl)-3-(4-morpholin-4-yl-benzoylamino)-thieno[2,3-c]pyrazole-1-carboxylic acid phenyl ester;

C040 5-(1-Methyl-1-phenyl-ethylcarbamoyl)-3-(4-morpholin-4-yl-benzoylamino)-thieno[2,3-c]pyrazole-1-carboxylic acid 2-methoxyethyl ester;

C041 5-(1-Methyl-1-phenyl-ethylcarbamoyl)-3-(4-morpholin-4-yl-benzoylamino)-thieno[2,3-c]pyrazole-1-carboxylic acid cyclopentyl ester;

C042 5-(1-Methyl-1-phenyl-ethylcarbamoyl)-3-(4-morpholin-4-yl-benzoylamino)-thieno[2,3-c]pyrazole-1-carboxylic acid (1R,2S,5R)-2-isopropyl-5-methyl-cyclohexyl ester;

C043 5-(1-Methyl-1-phenyl-ethylcarbamoyl)-3-(4-morpholin-4-yl-benzoylamino)-thieno[2,3-c]pyrazole-1-carboxylic acid 2-fluoroethyl ester;

C044 5-(1-Methyl-1-phenyl-ethylcarbamoyl)-3-(4-morpholin-4-yl-benzoylamino)-thieno[2,3-c]pyrazole-1-carboxylic acid 2-chloroethyl ester;

C045 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid methyl ester;

C46 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid ethyl ester;

C047 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid vinyl ester;

C048 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid propyl ester;

C049 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid isopropyl ester;

C050 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid allyl ester;

C051 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid propargyl ester;

C052 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid butyl ester;

C053 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid isobutyl ester;

C054 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid sec-butyl ester;

C055 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid tert-butyl ester;

C056 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid pentyl ester;

C057 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid neopentyl ester;

C058 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid hexyl ester;

C059 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid heptyl ester;

C060 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid benzyl ester;

C061 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid phenyl ester;

C062 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid 2-methoxyethyl ester;

C063 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid cyclopentyl ester;

C064 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid (1R,2S,5R)-2-isopropyl-5-methyl-cyclohexyl ester;

C065 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid 2-fluoroethyl ester;

C066 5-(1-Methyl-1-phenyl-ethylcarbamoyl)-3-[4-(4-methyl-piperazin-1-ylmethyl)-benzoylamino]-thieno[2,3-c]pyrazole-1-carboxylic acid 2-chloroethyl ester;

C067 3-[4-(Isopropylamino-methyl)-benzoylamino]-5-(1-methyl-1-phenyl-ethylcarbamoyl)-thieno[2,3-c]pyrazole-1-carboxylic acid methyl ester;

C068 3-[4-(Isopropylamino-methyl)-benzoylamino]-5-(1-methyl-1-phenyl-ethylcarbamoyl)-thieno[2,3-c]pyrazole-1-carboxylic acid ethyl ester;

C069 3-[4-(Isopropylamino-methyl)-benzoylamino]-5-(1-methyl-1-phenyl-ethylcarbamoyl)-thieno[2,3-c]pyrazole-1-carboxylic acid vinyl ester;

C070 3-[4-(Isopropylamino-methyl)-benzoylamino]-5-(1-methyl-1-phenyl-ethylcarbamoyl)-thieno[2,3-c]pyrazole-1-carboxylic acid propyl ester;

C071 3-[4-(Isopropylamino-methyl)-benzoylamino]-5-(1-methyl-1-phenyl-ethylcarbamoyl)-thieno[2,3-c]pyrazole-1-carboxylic acid isopropyl ester;

C072 3-[4-(Isopropylamino-methyl)-benzoylamino]-5-(1-methyl-1-phenyl-ethylcarbamoyl)-thieno[2,3-c]pyrazole-1-carboxylic acid allyl ester;

C073 3-[4-(Isopropylamino-methyl)-benzoylamino]-5-(1-methyl-1-phenyl-ethylcarbamoyl)-thieno[2,3-c]pyrazole-1-carboxylic acid propargyl ester;

C074 3-[4-(Isopropylamino-methyl)-benzoylamino]-5-(1-methyl-1-phenyl-ethylcarbamoyl)-thieno[2,3-c]pyrazole-1-carboxylic acid butyl ester;

C075 3-[4-(Isopropylamino-methyl)-benzoylamino]-5-(1-methyl-1-phenyl-ethylcarbamoyl)-thieno[2,3-c]pyrazole-1-carboxylic acid isobutyl ester;

C076 3-[4-(Isopropylamino-methyl)-benzoylamino]-5-(1-methyl-1-phenyl-ethylcarbamoyl)-thieno[2,3-c]pyrazole-1-carboxylic acid sec-butyl ester;

C077 3-[4-(Isopropylamino-methyl)-benzoylamino]-5-(1-methyl-1-phenyl-ethylcarbamoyl)-thieno[2,3-c]pyrazole-1-carboxylic acid tert-butyl ester;

C078 3-[4-(Isopropylamino-methyl)-benzoylamino]-5-(1-methyl-1-phenyl-ethylcarbamoyl)-thieno[2,3-c]pyrazole-1-carboxylic acid pentyl ester;

C079 3-[4-(Isopropylamino-methyl)-benzoylamino]-5-(1-methyl-1-phenyl-ethylcarbamoyl)-thieno[2,3-c]pyrazole-1-carboxylic acid neopentyl ester;

C080 3-[4-(Isopropylamino-methyl)-benzoylamino]-5-(1-methyl-1-phenyl-ethylcarbamoyl)-thieno[2,3-c]pyrazole-1-carboxylic acid hexyl ester;

C081 3-[4-(Isopropylamino-methyl)-benzoylamino]-5-(1-methyl-1-phenyl-ethylcarbamoyl)-thieno[2,3-c]pyrazole-1-carboxylic acid heptyl ester;
C082 3-[4-(Isopropylamino-methyl)-benzoylamino]-5-(1-methyl-1-phenyl-ethylcarbamoyl)-thieno[2,3-c]pyrazole-1-carboxylic acid benzyl ester;
C083 3-[4-(Isopropylamino-methyl)-benzoylamino]-5-(1-methyl-1-phenyl-ethylcarbamoyl)-thieno[2,3-c]pyrazole-1-carboxylic acid phenyl ester;
C084 3-[4-(Isopropylamino-methyl)-benzoylamino]-5-(1-methyl-1-phenyl-ethylcarbamoyl)-thieno[2,3-c]pyrazole-1-carboxylic acid cyclopentyl ester;
C085 3-[4-(Isopropylamino-methyl)-benzoylamino]-5-(1-methyl-1-phenyl-ethylcarbamoyl)-thieno[2,3-c]pyrazole-1-carboxylic acid 2-methoxyethyl ester;
C086 3-[4-(Isopropylamino-methyl)-benzoylamino]-5-(1-methyl-1-phenyl-ethylcarbamoyl)-thieno[2,3-c]pyrazole-1-carboxylic acid (1R,2S,5R)-2-isopropyl-5-methyl-cyclohexyl ester;
C087 3-[4-(Isopropylamino-methyl)-benzoylamino]-5-(1-methyl-1-phenyl-ethylcarbamoyl)-thieno[2,3-c]pyrazole-1-carboxylic acid 2-fluoroethyl ester;
C088 3-[4-(Isopropylamino-methyl)-benzoylamino]-5-(1-methyl-1-phenyl-ethylcarbamoyl)-thieno[2,3-c]pyrazole-1-carboxylic acid 2-chloroethyl ester;
C089 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid methyl ester;
C090 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid ethyl ester;
C091 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid vinyl ester;
C092 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid propyl ester;
C093 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid isopropyl ester;
C094 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid propargyl ester;
C095 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid allyl ester;
C096 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid butyl ester;
C097 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid isobutyl ester;
C098 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid sec-butyl ester;
C099 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid tert-butyl ester;
C0100 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid pentyl ester;
C0101 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid neopentyl ester;
C0102 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid hexyl ester;
C0103 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid heptyl ester;
C0104 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid benzyl ester;
C0105 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid phenyl ester;
C0106 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid cyclopentyl ester;
C0107 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid 2-methoxyethyl ester;
C0108 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid (1R,2S,5R)-2-isopropyl-5-methyl-cyclohexyl ester;
C0109 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid 2-fluoroethyl ester;
C0110 5-[1-(2-Chloro-phenyl)-1-methyl-ethylcarbamoyl]-3-(4-piperidin-1-ylmethyl-benzoylamino)-thieno[2,3-c]pyrazole-1-carboxylic acid 2-chloroethyl ester;
C0111 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid methyl ester;
C0112 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid ethyl ester;
C0113 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid vinyl ester;
C0114 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid propyl ester;
C0115 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid isopropyl ester;
C0116 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid allyl ester;
C0117 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid propargyl ester;
C0118 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid butyl ester;
C0119 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid sec-butyl ester;
C0120 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid isobutyl ester;
C0121 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid tert-butyl ester;
C0122 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid pentyl ester;
C0123 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid neopentyl ester;

C0124 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid hexyl ester;

C0125 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid heptyl ester;

C0126 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid benzyl ester;

C0127 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid phenyl ester;

C0128 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid cyclopentyl ester;

C0129 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid 2-methoxyethyl ester;

C0130 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid (1R,2S,5R)-2-isopropyl-5-methyl-cyclohexyl ester;

C0131 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid 2-fluoroethyl ester;

C0132 5-[1-(2-Fluoro-phenyl)-1-methyl-ethylcarbamoyl]-3-(4-morpholin-4-ylmethyl-benzoylamino)-thieno[2,3-c]pyrazole-1-carboxylic acid 2-chloroethyl ester;

C0133 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid methyl ester;

C0134 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid ethyl ester;

C0135 3-{2-[(1-Methyl-1H-imidazole-2-carbonyl)-amino]-benzoylamino}-5-(1-methyl-1-phenyl-ethyl-carbamoyl)-thieno[2,3-e]pyrazole-1-carboxylic acid vinyl ester;

C0136 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid propyl ester;

C0137 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid isopropyl ester;

C0138 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid allyl ester;

C0139 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid propargyl ester;

C0140 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid butyl ester;

C0141 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid isobutyl ester;

C0142 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid sec-butyl ester;

C0143 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid tert-butyl ester;

C0144 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid pentyl ester;

C0145 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid neopentyl ester;

C0146 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid hexyl ester;

C0147 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid heptyl ester;

C0148 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid benzyl ester;

C0149 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid phenyl ester;

C0150 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid 2-methoxyethyl ester;

C0151 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid cyclopentyl ester;

C0152 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid (1R,2S,5R)-2-isopropyl-5-methyl-cyclohexyl ester;

C0153 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid 2-fluoroethyl ester;

C0154 3-{2-[(1-Methyl-1H-imidazole-2-carbonyl)-amino]-benzoylamino}-5-(1-methyl-1-phenyl-ethyl-carbamoyl)-thieno[2,3-c]pyrazole-1-carboxylic acid 2-chloroethyl ester;

C0155 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid methyl ester;

C0156 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid ethyl ester;

C0157 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid vinyl ester;

C0158 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid propyl ester;

C0159 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid isopropyl ester;

C0160 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid allyl ester;

C0161 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid propargyl ester;

C0162 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid butyl ester;

C0163 3-(4-Morpholin-4-yl-benzoylamino)-5-((S)-1-phenyl-2-pyrrolidin-1-yl-ethylcarbamoyl)-thieno[3,2-e]pyrazole-1-carboxylic acid isobutyl ester;

C0164 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid sec-butyl ester;

C0165 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid tert-butyl ester;

C0166 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid pentyl ester;

C0167 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid neopentyl ester;

C0168 3-(4-Morpholin-4-yl-benzoylamino)-5-((S)-1-phenyl-2-pyrrolidin-1-yl-ethylcarbamoyl)-thieno[3,2-e]pyrazole-1-carboxylic acid hexyl ester;

C0169 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid heptyl ester;

C0170 3-(4-Morpholin-4-yl-benzoylamino)-5-((S)-1-phenyl-2-pyrrolidin-1-yl-ethylcarbamoyl)-thieno[3,2-e]pyrazole-1-carboxylic acid benzyl ester;

C0171 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid phenyl ester;

C0172 3-(4-Morpholin-4-yl-benzoylamino)-5-((S)-1-phenyl-2-pyrrolidin-1-yl-ethylcarbamoyl)-thieno[3,2-e]pyrazole-1-carboxylic acid cyclopentyl ester;

C0173 3-(4-Morpholin-4-yl-benzoylamino)-5-((S)-1-phenyl-2-pyrrolidin-1-yl-ethylcarbamoyl)-thieno[3,2-e]pyrazole-1-carboxylic acid 2-methoxyethyl ester;

C0174 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid (1R,2S,5R)-2-isopropyl-5-methyl-cyclohexyl ester;

C0175 3-(4-Morpholin-4-yl-benzoylamino)-5-((S)-1-phenyl-2-pyrrolidin-1-yl-ethylcarbamoyl)-thieno[3,2-c]pyrazole-1-carboxylic acid 2-fluoro ethyl ester;

C0176 3-(4-Morpholin-4-yl-benzoylamino)-5-((S)-1-phenyl-2-pyrrolidin-1-yl-ethylcarbamoyl)-thieno[3,2-e]pyrazole-1-carboxylic acid 2-chloroethyl ester;

C0177 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid methyl ester;

C0178 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid ethyl ester;

C0179 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid vinyl ester;

C0180 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid propyl ester;

C0181 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid isopropyl ester;

C0182 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid allyl ester;

C0183 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid propargyl ester;

C0184 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid butyl ester;

C0185 5-(1-Methyl-1-phenyl-ethylcarbamoyl)-3-{2-[(1H-pyrrole-3-carbonyl)-amino]-benzoylamino}-thieno[2,3-e]pyrazole-1-carboxylic acid isobutyl ester;

C0186 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid sec-butyl ester;

C0187 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid tert-butyl ester;

C0188 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid pentyl ester;

C0189 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid neopentyl ester;

C0190 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid hexyl ester;

C0191 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid heptyl ester;

C0192 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid heptyl ester;

C0193 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid benzyl ester;

C0194 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid cyclopentyl ester;

C0195 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid 2-methoxyethyl ester;

C0196 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid (1R,2S,5R)-2-isopropyl-5-methyl-cyclohexyl ester;

C0197 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid 2-fluoroethyl ester;

C0198 5-(1-Methyl-1-phenyl-ethylcarbamoyl)-3-{2-[(1H-pyrrole-3-carbonyl)-amino]-benzoylamino}-thieno[2,3-c]pyrazole-1-carboxylic acid 2-chloroethyl ester;

D01 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid methyl ester;

D02 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid ethyl ester;

D03 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-methoxy-ethyl ester;

D04 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-ethoxy-ethyl ester;

D05 5-(3,5-Difluoro-benzenesulfonyl)-3-[4-(4-methyl-piperazin-1-yl)-2-(tetrahydro-pyran-4-ylamino)-benzoylamino]-4,5,6,7-tetrahydro-pyrazolo[4,3-c]pyridine-1-carboxylic acid 2-(2-methoxy-ethoxy)-ethyl ester;

D06 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D07 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D08 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid 2-methoxy-ethyl ester;

D09 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid 2-ethoxy-ethyl ester;

D010 5-(3,5-Difluoro-benzenesulfonyl)-3-[4-[(2-dimethylamino-ethyl)-methyl-amino]-2-(tetrahydro-pyran-4-ylamino)-benzoylamino]-4,5,6,7-tetrahydro-pyrazolo[4,3-c]pyridine-1-carboxylic acid 2-(2-methoxy-ethoxy)-ethyl ester;

D011 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid methyl ester;

D012 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid ethyl ester;

D013 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid 2-methoxy-ethyl ester;

D014 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid 2-ethoxy-ethyl ester;

D015 5-(3,5-Difluoro-benzenesulfonyl)-3-[4-[(2-dimethylamino-propyl)-methyl-amino]-2-(tetrahydro-pyran-4-ylamino)-benzoylamino]-4,5,6,7-tetrahydro-pyrazolo[4,3-c]pyridine-1-carboxylic acid 2-(2-methoxy-ethoxy)-ethyl ester;

D016 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid methyl ester;

D017 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid ethyl ester;

D018 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid propyl ester;

D019 5-(3,5-Difluoro-benzenesulfonyl)-3-[4-(2-dimethylamino-ethoxy)-2-(tetrahydro-pyran-4-ylamino)-benzoylamino]-4,5,6,7-tetrahydro-pyrazolo[4,3-c]pyridine-1-carboxylic acid isopropyl ester;

D020 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid methyl ester;

D021 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid ethyl ester;

D022 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid 2-methoxy-ethyl ester;

D023 5-(3,5-Difluoro-benzenesulfonyl)-3-[4-(2-pyrrolidin-1-yl-ethoxy)-2-(tetrahydro-pyran-4-ylamino)-benzoylamino]-4,5,6,7-tetrahydro-pyrazolo[4,3-c]pyridine-1-carboxylic acid 2-ethoxy-ethyl ester;

D024 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid methyl ester;

D025 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid ethyl ester;

D026 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid propyl ester;

D027 5-(3,5-Difluoro-benzenesulfonyl)-3-[4-(pyrrolidin-1-ylmethyl)-2-(tetrahydro-pyran-4-ylamino)-benzoylamino]-4,5,6,7-tetrahydro-pyrazolo[4,3-c]pyridine-1-carboxylic acid isopropyl ester;

D028 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid methyl ester;

D029 5-(3,5-Difluoro-benzenesulfonyl)-3-[2-(2-methoxy-ethylamino)-4-(4-methyl-piperazin-1-yl)-benzoylamino]-4,5,6,7-tetrahydro-pyrazolo[4,3-c]pyridine-1-carboxylic acid ethyl ester;

D030 5-(3,5-Difluoro-benzenesulfonyl)-3-[4-(4-methyl-piperazin-1-yl)-2-(2-methoxy-ethylamino)-benzoylamino]-4,5,6,7-tetrahydro-pyrazolo[4,3-c]pyridine-1-carboxylic acid 2-methoxy-ethyl ester;

D031 5-(3,5-Difluoro-benzenesulfonyl)-3-[4-(4-methyl-piperazin-1-yl)-2-(2-methoxy-ethylamino)-benzoylamino]-4,5,6,7-tetrahydro-pyrazolo[4,3-c]pyridine-1-carboxylic acid 2-ethoxy-ethyl ester;

D032 5-(3,5-Difluoro-benzenesulfonyl)-3-[4-(4-methyl-piperazin-1-yl)-2-(2-methoxy-ethylamino)-benzoylamino]-4,5,6,7-tetrahydro-pyrazolo[4,3-c]pyridine-1-carboxylic acid 2-(2-methoxy-ethoxy)-ethyl ester;

D033 5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid methyl ester;

D034  5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid ethyl ester;

D035  5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid 2-methoxy-ethyl ester;

D036  5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid 2-ethoxy-ethyl ester;

D037  5-(3,5-Difluoro-benzenesulfonyl)-3-[4-[(2-dimethylamino-ethyl)-methyl-amino]-2-(2-methoxy-ethylamino)-benzoylamino]-4,5,6,7-tetrahydro-pyrazolo[4,3-c]pyridine-1-carboxylic acid 2-(2-methoxy-ethoxy)-ethyl ester;

D038  5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid methyl ester;

D039  5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid ethyl ester;

D040  5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid 2-methoxy-ethyl ester;

D041  5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid 2-ethoxy-ethyl ester;

D042  5-(3,5-Difluoro-benzenesulfonyl)-3-[4-[(2-dimethylamino-propyl)-methyl-amino]-2-(2-methoxy-ethylamino)-benzoylamino]-4,5,6,7-tetrahydro-pyrazolo[4,3-c]pyridine-1-carboxylic acid 2-(2-methoxy-ethoxy)-ethyl ester;

D043 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid methyl ester;

D044 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid ethyl ester;

D045 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid propyl ester;

D046 5-(3,5-Difluoro-benzenesulfonyl)-3-[4-(2-dimethylamino-ethoxy)-2-(2-methoxy-ethylamino)-benzoylamino]-4,5,6,7-tetrahydro-pyrazolo[4,3-c]pyridine-1-carboxylic acid isopropyl ester;

D047  5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid methyl ester;

D048  5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid ethyl ester;

D049  5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid 2-methoxy-ethyl ester;

D050  5-(3,5-Difluoro-benzenesulfonyl)-3-[4-(2-pyrrolidin-1-yl-ethoxy)-2-(2-methoxy-ethylamino)-benzoylamino]-4,5,6,7-tetrahydro-pyrazolo[4,3-c]pyridine-1-carboxylic acid 2-ethoxy-ethyl ester;

D051 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid methyl ester;

D052 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid ethyl ester;

D053 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid propyl ester;

D054 5-(3,5-Difluoro-benzenesulfonyl)-3-[4-(pyrrolidin-1-ylmethyl)-2-(2-methoxy-ethylamino)-benzoylamino]-4,5,6,7-tetrahydro-pyrazolo[4,3-c]pyridine-1-carboxylic acid isopropyl ester;

D055  S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D056  S-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D057  S-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D058  S-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D059  S-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D060  S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D061  S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D062  S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D063  S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D064  S-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydropyrazolo[4,3-c]pyridine-1-carboxylic acid 2-(2-methoxy-ethoxy)-ethyl ester;

D065 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D066 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D067 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D068 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D069 S-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D070 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid methyl ester;

D071 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D072 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid propyl ester;

D073 S-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid isopropyl ester;

D074 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D075 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D076 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D077 S-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D078 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D079 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid ethyl ester;

D080 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid propyl ester;

D081 S-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid isopropyl ester;

D082 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid methyl ester;

D083 R-5-(3,5-Difluoro-benzenesulfonyl)-3-[2-(2-methoxy-1-methyl-ethylamino)-4-(4-methyl-piperazin-1-yl)-benzoylamino]-4,5,6,7-tetrahydro-pyrazolo[4,3-c]pyridine-1-carboxylic acid ethyl ester;

D084 R-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D085 R-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D086 R-5-(3,5-Difluoro-benzenesulfonyl)-3-[4-(4-methyl-piperazin-1-yl)-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D087 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D088 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D089 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D090 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D091 R-5-(3,5-Difluoro-benzenesulfonyl)-3-[4-[(2-dimethylamino-ethyl)-methyl-amino]-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D092 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid methyl ester;

D093 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid ethyl ester;

D094 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D095 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D096 R-5-(3,5-Difluoro-benzenesulfonyl)-3-[4-[(2-dimethylamino-propyl)-methyl-amino]-2-(2-methoxy-1-methyl-ethylamino)-benzoylamino]-4,5,6,7-tetrahydro-pyrazolo[4,3-c]pyridine-1-carboxylic acid 2-(2-methoxy-ethoxy)-ethyl ester;

D097 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid methyl ester;

D098 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D099 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid propyl ester;

D0100 R-5-(3,5-Difluoro-benzenesulfonyl)-3-[4-(2-dimethylamino-ethoxy)-2-(2-methoxy-1-methyl-ethylamino)-benzoylamino]-4,5,6,7-tetrahydro-pyrazolo[4,3-c]pyridine-1-carboxylic acid isopropyl ester;

D0101 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid methyl ester;

D0102 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid ethyl ester;

D0103 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid 2-methoxy-ethyl ester;

D0104 R-5-(3,5-Difluoro-benzenesulfonyl)-3-[4-(2-pyrrolidin-1-yl-ethoxy)-2-(2-methoxy-1-methyl-ethylamino)-benzoylamino]-4,5,6,7-tetrahydro-pyrazolo[4,3-c]pyridine-1-carboxylic acid 2-ethoxy-ethyl ester;

D0105 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid methyl ester;

D0106 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid ethyl ester;

D0107 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid propyl ester;

D0108 R-5-(3,5-Difluoro-benzenesulfonyl)-3-[4-(pyrrolidin-1-ylmethyl)-2-(2-methoxy-1-methyl-ethylamino)-benzoylamino]-4,5,6,7-tetrahydro-pyrazolo[4,3-c]pyridine-1-carboxylic acid isopropyl ester;

E01 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid ethyl ester;

E02 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-methoxy-ethyl ester;

E03 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-ethoxy-ethyl ester;

E04 5-(3,5-Difluoro-benzenesulfonyl)-3-[4-(4-methyl-piperazin-1-yl)-2-(tetrahydro-pyran-4-ylamino)-benzoylamino]-indazole-1-carboxylic acid 2-(2-methoxy-ethoxy)-ethyl ester;

E05 5-(3,5-Difluoro-benzenesulfonyl)-3-[4-(2-dimethylamino-ethyl)-2-(tetrahydro-pyran-4-ylamino)-benzoylamino]-indazole-1-carboxylic acid methyl ester;

E06 5-(3,5-Difluoro-benzenesulfonyl)-3-[4-(2-dimethylamino-ethyl)-2-(tetrahydro-pyran-4-ylamino)-benzoylamino]-indazole-1-carboxylic acid ethyl ester;

E07 5-(3,5-Difluoro-benzenesulfonyl)-3-[4-(2-dimethylamino-ethyl)-2-(tetrahydro-pyran-4-ylamino)-benzoylamino]-indazole-1-carboxylic acid 2-methoxy-ethyl ester;

E08 5-(3,5-Difluoro-benzenesulfonyl)-3-[4-(2-dimethylamino-ethyl)-2-(tetrahydro-pyran-4-ylamino)-benzoylamino]-indazole-1-carboxylic acid 2-ethoxy-ethyl ester;

E09 5-(3,5-Difluoro-benzenesulfonyl)-3-[4-(2-dimethylamino-propyl)-2-(tetrahydro-pyran-4-ylamino)-benzoylamino]-indazole-1-carboxylic acid methyl ester;

E010 5-(3,5-Difluoro-benzenesulfonyl)-3-[4-(2-dimethylamino-propyl)-2-(tetrahydro-pyran-4-ylamino)-benzoylamino]-indazole-1-carboxylic acid ethyl ester;

E011 5-(3,5-Difluoro-benzenesulfonyl)-3-[4-(2-dimethylamino-propyl)-2-(tetrahydro-pyran-4-ylamino)-benzoylamino]-indazole-1-carboxylic acid 2-methoxy-ethyl ester;

E012 5-(3,5-Difluoro-benzenesulfonyl)-3-[4-(2-dimethylamino-propyl)-2-(tetrahydro-pyran-4-ylamino)-benzoylamino]-indazole-1-carboxylic acid 2-ethoxy-ethyl ester;

E013 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid methyl ester;

E014 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid ethyl ester;

E015 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid 2-methoxy-ethyl ester;

E016 5-(3,5-Difluoro-benzenesulfonyl)-3-[4-(2-dimethylamino-ethoxy)-2-(tetrahydro-pyran-4-ylamino)-benzoylamino]-indazole-1-carboxylic acid 2-ethoxy-ethyl ester;

E017 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid methyl ester;

E018 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid ethyl ester;

E019 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid 2-methoxy-ethyl ester;

E020 5-(3,5-Difluoro-benzenesulfonyl)-3-[4-(pyrrolidin-1-ylmethyl)-2-(tetrahydro-pyran-4-ylamino)-benzoylamino]-indazole-1-carboxylic acid 2-ethoxy-ethyl ester;

E021  5-(3,5-Difluoro-benzenesulfonyl)-3-[4-(4-methyl-piperazin-1-yl)-2-(2-methoxy-ethylamino)-benzoylamino]-indazole-1-carboxylic acid 2-methoxy-ethyl ester;

E022  5-(3,5-Difluoro-benzenesulfonyl)-3-[4-(4-methyl-piperazin-1-yl)-2-(2-methoxy-ethylamino)-benzoylamino]-indazole-1-carboxylic acid 2-ethoxy-ethyl ester;

E023  5-(3,5-Difluoro-benzenesulfonyl)-3-[4-(4-methyl-piperazin-1-yl)-2-(2-methoxy-ethylamino)-benzoylamino]-indazole-1-carboxylic acid 2-(2-methoxy-ethoxy)-ethyl ester;

E024  5-(3,5-Difluoro-benzenesulfonyl)-3-[4-(2-dimethylamino-ethyl)-2-(2-methoxy-ethylamino)-benzoylamino]-indazole-1-carboxylic acid methyl ester;

E025  5-(3,5-Difluoro-benzenesulfonyl)-3-[4-(2-dimethylamino-ethyl)-2-(2-methoxy-ethylamino)-benzoylamino]-indazole-1-carboxylic acid ethyl ester;

E026  5-(3,5-Difluoro-benzenesulfonyl)-3-[4-(2-dimethylamino-ethyl)-2-(2-methoxy-ethylamino)-benzoylamino]-indazole-1-carboxylic acid 2-methoxy-ethyl ester;

E027  5-(3,5-Difluoro-benzenesulfonyl)-3-[4-(2-dimethylamino-ethyl)-2-(2-methoxy-ethylamino)-benzoylamino]-indazole-1-carboxylic acid 2-ethoxy-ethyl ester;

E028  5-(3,5-Difluoro-benzenesulfonyl)-3-[4-(2-dimethylamino-propyl)-2-(2-methoxy-ethylamino)-benzoylamino]-indazole-1-carboxylic acid methyl ester;

E029  5-(3,5-Difluoro-benzenesulfonyl)-3-[4-(2-dimethylamino-propyl)-2-(2-methoxy-ethylamino)-benzoylamino]-indazole-1-carboxylic acid ethyl ester;

E030  5-(3,5-Difluoro-benzenesulfonyl)-3-[4-(2-dimethylamino-propyl)-2-(2-methoxy-ethylamino)-benzoylamino]-indazole-1-carboxylic acid 2-methoxy-ethyl ester;

E031  5-(3,5-Difluoro-benzenesulfonyl)-3-[4-(2-dimethylamino-propyl)-2-(2-methoxy-ethylamino)-benzoylamino]-indazole-1-carboxylic acid 2-ethoxy-ethyl ester;

E032  5-(3,5-Difluoro-benzenesulfonyl)-3-[4-(2-dimethylamino-ethoxy)-2-(2-methoxy-ethylamino)-benzoylamino]-indazole-1-carboxylic acid methyl ester;

E033  5-(3,5-Difluoro-benzenesulfonyl)-3-[4-(2-dimethylamino-ethoxy)-2-(2-methoxy-ethylamino)-benzoylamino]-indazole-1-carboxylic acid ethyl ester;

E034  5-(3,5-Difluoro-benzenesulfonyl)-3-[4-(2-dimethylamino-ethoxy)-2-(2-methoxy-ethylamino)-benzoylamino]-indazole-1-carboxylic acid 2-methoxy-ethyl ester;

E035  5-(3,5-Difluoro-benzenesulfonyl)-3-[4-(2-dimethylamino-ethoxy)-2-(2-methoxy-ethylamino)-benzoylamino]-indazole-1-carboxylic acid 2-ethoxy-ethyl ester;

E036  5-(3,5-Difluoro-benzenesulfonyl)-3-[4-(pyrrolidin-1-ylmethyl)-2-(2-methoxy-ethylamino)-benzoylamino]-indazole-1-carboxylic acid methyl ester;

E037  5-(3,5-Difluoro-benzenesulfonyl)-3-[4-(pyrrolidin-1-ylmethyl)-2-(2-methoxy-ethylamino)-benzoylamino]-indazole-1-carboxylic acid ethyl ester;

E038  5-(3,5-Difluoro-benzenesulfonyl)-3-[4-(pyrrolidin-1-ylmethyl)-2-(2-methoxy-ethylamino)-benzoylamino]-indazole-1-carboxylic acid 2-methoxy-ethyl ester;

E039  5-(3,5-Difluoro-benzenesulfonyl)-3-[4-(pyrrolidin-1-ylmethyl)-2-(2-methoxy-ethylamino)-benzoylamino]-indazole-1-carboxylic acid 2-ethoxy-ethyl ester;

E040  5-(3,5-Difluoro-benzenesulfonyl)-3-[2-((S)-2-methoxy-1-methyl-ethylamino)-4-(4-methyl-piperazin-1-yl)-benzoylamino]-indazole-1-carboxylic acid ethyl ester;

E041  S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-methoxy-ethyl ester;

E042  S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-ethoxy-ethyl ester;

E043  S-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxy-ethoxy)-ethyl ester;

E044  S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E045  S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E046  S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-methoxy-ethyl ester;

E047  S-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-ethoxy-ethyl ester;

E048  S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E049  S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid ethyl ester;

E050  S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-methoxy-ethyl ester;

E051  S-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-ethoxy-ethyl ester;

E052  S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid methyl ester;

E053  S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid ethyl ester;

E054  S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-methoxy-ethyl ester;

E055 S-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-ethoxy-ethyl ester;

E056 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E057 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester;

E058 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-methoxy-ethyl ester;

E059 S-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-ethoxy-ethyl ester;

E060 5-(3,5-Difluoro-benzenesulfonyl)-3-[2-((R)-2-methoxy-1-methyl-ethylamino)-4-(4-methyl-piperazin-1-yl)-benzoylamino]-indazole-1-carboxylic acid ethyl ester;

E061 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-methoxy-ethyl ester;

E062 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-ethoxy-ethyl ester;

E063 R-5-(3,5-Difluoro-benzenesulfonyl)-3-[4-(4-methyl-piperazin-1-yl)-2-(2-methoxy-1-methyl-ethylamino)-benzoylamino]-indazole-1-carboxylic acid 2-(2-methoxy-ethoxy)-ethyl ester;

E064 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid methyl ester;

E065 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid ethyl ester;

E066 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-methoxy-ethyl ester;

E067 R-5-(3,5-Difluoro-benzenesulfonyl)-3-[4-(2-dimethylamino-ethyl)-2-(2-methoxy-1-methyl-ethylamino)-benzoylamino]-indazole-1-carboxylic acid 2-ethoxy-ethyl ester;

E068 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid methyl ester;

E069 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid ethyl ester;

E070 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-methoxy-ethyl ester;

E071 R-5-(3,5-Difluoro-benzenesulfonyl)-3-[4-(2-dimethylamino-propyl)-2-(2-methoxy-1-methyl-ethylamino)-benzoylamino]-indazole-1-carboxylic acid 2-ethoxy-ethyl ester;

E072 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid methyl ester;

E073 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid ethyl ester;

E074 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-methoxy-ethyl ester;

E075 R-5-(3,5-Difluoro-benzenesulfonyl)-3-[4-(2-dimethylamino-ethoxy)-2-(2-methoxy-1-methyl-ethylamino)-benzoylamino]-indazole-1-carboxylic acid 2-ethoxy-ethyl ester;

E076 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid methyl ester;

E077 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid ethyl ester;

E078 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-methoxy-ethyl ester;

E079 R-5-(3,5-Difluoro-benzenesulfonyl)-3-[4-(pyrrolidin-1-ylmethyl)-2-(2-methoxy-1-methyl-ethylamino)-benzoylamino]-indazole-1-carboxylic acid 2-ethoxy-ethyl ester and E080 5-(3,5-Difluoro-benzenesulfonyl)-3-[2-(2-methoxy-ethylamino)-4-(4-methyl-piperazin-1-yl)-benzoylamino]-indazole-1-carboxylic acid ethyl ester, for use as medicament.

3. A method according to claim 2, with the exclusion of compounds coded A02, A024 and C024, or pharmaceutically acceptable salts thereof.

* * * * *

SEQUENCE LISTING

<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: carboxy-terminally biotinylated peptide

<400> SEQUENCE: 1

Lys Lys Lys Ser Pro Gly Glu Tyr Val Asn Ile Glu Phe Gly Gly Gly
1               5                   10                  15

Gly Gly Lys

<210> SEQ ID NO 2
<211> LENGTH: 7
<212> TYPE: PRT
<213> ORGANISM: Artificial Sequence
<220> FEATURE:
<223> OTHER INFORMATION: biotinylated peptide

<400> SEQUENCE: 2

Leu Arg Arg Trp Ser Leu Gly
1               5